United States Patent
Collinson et al.

(10) Patent No.: US 11,771,796 B2
(45) Date of Patent: Oct. 3, 2023

(54) WOUND DRESSING AND METHOD OF TREATMENT

(71) Applicant: Smith & Nephew PLC, Watford (GB)

(72) Inventors: Sarah Jenny Collinson, Hull (GB); Nicholas Charlton Fry, York (GB); Philip Gowans, Doncaster (GB); Edward Yerbury Hartwell, Hull (GB); Marcus Damian Phillips, Wakefield (GB)

(73) Assignee: Smith & Nephew PLC, Watford (GB)

( * ) Notice: Subject to any disclaimer, the term of this patent is extended or adjusted under 35 U.S.C. 154(b) by 0 days.

(21) Appl. No.: 17/743,371

(22) Filed: May 12, 2022

(65) Prior Publication Data

US 2022/0280713 A1 Sep. 8, 2022

Related U.S. Application Data

(63) Continuation of application No. 16/698,050, filed on Nov. 27, 2019, which is a continuation of application
(Continued)

(51) Int. Cl.
*A61L 15/42* (2006.01)
*A61F 13/00* (2006.01)
(Continued)

(52) U.S. Cl.
CPC ........ *A61L 15/42* (2013.01); *A61F 13/00029* (2013.01); *A61F 13/00068* (2013.01);
(Continued)

(58) Field of Classification Search
CPC .......... A61M 1/90; A61M 1/915; A61M 1/71; A61M 1/77; A61M 1/912;
(Continued)

(56) References Cited

U.S. PATENT DOCUMENTS

| 2,331,271 A | 10/1943 | Gilchrist |
| 2,727,382 A | 12/1955 | Karl et al. |

(Continued)

FOREIGN PATENT DOCUMENTS

| CN | 1293953 A | 5/2001 |
| CN | 2676918 Y | 2/2005 |

(Continued)

OTHER PUBLICATIONS

Advantec MFS, Inc., "Membrane Filters" (catalog), retrieved from http://www.advantecmfs.com/catalog/filt/membrane.pdf, on Jan. 29, 2016, Copyright 2001-2011, 17 pages.
(Continued)

*Primary Examiner* — Susan S Su
(74) *Attorney, Agent, or Firm* — Knobbe, Martens, Olson & Bear, LLP

(57) ABSTRACT

Embodiments disclosed herein are directed to negative pressure treatment systems and wound dressing systems, apparatuses, and methods that may be used for the treatment of wounds. In particular, some embodiments are directed to improved wound dressings comprising a bridge portion connecting two or more portions of an absorbent layer that facilitates trimming of the wound dressing to suitable sizes. Some embodiments provide for trimming the dressing in a gap between two or more portions of an absorbent layer and sealing the exposed portion of dressing after trimming when the dressing is applied to skin surrounding a wound.

17 Claims, 55 Drawing Sheets

Related U.S. Application Data

No. 14/775,494, filed as application No. PCT/GB2014/050781 on Mar. 14, 2014, now Pat. No. 10,493,184.

(60) Provisional application No. 61/907,350, filed on Nov. 21, 2013, provisional application No. 61/906,865, filed on Nov. 20, 2013, provisional application No. 61/829,187, filed on May 30, 2013, provisional application No. 61/828,604, filed on May 29, 2013, provisional application No. 61/800,040, filed on Mar. 15, 2013.

(51) Int. Cl.
*A61M 1/00* (2006.01)
*A61L 15/26* (2006.01)

(52) U.S. Cl.
CPC .............. *A61L 15/26* (2013.01); *A61L 15/425* (2013.01); *A61M 1/913* (2021.05); *A61M 1/915* (2021.05); *A61M 1/916* (2021.05)

(58) Field of Classification Search
CPC .......... A61F 13/00029; A61F 13/00068; A61F 13/0209; A61F 13/0216; A61F 13/0213; A61F 13/0263; A61F 2013/53051; A61F 2013/530562; A61F 2013/530802; A61F 2013/530839; A61F 2013/530861
See application file for complete search history.

(56) References Cited

U.S. PATENT DOCUMENTS

| | | |
|---|---|---|
| 2,877,765 A | 3/1959 | John et al. |
| 2,889,039 A | 6/1959 | Peter et al. |
| 3,073,304 A | 1/1963 | Schaar |
| 3,285,245 A | 11/1966 | Eldredge et al. |
| 3,929,135 A | 12/1975 | Thompson |
| 3,964,039 A | 6/1976 | Craford et al. |
| 3,972,328 A | 8/1976 | Chen |
| 4,029,598 A | 6/1977 | Neisius et al. |
| 4,093,277 A | 6/1978 | Nolan et al. |
| 4,095,599 A | 6/1978 | Simonet-Haibe |
| 4,224,941 A | 9/1980 | Stivala |
| 4,541,426 A | 9/1985 | Webster |
| 4,624,656 A | 11/1986 | Clark et al. |
| 4,681,562 A | 7/1987 | Beck et al. |
| 4,690,134 A | 9/1987 | Snyders |
| 4,699,134 A | 10/1987 | Samuelsen |
| 4,728,499 A | 3/1988 | Fehder |
| 4,770,187 A | 9/1988 | Lash et al. |
| 4,813,942 A | 3/1989 | Alvarez |
| 4,886,697 A | 12/1989 | Perdelwitz, Jr. et al. |
| 4,985,467 A | 1/1991 | Kelly et al. |
| 5,000,172 A | 3/1991 | Ward |
| 5,000,741 A | 3/1991 | Kalt |
| 5,056,510 A | 10/1991 | Gilman |
| 5,080,661 A | 1/1992 | Lavender et al. |
| 5,106,629 A | 4/1992 | Cartmell et al. |
| 5,152,757 A | 10/1992 | Eriksson |
| 5,181,905 A | 1/1993 | Flam |
| 5,238,732 A | 8/1993 | Krishnan |
| 5,264,218 A | 11/1993 | Rogozinski |
| 5,267,952 A | 12/1993 | Gardner |
| 5,360,420 A | 11/1994 | Cook et al. |
| 5,409,472 A | 4/1995 | Rawlings et al. |
| 5,447,492 A | 9/1995 | Cartmell et al. |
| 5,501,661 A | 3/1996 | Cartmell et al. |
| 5,520,629 A | 5/1996 | Heinecke et al. |
| 5,536,555 A | 7/1996 | Zelazoski et al. |
| 5,549,584 A | 8/1996 | Gross |
| 5,562,107 A | 10/1996 | Lavender et al. |
| 5,591,149 A | 1/1997 | Cree et al. |
| 5,605,165 A | 2/1997 | Sessions et al. |
| 5,626,954 A | 5/1997 | Andersen et al. |
| 5,643,189 A | 7/1997 | Masini |
| 5,707,499 A | 1/1998 | Joshi et al. |
| 5,735,145 A | 4/1998 | Pernick |
| 5,759,570 A | 6/1998 | Arnold |
| 5,795,439 A | 8/1998 | Euripides et al. |
| 5,795,584 A | 8/1998 | Totakura et al. |
| 5,804,021 A | 9/1998 | Abuto et al. |
| 5,833,646 A | 11/1998 | Masini |
| 5,840,052 A | 11/1998 | Johns |
| 5,852,126 A | 12/1998 | Barnard et al. |
| 5,868,724 A | 2/1999 | Dierckes, Jr. et al. |
| 5,960,795 A | 10/1999 | Schultz |
| 5,968,855 A | 10/1999 | Perdelwitz, Jr. et al. |
| 6,008,429 A | 12/1999 | Ritger |
| 6,018,092 A | 1/2000 | Dunshee |
| 6,071,267 A | 6/2000 | Zamierowski |
| 6,142,982 A | 11/2000 | Hunt et al. |
| 6,207,875 B1 | 3/2001 | Lindqvist et al. |
| 6,225,523 B1 | 5/2001 | Masini |
| 6,241,697 B1 | 6/2001 | Augustine |
| 6,261,283 B1 | 7/2001 | Morgan et al. |
| 6,297,422 B1 | 10/2001 | Hansen et al. |
| 6,312,416 B1 | 11/2001 | Brisebois et al. |
| 6,345,623 B1 | 2/2002 | Heaton et al. |
| 6,398,767 B1 | 6/2002 | Fleischmann |
| 6,447,799 B1 | 9/2002 | Ullman |
| 6,478,781 B1 | 11/2002 | Urich et al. |
| 6,482,491 B1 | 11/2002 | Samuelsen et al. |
| 6,497,688 B2 | 12/2002 | Lasko |
| D473,947 S | 4/2003 | Jacobson |
| 6,566,575 B1 | 5/2003 | Stickels et al. |
| 6,599,262 B1 | 7/2003 | Masini |
| 6,626,891 B2 | 9/2003 | Ohmstede |
| 6,638,270 B2 | 10/2003 | Johnson |
| 6,685,681 B2 | 2/2004 | Lockwood et al. |
| 6,752,794 B2 | 6/2004 | Lockwood et al. |
| 6,764,462 B2 | 7/2004 | Risk, Jr. et al. |
| 6,767,334 B1 | 7/2004 | Randolph |
| 6,776,769 B2 | 8/2004 | Smith |
| 6,936,037 B2 | 8/2005 | Bubb et al. |
| 6,951,553 B2 | 10/2005 | Bubb et al. |
| 6,979,324 B2 | 12/2005 | Bybordi et al. |
| 6,998,511 B2 | 2/2006 | Worthley |
| 7,004,915 B2 | 2/2006 | Boynton et al. |
| 7,022,113 B2 | 4/2006 | Lockwood et al. |
| D525,362 S | 7/2006 | Nielsen et al. |
| 7,070,584 B2 | 7/2006 | Johnson et al. |
| 7,108,683 B2 | 9/2006 | Zamierowski |
| D537,948 S | 3/2007 | Smith |
| 7,216,651 B2 | 5/2007 | Argenta et al. |
| 7,267,681 B2 | 9/2007 | Dunshee |
| 7,338,482 B2 | 3/2008 | Lockwood et al. |
| 7,361,184 B2 | 4/2008 | Joshi |
| 7,381,859 B2 | 6/2008 | Hunt et al. |
| 7,429,689 B2 | 9/2008 | Chen et al. |
| 7,468,471 B2 | 12/2008 | Sigurjonsson et al. |
| 7,485,112 B2 | 2/2009 | Karpowicz et al. |
| 7,524,315 B2 | 4/2009 | Blott et al. |
| 7,534,927 B2 | 5/2009 | Lockwood et al. |
| 7,553,306 B1 | 6/2009 | Hunt et al. |
| 7,569,742 B2 | 8/2009 | Haggstrom et al. |
| 7,576,256 B2 | 8/2009 | Bjornberg et al. |
| 7,605,298 B2 | 10/2009 | Bechert et al. |
| 7,611,500 B1 | 11/2009 | Lina et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,674,948 B2 | 3/2010 | Propp et al. |
| 7,678,102 B1 | 3/2010 | Heaton |
| 7,699,823 B2 | 4/2010 | Haggstrom et al. |
| 7,700,819 B2 | 4/2010 | Ambrosio et al. |
| 7,708,724 B2 | 5/2010 | Weston |
| 7,718,249 B2 | 5/2010 | Russell et al. |
| 7,722,582 B2 | 5/2010 | Lina et al. |
| 7,749,531 B2 | 7/2010 | Booher |
| 7,753,894 B2 | 7/2010 | Blott et al. |
| 7,759,537 B2 | 7/2010 | Bishop et al. |
| 7,759,539 B2 | 7/2010 | Shaw et al. |

(56) References Cited

U.S. PATENT DOCUMENTS

| | | |
|---|---|---|
| 7,775,998 B2 | 8/2010 | Riesinger |
| 7,779,625 B2 | 8/2010 | Joshi et al. |
| D625,018 S | 10/2010 | Smith et al. |
| 7,811,269 B2 | 10/2010 | Boynton et al. |
| 7,838,717 B2 | 11/2010 | Haggstrom et al. |
| 7,846,141 B2 | 12/2010 | Weston |
| 7,910,791 B2 | 3/2011 | Coffey |
| 7,922,703 B2 | 4/2011 | Riesinger |
| 7,959,624 B2 | 6/2011 | Riesinger |
| 7,964,766 B2 | 6/2011 | Blott et al. |
| 7,976,519 B2 | 7/2011 | Bubb et al. |
| 7,982,087 B2 | 7/2011 | Greener et al. |
| 8,034,037 B2 | 10/2011 | Adams et al. |
| 8,062,272 B2 | 11/2011 | Weston |
| 8,062,331 B2 | 11/2011 | Zamierowski |
| 8,080,702 B2 | 12/2011 | Blott et al. |
| 8,118,794 B2 | 2/2012 | Weston |
| 8,129,580 B2 | 3/2012 | Wilkes et al. |
| 8,152,785 B2 | 4/2012 | Vitaris |
| 8,162,907 B2 | 4/2012 | Heagle |
| 8,192,409 B2 | 6/2012 | Hardman et al. |
| 8,207,392 B2 | 6/2012 | Haggstrom et al. |
| 8,235,972 B2 | 8/2012 | Adahan |
| 8,241,261 B2 | 8/2012 | Randolph et al. |
| 8,282,611 B2 | 10/2012 | Weston |
| 8,303,552 B2 | 11/2012 | Weston |
| 8,372,049 B2 | 2/2013 | Jaeb et al. |
| 8,372,050 B2 | 2/2013 | Jaeb et al. |
| 8,382,731 B2 | 2/2013 | Johannison |
| 8,404,921 B2 | 3/2013 | Lee et al. |
| D679,402 S | 4/2013 | Conrad-Vlasak et al. |
| 8,425,478 B2 | 4/2013 | Olson |
| 8,444,611 B2 | 5/2013 | Wilkes et al. |
| 8,444,612 B2 | 5/2013 | Patel et al. |
| 8,454,580 B2 | 6/2013 | Locke et al. |
| 8,460,255 B2 | 6/2013 | Joshi et al. |
| 8,535,296 B2 | 9/2013 | Blott et al. |
| 8,540,687 B2 | 9/2013 | Henley et al. |
| 8,540,688 B2 | 9/2013 | Eckstein et al. |
| 8,545,466 B2 | 10/2013 | Andresen et al. |
| 8,568,386 B2 | 10/2013 | Malhi |
| 8,628,505 B2 | 1/2014 | Weston |
| 8,641,691 B2 | 2/2014 | Fink et al. |
| 8,663,198 B2 | 3/2014 | Buan et al. |
| 8,680,360 B2 | 3/2014 | Greener et al. |
| 8,715,256 B2 | 5/2014 | Greener |
| 8,764,732 B2 | 7/2014 | Hartwell |
| 8,795,243 B2 | 8/2014 | Weston |
| 8,795,247 B2 | 8/2014 | Bennett et al. |
| 8,795,800 B2 | 8/2014 | Evans |
| 8,808,274 B2 | 8/2014 | Hartwell |
| D712,546 S | 9/2014 | Igwebuike et al. |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,843,327 B2 | 9/2014 | Vernon-Harcourt et al. |
| 8,916,742 B2 | 12/2014 | Smith |
| 8,956,336 B2 | 2/2015 | Haggstrom et al. |
| 9,012,714 B2 | 4/2015 | Fleischmann |
| 9,061,095 B2 | 6/2015 | Adie et al. |
| 9,067,003 B2 | 6/2015 | Buan et al. |
| 9,127,665 B2 | 9/2015 | Locke et al. |
| 9,168,330 B2 | 10/2015 | Joshi et al. |
| 9,199,012 B2 | 12/2015 | Vitaris et al. |
| 9,220,822 B2 | 12/2015 | Hartwell |
| 9,254,353 B2 | 2/2016 | Locke et al. |
| 9,283,118 B2 | 3/2016 | Locke et al. |
| 9,302,033 B2 | 4/2016 | Riesinger |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,427,505 B2 | 8/2016 | Askem et al. |
| 9,446,178 B2 | 9/2016 | Blott et al. |
| 9,452,248 B2 | 9/2016 | Blott et al. |
| 9,474,661 B2 | 10/2016 | Fouillet et al. |
| 9,629,986 B2 | 4/2017 | Patel et al. |
| 9,669,138 B2 | 6/2017 | Joshi et al. |
| 9,795,725 B2 | 10/2017 | Joshi et al. |
| 9,808,561 B2 | 11/2017 | Adie et al. |
| 9,844,473 B2 | 12/2017 | Blott et al. |
| 10,016,545 B2 | 7/2018 | Vitaris et al. |
| RE47,100 E | 10/2018 | Smith et al. |
| 2001/0034499 A1 | 10/2001 | Sessions et al. |
| 2001/0051165 A1 | 12/2001 | Lenz et al. |
| 2002/0035352 A1 | 3/2002 | Ronnberg et al. |
| 2002/0052570 A1 | 5/2002 | Naimer |
| 2002/0062114 A1 | 5/2002 | Murai et al. |
| 2002/0183702 A1 | 12/2002 | Henley et al. |
| 2003/0014025 A1 | 1/2003 | Allen et al. |
| 2003/0014786 P1 | 1/2003 | Meilland |
| 2003/0108587 A1 | 6/2003 | Orgill et al. |
| 2003/0125646 A1 | 7/2003 | Whitlock |
| 2003/0212357 A1 | 11/2003 | Pace |
| 2004/0015115 A1 | 1/2004 | Sinyagin |
| 2004/0019338 A1 | 1/2004 | Litvay et al. |
| 2004/0030304 A1* | 2/2004 | Hunt .................... A61M 1/915 604/317 |
| 2004/0057855 A1 | 3/2004 | Gerlach et al. |
| 2004/0064132 A1 | 4/2004 | Boehringer et al. |
| 2004/0087884 A1 | 5/2004 | Haddock et al. |
| 2004/0167482 A1 | 8/2004 | Watson |
| 2005/0084641 A1 | 4/2005 | Downs et al. |
| 2005/0090860 A1 | 4/2005 | Paprocki |
| 2005/0209574 A1 | 9/2005 | Boehringer et al. |
| 2005/0222527 A1 | 10/2005 | Miller et al. |
| 2005/0288691 A1 | 12/2005 | Leiboff |
| 2006/0009744 A1 | 1/2006 | Erdman et al. |
| 2006/0020234 A1 | 1/2006 | Chou et al. |
| 2006/0047257 A1 | 3/2006 | Raidel et al. |
| 2006/0184150 A1 | 8/2006 | Noel |
| 2007/0016152 A1 | 1/2007 | Karpowicz et al. |
| 2007/0032763 A1 | 2/2007 | Vogel |
| 2007/0040454 A1 | 2/2007 | Freudenberger et al. |
| 2007/0055029 A1 | 3/2007 | Suzuki et al. |
| 2007/0055209 A1 | 3/2007 | Patel et al. |
| 2007/0060892 A1 | 3/2007 | Propp |
| 2007/0073200 A1 | 3/2007 | Hannigan et al. |
| 2007/0219497 A1 | 9/2007 | Johnson et al. |
| 2007/0219512 A1 | 9/2007 | Heaton et al. |
| 2007/0220692 A1 | 9/2007 | Kusin |
| 2007/0225663 A1 | 9/2007 | Watt et al. |
| 2007/0239232 A1 | 10/2007 | Kurtz et al. |
| 2007/0255194 A1 | 11/2007 | Gudnason et al. |
| 2008/0031748 A1 | 2/2008 | Ihle et al. |
| 2008/0113143 A1 | 5/2008 | Taylor |
| 2008/0132821 A1 | 6/2008 | Propp et al. |
| 2008/0172017 A1 | 7/2008 | Carlucci et al. |
| 2008/0306456 A1 | 12/2008 | Riesinger |
| 2009/0012483 A1 | 1/2009 | Blott et al. |
| 2009/0043268 A1 | 2/2009 | Eddy et al. |
| 2009/0099519 A1 | 4/2009 | Kaplan |
| 2009/0105670 A1 | 4/2009 | Bentley et al. |
| 2009/0125004 A1 | 5/2009 | Shen et al. |
| 2009/0157024 A1 | 6/2009 | Song |
| 2009/0227968 A1 | 9/2009 | Vess |
| 2009/0234306 A1 | 9/2009 | Vitaris |
| 2009/0299251 A1 | 12/2009 | Buan |
| 2009/0299306 A1 | 12/2009 | Buan |
| 2009/0299342 A1* | 12/2009 | Cavanaugh, II .... A61F 13/0223 604/543 |
| 2009/0306609 A1 | 12/2009 | Blott et al. |
| 2009/0326430 A1 | 12/2009 | Frederiksen et al. |
| 2010/0063484 A1 | 3/2010 | Heagle |
| 2010/0069858 A1 | 3/2010 | Olson |
| 2010/0087767 A1 | 4/2010 | McNeil |
| 2010/0100022 A1* | 4/2010 | Greener ............ A61F 13/00995 83/13 |
| 2010/0106113 A1 | 4/2010 | Heinecke |
| 2010/0125234 A1 | 5/2010 | Smith |
| 2010/0125258 A1 | 5/2010 | Coulthard et al. |
| 2010/0137775 A1 | 6/2010 | Hu et al. |
| 2010/0174250 A1 | 7/2010 | Hu et al. |
| 2010/0198127 A1 | 8/2010 | Addison |
| 2010/0259406 A1 | 10/2010 | Caso et al. |

(56) References Cited

U.S. PATENT DOCUMENTS

| | | |
|---|---|---|
| 2010/0305526 A1 | 12/2010 | Robinson et al. |
| 2010/0312159 A1 | 12/2010 | Aali et al. |
| 2010/0318043 A1 | 12/2010 | Malhi et al. |
| 2010/0318052 A1 | 12/2010 | Ha et al. |
| 2011/0004172 A1 | 1/2011 | Eckstein et al. |
| 2011/0021964 A1 | 1/2011 | Larsen et al. |
| 2011/0034892 A1* | 2/2011 | Buan .......... A61F 13/00068 604/385.03 |
| 2011/0070391 A1 | 3/2011 | Cotton |
| 2011/0077605 A1 | 3/2011 | Karpowicz et al. |
| 2011/0112492 A1 | 5/2011 | Bharti et al. |
| 2011/0118683 A1 | 5/2011 | Weston |
| 2011/0184364 A1 | 7/2011 | Biggs et al. |
| 2011/0224631 A1 | 9/2011 | Simmons et al. |
| 2011/0257611 A1 | 10/2011 | Locke et al. |
| 2011/0282309 A1 | 11/2011 | Adie et al. |
| 2011/0313373 A1 | 12/2011 | Riesinger |
| 2011/0313374 A1 | 12/2011 | Lockwood et al. |
| 2011/0319801 A1 | 12/2011 | Ital et al. |
| 2011/0319804 A1* | 12/2011 | Greener .......... A61F 13/00987 83/13 |
| 2012/0051945 A1 | 3/2012 | Orndorff et al. |
| 2012/0095380 A1 | 4/2012 | Gergely et al. |
| 2012/0116334 A1 | 5/2012 | Albert et al. |
| 2012/0123358 A1 | 5/2012 | Hall et al. |
| 2012/0136326 A1 | 5/2012 | Croizat et al. |
| 2012/0150078 A1 | 6/2012 | Chen et al. |
| 2012/0220973 A1 | 8/2012 | Chan et al. |
| 2012/0222687 A1 | 9/2012 | Czajka, Jr. et al. |
| 2012/0232502 A1 | 9/2012 | Lowing |
| 2012/0308780 A1 | 12/2012 | Rottger et al. |
| 2013/0012902 A1 | 1/2013 | Rovaniemi |
| 2013/0052152 A1 | 2/2013 | Keplinger |
| 2013/0066285 A1 | 3/2013 | Locke et al. |
| 2013/0066289 A1 | 3/2013 | Song et al. |
| 2013/0090616 A1 | 4/2013 | Neubauer |
| 2013/0138054 A1 | 5/2013 | Fleischmann |
| 2013/0144227 A1 | 6/2013 | Locke et al. |
| 2013/0144230 A1 | 6/2013 | Wu et al. |
| 2013/0150814 A1 | 6/2013 | Buan |
| 2013/0165878 A1 | 6/2013 | Heagle |
| 2013/0211349 A1 | 8/2013 | Stokes et al. |
| 2013/0274688 A1 | 10/2013 | Weston |
| 2013/0296762 A1 | 11/2013 | Toth |
| 2013/0302545 A1 | 11/2013 | Schnelker et al. |
| 2013/0310781 A1 | 11/2013 | Phillips et al. |
| 2014/0010673 A1 | 1/2014 | Locke et al. |
| 2014/0012213 A1 | 1/2014 | Locke et al. |
| 2014/0114268 A1 | 4/2014 | Auguste et al. |
| 2014/0127148 A1 | 5/2014 | Derain |
| 2014/0171888 A1 | 6/2014 | Croizat et al. |
| 2014/0200533 A1 | 7/2014 | Whyte et al. |
| 2014/0228791 A1 | 8/2014 | Hartwell |
| 2014/0236109 A1 | 8/2014 | Greener |
| 2014/0303575 A1 | 10/2014 | May |
| 2014/0316359 A1 | 10/2014 | Collinson et al. |
| 2014/0350496 A1 | 11/2014 | Riesinger |
| 2015/0032035 A1 | 1/2015 | Banwell et al. |
| 2015/0057625 A1 | 2/2015 | Coulthard |
| 2015/0065965 A1 | 3/2015 | Haggstrom et al. |
| 2015/0119831 A1 | 4/2015 | Robinson et al. |
| 2015/0119832 A1 | 4/2015 | Locke |
| 2015/0119833 A1 | 4/2015 | Coulthard et al. |
| 2015/0159066 A1 | 6/2015 | Hartwell et al. |
| 2015/0174304 A1 | 6/2015 | Askem et al. |
| 2015/0182677 A1 | 7/2015 | Collinson et al. |
| 2015/0190286 A1 | 7/2015 | Allen et al. |
| 2015/0216733 A1 | 8/2015 | Allen et al. |
| 2015/0306273 A1 | 10/2015 | Karim et al. |
| 2015/0308994 A1 | 10/2015 | Hammond et al. |
| 2015/0335798 A1 | 11/2015 | De Samber et al. |
| 2016/0000610 A1 | 1/2016 | Riesinger |
| 2016/0000611 A1 | 1/2016 | Niederauer et al. |
| 2016/0081859 A1 | 3/2016 | Hartwell |
| 2016/0136339 A1 | 5/2016 | Begin et al. |
| 2016/0262942 A1 | 9/2016 | Riesinger |
| 2016/0298620 A1 | 10/2016 | Cordoba et al. |
| 2016/0317357 A1 | 11/2016 | Vitaris et al. |
| 2017/0007751 A1 | 1/2017 | Hartwell et al. |
| 2017/0128642 A1 | 5/2017 | Buan |
| 2017/0181896 A1 | 6/2017 | Hartwell |
| 2017/0181897 A1 | 6/2017 | Hartwell |
| 2018/0318476 A1 | 11/2018 | Askem et al. |
| 2019/0125590 A1 | 5/2019 | Rehbein et al. |
| 2020/0121833 A9 | 4/2020 | Askem et al. |
| 2021/0052431 A1 | 2/2021 | Lattimore et al. |
| 2021/0386592 A1 | 12/2021 | Greener et al. |

FOREIGN PATENT DOCUMENTS

| | | |
|---|---|---|
| CN | 2843399 Y | 12/2006 |
| CN | 201139694 Y | 10/2008 |
| CN | 101415818 A | 4/2009 |
| CN | 201375590 Y | 1/2010 |
| CN | 201418816 Y | 3/2010 |
| CN | 101959479 A | 1/2011 |
| CN | 102089017 A | 6/2011 |
| CN | 102274574 A | 12/2011 |
| CN | 102458334 A | 5/2012 |
| CN | 202263100 U | 6/2012 |
| DE | 3443101 A1 | 5/1986 |
| DE | 4030465 A1 | 4/1992 |
| EP | 0053936 A2 | 6/1982 |
| EP | 0340018 A2 | 11/1989 |
| EP | 0768071 A1 | 4/1997 |
| EP | 1353001 A1 | 10/2003 |
| EP | 0630629 B1 | 11/2004 |
| EP | 1955887 A2 | 8/2008 |
| EP | 2366721 A1 | 9/2011 |
| EP | 2529767 A2 | 12/2012 |
| EP | 2477674 B1 | 7/2013 |
| EP | 2269603 B1 | 5/2015 |
| FR | 1163907 A | 10/1958 |
| GB | 1255395 A | 12/1971 |
| GB | 2331937 A | 6/1999 |
| GB | 2307180 B | 6/2000 |
| GB | 2389794 A | 12/2003 |
| GB | 2468905 A | 9/2010 |
| JP | S5230463 U | 3/1977 |
| JP | S57119738 A | 7/1982 |
| JP | H02131432 U | 11/1990 |
| JP | 2006025918 A | 2/2006 |
| JP | 2008073187 A | 4/2008 |
| JP | 2008183244 A | 8/2008 |
| JP | 2011521736 A | 7/2011 |
| JP | 2011530344 A | 12/2011 |
| JP | 2012016476 A | 1/2012 |
| RU | 62504 U1 | 4/2007 |
| RU | 2432177 C1 | 10/2011 |
| WO | WO-8300742 A1 | 3/1983 |
| WO | WO-9216245 A1 | 10/1992 |
| WO | WO-9605873 A1 | 2/1996 |
| WO | WO-9741816 A1 | 11/1997 |
| WO | WO-9963922 A1 | 12/1999 |
| WO | WO-0154743 A1 | 8/2001 |
| WO | WO-03051409 A1 | 6/2003 |
| WO | WO-03086232 A2 | 10/2003 |
| WO | WO-2004077387 A1 | 9/2004 |
| WO | WO-2005046760 A1 | 5/2005 |
| WO | WO-2005105180 A1 | 11/2005 |
| WO | WO-2007013049 A1 | 2/2007 |
| WO | WO-2007066699 A1 | 6/2007 |
| WO | WO-2007113597 A2 | 10/2007 |
| WO | WO-2008039223 A1 | 4/2008 |
| WO | WO-2008100437 A1 | 8/2008 |
| WO | WO-2009001590 A1 | 12/2008 |
| WO | WO-2009021523 A1 | 2/2009 |
| WO | WO-2009111657 A2 | 9/2009 |
| WO | WO-2009114760 A1 | 9/2009 |
| WO | WO-2009135171 A2 | 11/2009 |
| WO | WO-2009146441 A1 | 12/2009 |
| WO | WO-2009147402 A2 | 12/2009 |
| WO | WO-2009156949 A2 | 12/2009 |
| WO | WO-2009158128 A2 | 12/2009 |

(56) References Cited

FOREIGN PATENT DOCUMENTS

| | | |
|---|---|---|
| WO | WO-2010010398 A1 | 1/2010 |
| WO | WO-2010016791 A1 | 2/2010 |
| WO | WO-2010122665 A1 | 10/2010 |
| WO | WO-2011028407 A1 | 3/2011 |
| WO | WO-2011040970 A1 | 4/2011 |
| WO | WO-2011112870 A1 | 9/2011 |
| WO | WO-2011115908 A1 | 9/2011 |
| WO | WO-2011135284 A1 | 11/2011 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO-2011152368 A1 | 12/2011 |
| WO | WO-2012069793 A1 | 5/2012 |
| WO | WO-2012069794 A1 | 5/2012 |
| WO | WO-2012087376 A1 | 6/2012 |
| WO | WO-2012143665 A1 | 10/2012 |
| WO | WO-2013007973 A2 | 1/2013 |
| WO | WO-2013029652 A1 | 3/2013 |
| WO | WO-2013064852 A1 | 5/2013 |
| WO | WO-2013076450 A1 | 5/2013 |
| WO | WO-2013110008 A1 | 7/2013 |
| WO | WO-2013136181 A2 | 9/2013 |
| WO | WO-2013175306 A2 | 11/2013 |
| WO | WO-2014020400 A2 | 2/2014 |
| WO | WO-2014020440 A1 | 2/2014 |
| WO | WO-2014020443 A2 | 2/2014 |
| WO | WO-2014140606 A1 | 9/2014 |
| WO | WO-2014140608 A1 | 9/2014 |
| WO | WO-2015022340 A1 | 2/2015 |

OTHER PUBLICATIONS

Anonymous, "3M™ Tegaderm™ Transparent Film Dressings—Product Profile," Retrieved from http://multimedia.3m.com/mws/media/447983O/tegaderm-transparent-film-dressing-brochure.pdf, Jan. 1, 2012, 8 pages.

Brief Communication—Letter from the Proprietor of the Patent to Simmons & Simmons, re the Opposition of European Patent No. 2968648, dated Feb. 15, 2022, 23 pages.

Communication of a notice of opposition to the proprietor for European patent No. 2968648, mailed on Sep. 29, 2021, 22 pages.

Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.

International Preliminary Report on Patentability for Application No. PCT/GB2014/050781, dated Sep. 24, 2015, 9 pages.

International Search Report and Written Opinion for Application No. PCT/GB2014/050781, dated Jun. 13, 2014, 11 pages.

International Search Report and Written Opinion for Application No. PCT/GB2014/050786, dated Jun. 12, 2014, 14 pages.

KCI Licensing Inc, "Prevena™ Incision Management System—Clinician Guide—Instructions for Use," 390061 Rev D, Jan. 2010, 10 pages.

KCI Licensing Inc, "Prevena™ Incision Management System—Clinician Guide—Instructions for Use," 390153-WEB Rev B, Jan. 2010, 12 pages.

KCI Licensing, "Prevena™ Incision Management System—Patient Guide", 390064 Rev D, Jan. 2010, 4 pages.

KCI Licensing, "Prevena™ Incision Management System—Patient Guide," 390152-WEB C, Jan. 2011, 6 pages.

KCI Licensing, Prevena™ Incision Management System, Jun. 22, 2010, in 2 pages.

Kendall ULTEC Hydrocolloid Dressing (4×4"), Product Ordering Page, web page downloaded on Jul. 13, 2014, 1 page.

Protz K., "Modern Wound Dressings Support the Healing Process," Wound care: Indications and Application, Geriatrie Journal, Apr. 2005, pp. 3333-3339 (17 pages with English translation).

Smith & Nephew, Allevyn Gentle Border Multisite, Jun. 2011, 2 pages.

Smith & Nephew, "PICO Single Use Negative Pressure Wound Therapy System," Spiral Booklet, Mar. 2011, 7 pages.

Smith and Nephew Inc., "Allevyn Wound Dressings Pamphlet," 2008, 2 pages.

Technology Watch, May 1989, 1 page.

Smith and Nephew Medical Ltd., "Reach for the Right Dressing. Reach for Allevyn," Allevyn Educational Booklet, Apr. 2014, 2 pages.

Brief Communication—Letter from the Opponent O1 of Dec. 7, 2022, for European Patent No. 2968648, dated Dec. 12, 2022, 8 pages.

Brief Communication—Letter from the Proprietor of the Patent dated Dec. 5, 2022, for European Patent No. 2968648, dated Dec. 8, 2022, 23 pages.

Wikipedia, "Parallel (geometry)," retrieved from https://en.wikipedia.org/w/index.php?title=Parallel_(geometry)&oldid=1080576469, last edited on Apr. 2, 2022, 9 pages.

Summons to Attend Oral Proceedings pursuant to rule 115(1) EPC for the European Patent No. 2968648, mailed on May 19, 2022, 15 pages.

Information about the Result of Oral Proceedings for European Patent No. 2968648, dated Feb. 7, 2023, 4 pages.

Interlocutory Decision in Opposition proceedings (Art. 101(3)(a) and 106(2) EPC) for European Patent No. 2968648 mailed on Mar. 16, 2023, 176 pages.

Statement of Grounds of Appeal for European Patent No. 2968648, dated Jul. 17, 2023, 15 pages.

* cited by examiner

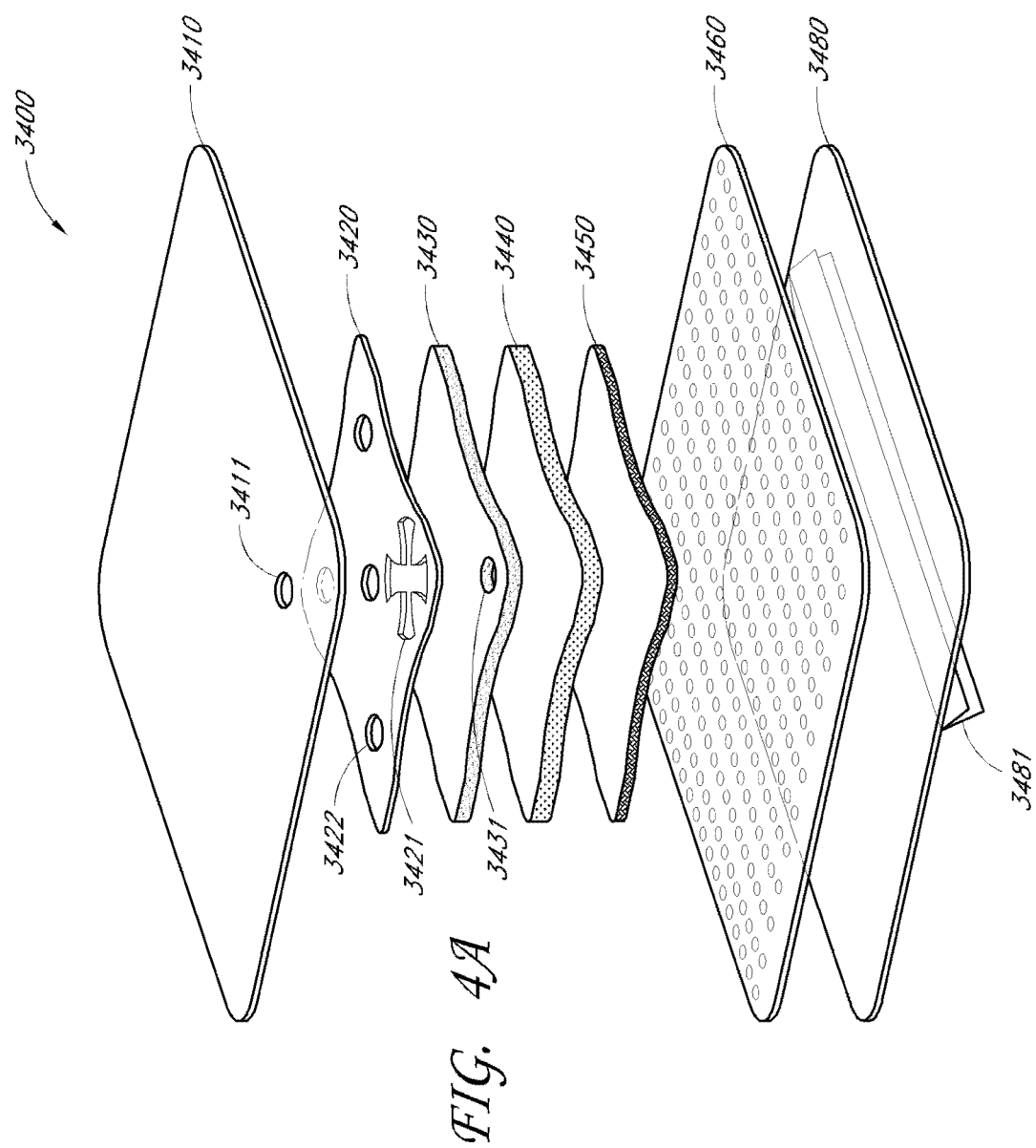

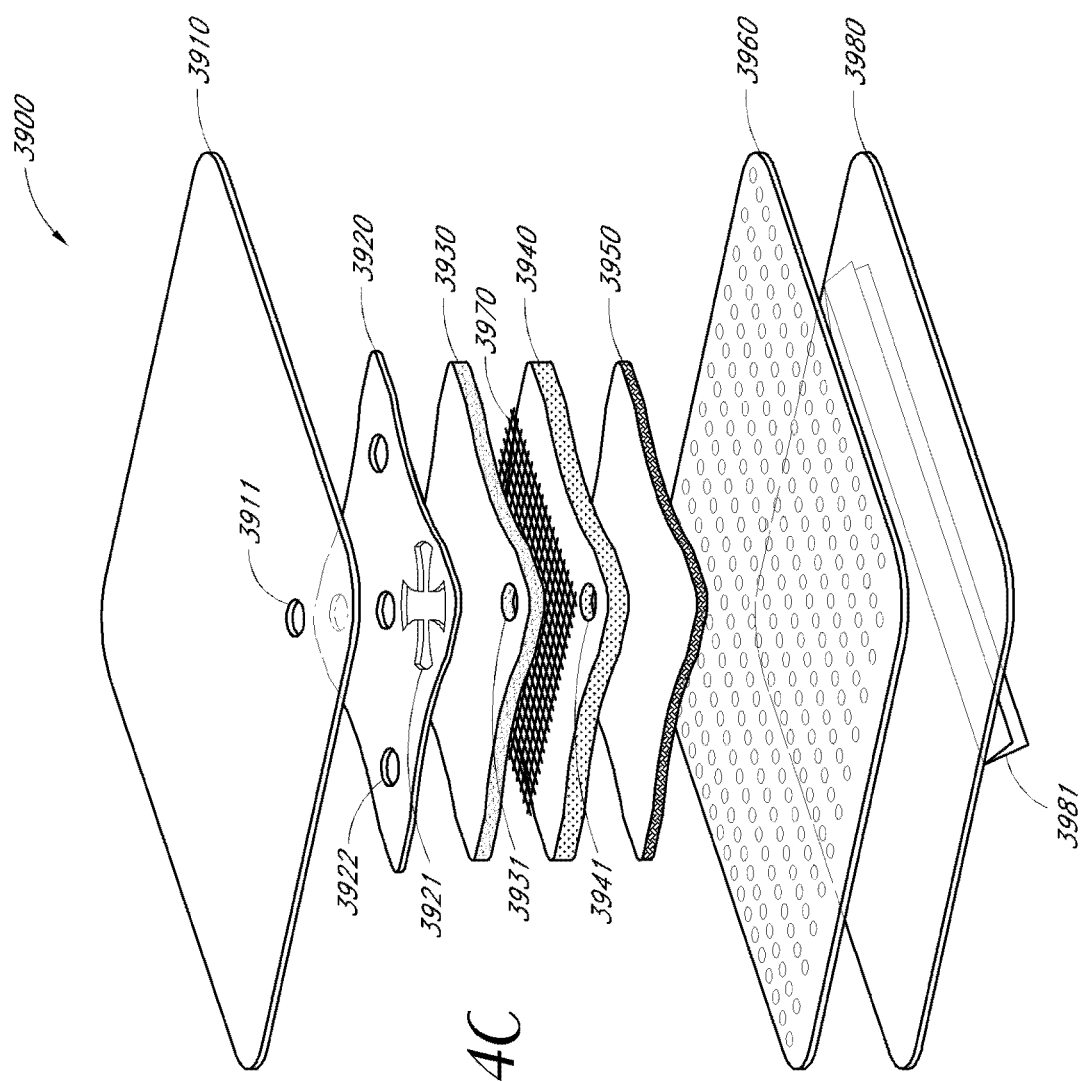

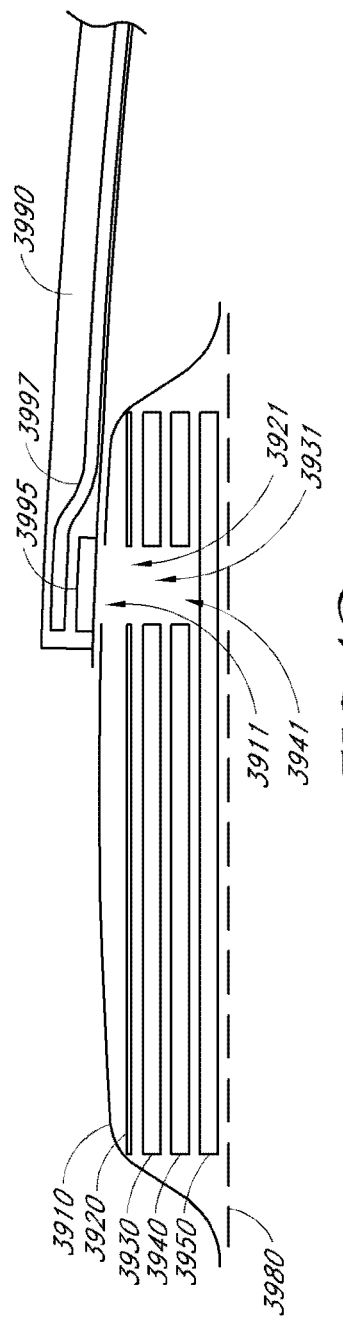

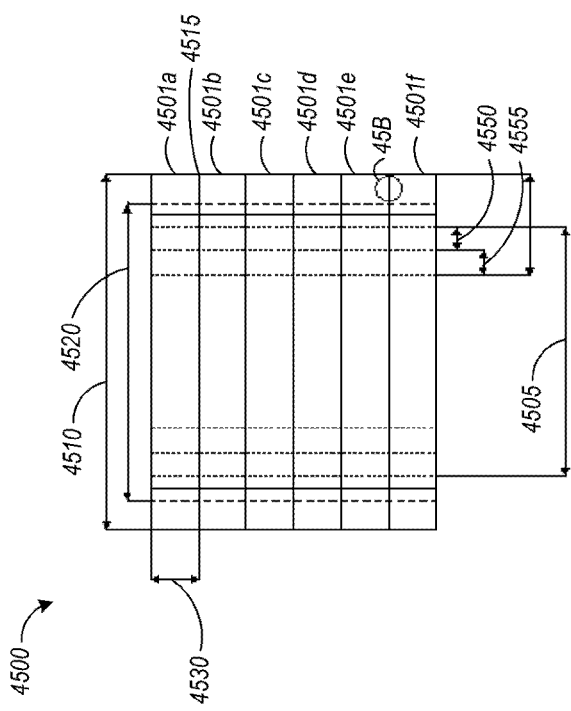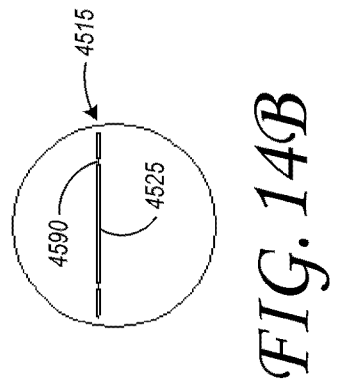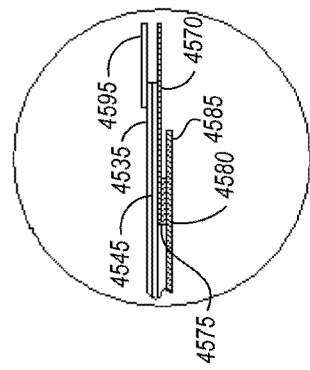

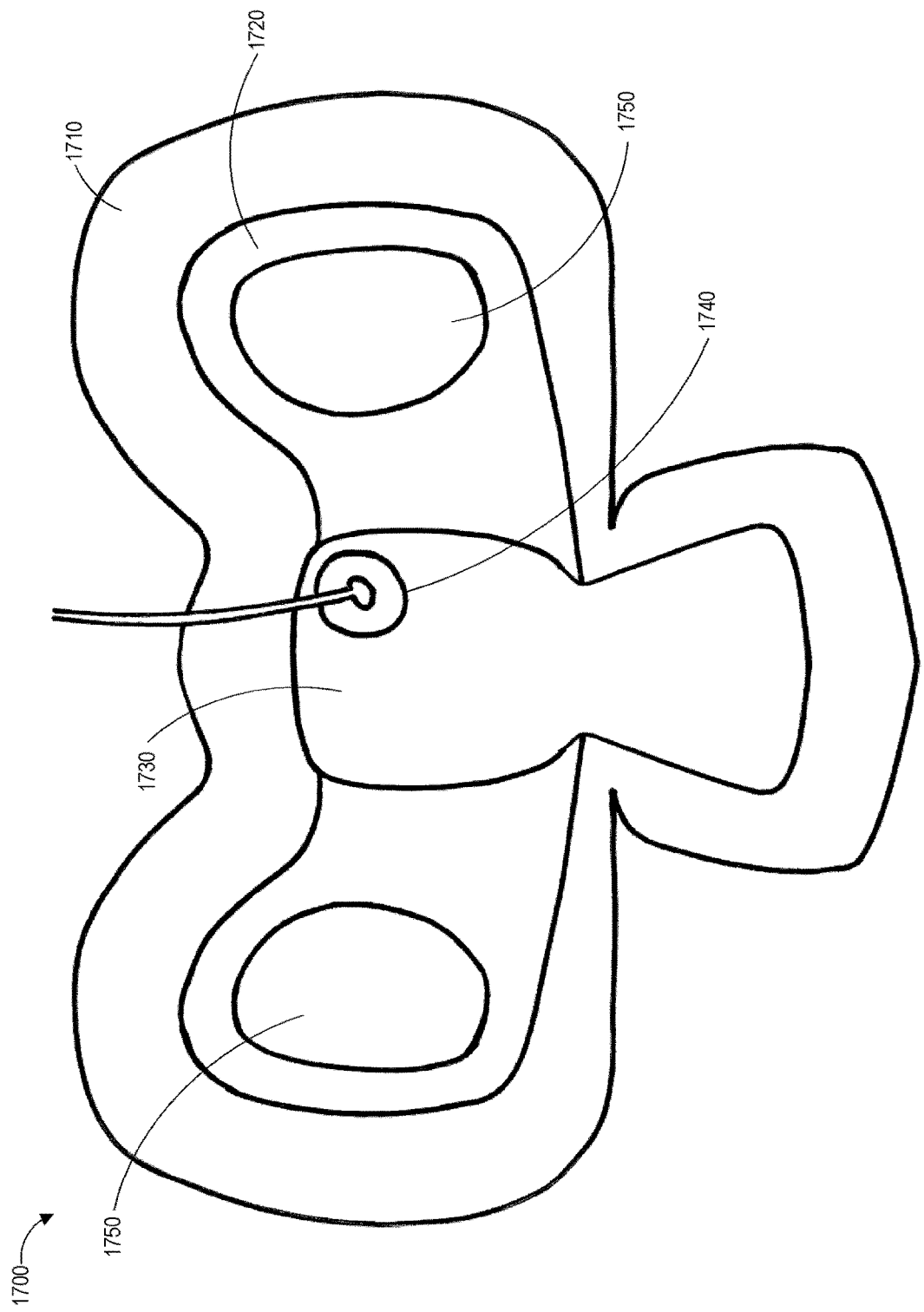

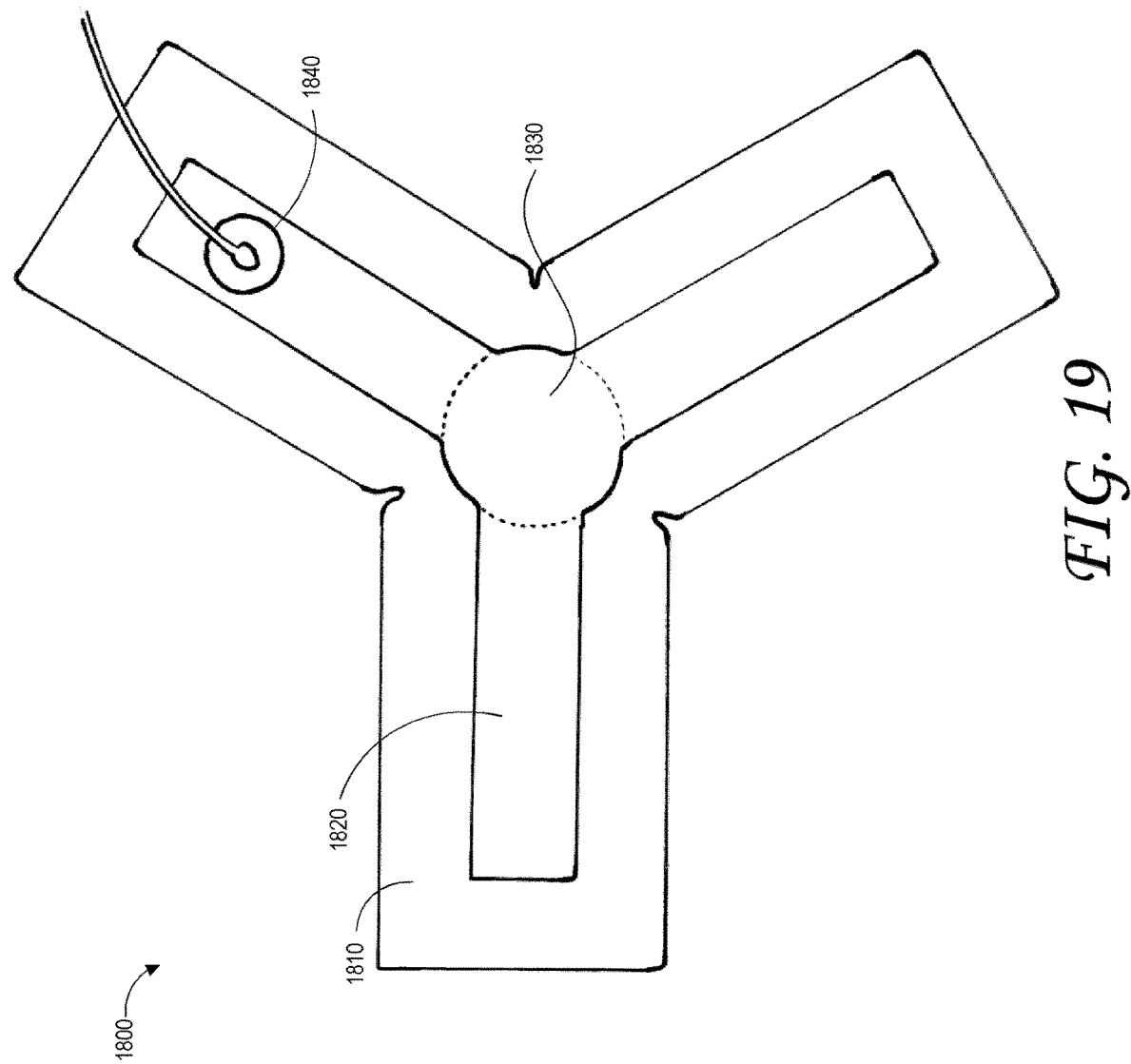

WOUND DRESSING AND METHOD OF TREATMENT

PRIORITY CLAIM AND INCORPORATION BY REFERENCE

This application is a continuation of U.S. application Ser. No. 16/698,050, filed Nov. 27, 2019, which is a continuation of U.S. application Ser. No. 14/775,494, filed Sep. 11, 2015, now issued as U.S. Pat. No. 10,493,184, issued Dec. 3, 2019, which is a national stage application of International Patent Application No. PCT/GB2014/050781, filed Mar. 14, 2014, which claims priority to U.S. Provisional Application Ser. No. 61/800,040, filed Mar. 15, 2013, titled "WOUND DRESSING AND METHOD OF TREATMENT," U.S. Provisional Application Ser. No. 61/828,604, filed May 29, 2013, titled "WOUND DRESSING AND METHOD OF TREATMENT," U.S. Provisional Application Ser. No. 61/829,187, filed May 30, 2013, titled "WOUND DRESSING AND METHOD OF TREATMENT," U.S. Provisional Application Ser. No. 61/906,865, filed Nov. 20, 2013, titled "WOUND DRESSING AND METHOD OF TREATMENT," and U.S. Provisional Application No. 61/907,350, filed Nov. 21, 2013, entitled "WOUND DRESSING AND METHOD OF TREATMENT," the entireties of each of which are hereby incorporated by reference. The embodiments disclosed in this application are also related to International Patent Application No. PCT/IB2013/002102, filed Jul. 31, 2013, titled "WOUND DRESSING AND METHOD OF TREATMENT, International Patent Application No. PCT/IB2013/002060, filed Jul. 31, 2013, titled "WOUND DRESSING AND METHOD OF TREATMENT, and U.S. Patent Publication No. 2011/0282309 A1, published Nov. 17, 2011, titled "WOUND DRESSING AND METHOD OF USE," the entireties of each of which are hereby incorporated by reference. Embodiments from the incorporated by reference applications may be interchanged and/or added to any of the embodiments disclosed herein.

FIELD OF THE INVENTION

Embodiments described herein relate generally to apparatuses, systems, and methods for the treatment of wounds, for example using dressings in combination with negative pressure wound therapy, and more particularly to apparatuses, systems, and methods for sizing a dressing for use in treating a wound.

SUMMARY OF THE INVENTION

Certain embodiments disclosed herein relate to improved wound dressings that exhibit enhanced adaptability. Such dressings may have advantages over prior art dressings which may be more difficult to apply, particularly around lengthy incision sites or irregularly shaped wounds. Also disclosed are improved methods of use and systems for use of the same, preferably in conjunction with negative pressure wound therapy.

Some embodiments of the dressings described herein may include a backing layer (also referred to herein as a wound cover or drape), that may be made of a gas impermeable membrane. As is used herein, the backing layer may be made of a gas impermeable membrane. Such dressings may also comprise one or more transmission layers and other layers (such as absorbent material) positioned beneath the backing layer. For example, one or more transmission layers or other layers may be positioned or enclosed between a backing layer and an optional wound contact layer, for example, sealed therebetween. The transmission layer(s) may be in turn positioned between the backing layer and (optional wound contact layer and) a wound site over which the dressing is configured to be positioned, for example sealed therebetween.

A transmission layer as described herein allows transmission of fluid such as air, and optionally additionally other gases and liquids, away from a wound site into upper layer(s) of the wound dressing. A transmission layer also ensures that an open air channel can be maintained to communicate negative pressure over the wound area even when the dressing is handling substantial amounts of exudates. The layer should remain open under the typical pressures that will be applied during negative pressure wound therapy. Preferably, a transmission layer remains open over an area corresponding to the wound site, and thereby ensures that the whole wound site sees an equalised negative pressure. Alternatively the transmission layer may comprise one or more specific air paths which remain open, such as in and between bridging portions of a wound dressing as described further below.

Some examples of materials suitable for a transmission layer include a three dimensional structure, for example, a knitted or woven spacer fabric (for example Baltex 7970 weft knitted polyester), although other materials such as foam (e.g., reticulated foam), nonwoven materials (e.g., an acquisition distribution layer as described below) could of course be used. Alternatively or additionally the transmission layer may incorporate absorbent material and absorb liquid drawn away from the wound under the applied negative pressure.

A transmission layer may comprise voids or may comprise one or more materials which transmit fluid, or may be a combination thereof. The transmission layer may incorporate other functional materials provided that it is still capable of transmitting negative pressure, and preferably also liquid fluids. In some embodiments, the transmission layer is capable of transmitting wound exudates and other compositions of matter.

Some embodiments described herein include a trimmable dressing, having a main dressing portion or cell in fluid (e.g., gas) communication with additional dressing portions or cells. One or more additional portions or cells may be removed to provide a dressing having a size or shape or profile or articulation which is to be compatible with a wound or wound site to be dressed. Preferably portions or cells may be retained to provide a large surface area, or an elongate main dressing portion is provided to dress a similarly large surface area or elongate wound, or portions or cells may be removed to dress a correspondingly reduced surface area or reduced length wound. Preferably one or more additional portions or cells may be conformed to provide a shaped dressing to dress a similarly shaped wound or to dress a wound incorporating or adjacent a protrusion such as a fixation device, for example a pin, or such as a body part such as a digit. Preferably one or more additional portions or cells may be conformed to provide a profiled dressing to dress a similarly profiled wound or wound site, such as a wound located on complex body topography. Preferably one or more additional portions or cells may be articulated to dress a similarly articulated wound or wound site such as a wound located on a joint.

A main dressing portion or portions and additional portions or cells as described herein may be connected by one or more bridge portions including one or more transmission layers as described above.

As is used herein, an exposed portion of transmission layer represents a portion at which the backing layer and optional wound contact layer do not enclose the transmission layer. For example, the backing layer may be partially absent, and additionally the optional wound contact layer may be partially absent, at which the transmission layer terminates in open-ended manner. It may be desired to seal such exposed portion of transmission layer (or exposed portions of other layers). As is used herein, sealing represents sealing in manner to contain fluid, more preferably in manner to contain negative pressure.

Exposed portion(s) as hereinbefore defined may be the result of removing a portion of the wound dressing, which may be by any envisaged means, for example cutting the wound dressing or tearing along a weakened line. Composite wound dressings may comprise a border for affixing around a wound, about a central wound contact portion. The dressings as hereinbefore defined may include a backing layer and wound contact layer of similar footprint or surface area to the transmission layer or other layers enclosed therebetween (i.e. a borderless dressing) or of greater footprint or surface area than the transmission layer enclosed therebetween (i.e. a bordered dressing). Exposed portion(s) as hereinbefore defined result from removing a portion of the wound dressing as hereinbefore defined directly enclosing the transmission layer or other layers, for example by cutting into or through the backing layer and wound contact layer and the transmission layer therebetween.

As is used herein, fluid represents liquid and gas. However it is not intended that "fluid" should encompass "vapour", a favourable moisture vapour transmission rate (MVTR) being a requirement of dressings envisaged herein. The backing layer is impermeable or substantially impermeable to fluids including wound exudate. The backing layer is air-tight or substantially air-tight, whereby a negative pressure may be maintained at a wound site to which the dressing is applied and sealed, for example with sealant, composition or adhesive material. Wound exudates and other fluids may be contained within the wound site and/or dressing and any collection means associated therewith.

As is used herein, a wound dressing may refer to a composite wound dressing, for example an advanced wound management dressing tailored to include specific wound therapy provision selected from management of wound exudates (e.g., ALLEVYN Gentle Border, DURAFIBER, ALLEVYN Life), infection management (e.g., ACTICOAT, IODOSORB), IV site care (e.g., IV3000), management of compromised skin about the wound, topical negative pressure ("TNP") (e.g., RENASYS F/AB, PICO, KCI Prevena, Kalypto Medical Inc. NPD1000 Negative Pressure Wound Therapy System), post-operative care such as surgical drapes (e.g., OPSITE), temporary bioskin dressings (e.g., BIOBRANE) and the like, most preferably a TNP dressing. For example, a dressing as described herein may be a wound dressing having a silicone (PDMS) wound contact surface, and is more preferably a TNP dressing. Known TNP dressings include: Smith & Nephew Disposable Kits for TNP such as Smith & Nephew, RENASYS-F/AB, Abdominal Dressing Kit; Smith & Nephew, RENASYS-F/P, Foam Dressing Kit With Port; Smith & Nephew, RENASYS-G, Gauze Dressing Kit; Smith & Nephew, PICO™ dressing kit; and KCI Kits for TNP including, V.A.C.™ GranuFoam Dressings Kits; and the like. Additional dressings and methods of treating wounds with negative pressure are disclosed in the following applications that are hereby incorporated by reference in their entireties: U.S. application Ser. No. 13/381,885, filed 30 Dec. 2011 and published as US2012/0116334; U.S. application Ser. No. 12/886,088, filed 20 Sep. 2010 and published as US2011/0213287; U.S. application Ser. No. 13/092,042, filed 21 Apr. 2011 and published as US2011/0282309; U.S. application Ser. No. 12/744,277, filed 20 Sep. 2010 and published as US2011/0028918; U.S. application Ser. No. 12/744,218, filed 20 Sep. 2010 and published as US2011/0054421; PCT Publication No. WO2011/000622; PCT Publication No. WO 2011/000621; PCT Publication No. WO2011/135285; PCT Publication No. WO2011/135286; U.S. Pat. Nos. 7,964,766, and 7,615,036

Embodiments of dressings described herein address the problem of providing dressings in a range of sizes and shapes to accommodate irregularly shaped wounds and body topography, for example vein harvest wound dressings accommodating variations in height and leg-length of individuals, which is impractical both to the manufacturer and to the user. Embodiments enhance adaptability of existing dressings, including more recently introduced multisite dressings such as trilobes and quadrilobes. Certain embodiments enable a portion of a dressing to be removed to create a main wound dressing of desired size or shape or profile or articulation, and sealing exposed portion(s) thereof to contain a negative pressure.

The portion(s) of the wound dressing may be removed to size the main wound dressing portion for positioning over a wound as hereinbefore defined, for example an incisional wound, an elongate leg wound, an arcuate incisional wound and the like. Similarly the portion(s) of the wound dressing may be removed to shape the main wound dressing portion for positioning over a wound as hereinbefore defined, such as a flap wound, over a protruding device such as a fixation device or a protruding body part, to profile the main wound dressing for positioning over a wound as hereinbefore defined, for example on complex body topography, or to articulate the main wound dressing for positioning over a wound as hereinbefore defined for example on a flexing joint.

In one embodiment, a wound treatment apparatus for treatment of a wound site comprises:

a backing layer having an upper surface and a lower surface, otherwise termed a backing sheet having two faces, and defining a perimeter configured to be positioned over skin surrounding a wound site;

one or more transmission layers configured to be positioned below the backing layer, or otherwise positioned at or on one side of one face of the backing layer, the one or more transmission layers comprising one or more bridging portions having a smaller width than adjacent portions of the one or more transmission layers; and a port configured to transmit negative pressure through the backing layer for the application of topical negative pressure at the wound site.

In some embodiments, an optional wound contact layer may be provided, with the one or more transmission layers positioned between the backing layer and the wound contact layer. The one or more transmission layers may be in direct or indirect contact with a lower surface of the backing layer. In some embodiments, the one or more transmission layers comprise a first layer comprising a spacer material configured to vertically wick fluid. The one or more transmission layers may further comprise a second layer comprising an acquisition distribution material configured to horizontally wick fluid, the second layer positioned above the first layer. One of the first layer and the second layer, or both, may be present in the one or more bridging portions. In other embodiments, the one or more transmission layers comprise an acquisition distribution material configured to horizontally wick fluid. In some embodiments, the port may comprise an opening in the backing layer. The port may comprise a port member attached to the backing layer over an opening in the backing layer. The port member may be sealed to the upper surface of the backing layer. Some embodiments may further comprise an absorbent material between the backing layer and the one or more transmission layers having a similar footprint to that of the one or more transmission layers. Absorbent material may be present or absent in the one or more bridging portions. Some embodiments of the one or more transmission layers may comprise an acquisition distribution material between the optional wound contact layer and the absorbent layer having a similar footprint to that of the absorbent material and/or absorbent layer. The one or more transmission layers may further comprise a spacer material configured to distribute negative pressure, the spacer material having a similar footprint to the acquisition distribution material, the spacer material configured to be positioned beneath the acquisition distribution material. The acquisition distribution material may be present or absent in the one or more bridging portions.

The one or more transmission layers may have a rectangular shape having a longitudinal axis extend along its length. The one or more transmission layers may comprise one or more bridging portions centered on the longitudinal axis. The one or more transmission layers may comprise three or more bridging portions centered on the longitudinal axis. The one or more bridging portions may also be offset from the longitudinal axis. The one or more bridging portions may have a width that is less than ⅓ the width of adjacent portions of the one or more transmission layers. The one or more bridging portions may have a width that is less than ¼ the width of adjacent portions of the one or more transmission layers. The one or more bridging portions may have a width that is less than ⅛ the width of adjacent portions of the one or more transmission layers. As is used herein, a smaller width represents a narrowing of or constriction in a transmission layer with respect to adjacent portions thereof. The one or more transmission layers may have a T-shape with a bridging portion on each leg of the T. The one or more transmission layers may have a T-shape with at least one bridging portion on each leg of the T. The one or more transmission layer may comprise a plurality of cells each separated by one or more bridging portions. The one or more transmission layer may comprise a plurality of cells, and wherein each of the plurality of cells is connected to at least one adjacent cell by one or more bridging portions, and wherein the one or more bridging portions may provide for gas communication between adjacent cells.

The wound treatment apparatus may be rolled into a tape which can be cut along the one or more bridging portions. Cutting along or across the bridging portions may sever adjacent cells.

In another embodiment, a wound treatment apparatus for treatment of a wound site comprises:
  a backing layer having an upper surface and a lower surface, otherwise termed a backing sheet having two faces, and defining a perimeter configured to be positioned over skin surrounding a wound site;
  one or more transmission layers configured to be positioned beneath the backing layer, or otherwise positioned at or on one side of one face of the backing layer; and
  a plurality of ports configured to transmit negative pressure spaced apart on the backing layer.

In some embodiments, the wound treatment apparatus further comprises an optional wound contact layer, with the one or more transmission layers positioned between the backing layer and the wound contact layer. The one or more transmission layers may be in direct or indirect contact with a lower surface of the backing layer. In some embodiments, the one or more transmission layer comprise a first layer of a spacer material configured to vertically wick fluid. The one or more transmission layers may further comprise a second layer of an acquisition distribution material configured to horizontally wick fluid, the second layer positioned above the first layer. In other embodiments, the one or more transmission layers comprise an acquisition distribution material configured to horizontally wick fluid. The wound treatment apparatus may be configured to be rolled into a tape. The plurality of ports each may comprise an opening in the backing layer covered with a releasable tab. The one or more transmission layers may comprise one or more bridging portions having a smaller width than adjacent portions of the one or more transmission layers. The plurality of ports are spaced apart lengthwise on the backing layer when the wound treatment apparatus is rolled into a tape. The wound treatment apparatus may be used in any desired length by cutting between adjacent ports.

Some embodiments may further comprise a fluidic connector configured to supply negative pressure to the port. Some embodiments may further comprise a source of negative pressure configured to supply negative pressure through the port. Negative pressure may be established at a wound site by means of any one of the plurality of ports, or by means of multiple ports of the plurality of ports, the remainder of which may remain sealed or may be removed with a section of dressing. Some embodiments may further comprise one or more separate or integral adhesive strips or sealing strips configured to seal the backing layer to skin surrounding a wound after the apparatus is cut along or across the one or more bridging portions. The strips may be comprised of backing layer material, such as polyurethane or hydrocolloid, or silicone based material such as OP SITE FLEXIFIX or OPSITE FLEXIFIX Gentle.

In another embodiment, a method of treating a wound, or of sizing a dressing for use in treating a wound, comprises:
  providing a wound dressing comprising:
    a backing layer; and
    one or more transmission layers positioned beneath the backing layer;
  removing a portion of the wound dressing to create a main wound dressing portion with one or more exposed portions;
  positioning the main wound dressing portion over a wound;
  sealing the main wound dressing to skin surrounding the wound, wherein sealing comprises sealing the one or more exposed portions of the main wound dressing portion; and
  optionally applying negative pressure to the wound through the backing layer of the main wound dressing portion.

In some embodiments of the method, the one or more transmission layers comprise one or more bridging portions having a smaller width than adjacent portions of the one or more transmission layers. In some embodiments, the one or more transmission layers comprise a first layer of a spacer material configured to vertically wick fluid. The one or more transmission layers may further comprise a second layer of an acquisition distribution material configured to horizontally wick fluid, the second layer positioned above the first layer. One of the first layer and the second layer, or both, may be present in one or more bridging portions. In other embodiments, the one or more transmission layers comprise an acquisition distribution material configured to horizontally wick fluid. A portion of the wound dressing may be removed along at least one of the one or more bridging portions. In some embodiments, removing a portion of the wound dressing comprises cutting the wound dressing across at least one of the one or more bridging portions. At least a portion of the wound dressing may comprise pre-cut score marks to facilitate removing of the portion of wound dressing. The dressing may comprise a plurality of openings in the backing layer covered with a releasable tab, and negative pressure may be applied to the backing layer through one of the openings. The dressing may comprise a plurality of openings in the backing layer covered with a releasable tab, and negative pressure may be applied to the backing layer through two or more of the openings. In some embodiments, the wound dressing further comprises an optional wound contact layer, wherein the transmission layer is positioned between the backing layer and the wound contact layer.

The portions of the wound dressing may be removed to size the main wound dressing portion for positioning over an incisional wound. The portions of the wound dressing may be removed to size the main wound dressing portion for positioning over an elongate leg wound. The portions of the wound dressing may be removed to size the main wound dressing portion for positioning over an arcuate incisional wound.

In another embodiment, a method of treating a wound, or for sizing a dressing for use in treating a wound, is provided, comprising:

providing a wound dressing comprising a backing layer, one or more transmission layers beneath the backing layer, and a plurality of spaced apart openings in the backing layer each covered with a releasable tab;

removing a portion of the wound dressing, the removed portion comprising at least one opening in the backing layer covered with a releasable tab;

positioning the removed portion of the wound dressing over a wound; and applying negative pressure through at least one opening in the backing layer after a releasable tab has been removed.

In further embodiments, the wound dressing may be configured into a roll, and the method may further comprise unrolling a portion of the wound dressing from the roll and removing a portion of the wound dressing from the roll.

In another embodiment, a wound treatment apparatus for treatment of a wound site comprises:

a backing layer having an upper surface and a lower surface, otherwise termed a backing sheet having two faces, and defining a perimeter configured to be positioned over skin surrounding a wound site;

one or more transmission layers configured to be positioned below the backing layer or otherwise positioned at or on one side of one face of the backing layer; and one or more ports configured to transmit negative pressure through the backing layer for the application of topical negative pressure at the wound site;

wherein the apparatus comprises a plurality of cells or regions separated by one or more trimmable portions.

This embodiment may incorporate features relating to previous embodiments hereinabove or hereinbelow. Trimmable portions may be selected from one or more bridging portions, as herein before or hereinbelow, and from portions intermediate multiple ports, each port corresponding to a separate negative pressure module.

In some embodiments, the plurality of cells forms a plurality of repeating negative pressure treatment modules. In one embodiment, one or more of the modules can be removed and the removed module(s) can subsequently be used to provide negative pressure to the wound site. In another embodiment, one or more modules can be removed and the remaining module(s) can subsequently be used to provide negative pressure to the wound site. In further embodiments, the trimmable portions may have a maximum width greater than or equal to the width of the absorbent pad portion, or otherwise 50 mm (or approximately 50 mm), 40 mm (or approximately 40 mm), 30 mm (or approximately 30 mm), 20 mm (or approximately 20 mm), or even 15 mm (or approximately 15 mm). In some embodiments, the trimmable portion may be from 10 mm to 20 mm (or approximately 10 mm to approximately 20 mm). In some embodiments, the cross-sectional area of a trimmable portion may be 2 $mm^2$ or approximately 2 $mm^2$, or more. The cross-sectional area can vary based on the transmission material used in the trimmable portion. Example materials having clinically appropriate transmission properties at various dimensions are described below with respect to FIGS. 15A-16C. The one or more trimmable portions may comprise one or more bridging portions having a smaller width as compared to the width of an adjacent cell or region. For example, the bridging portion may have a maximum width of ⅛, ¼, or ⅓ (or approximately ⅛, ¼, or ⅓) of a width of an adjacent cell or region. In some embodiments, the one or more transmission layers comprise a first layer of a spacer material configured to vertically wick fluid. The one or more transmission layers may further comprise a second layer of an acquisition distribution material configured to horizontally wick fluid, the second layer positioned above the first layer. One of the first layer and the second layer, or both, may be present in the one or more trimmable portions. In other embodiments, the one or more transmission layers comprise an acquisition distribution material configured to horizontally wick fluid. The plurality of cells or regions may comprise an absorbent material, the absorbent material positioned between the one or more transmission layers and the backing layer. The one or more trimmable portions may comprise an absorbent material, the absorbent material positioned between the one or more transmission layers and the backing layer. In other embodiments, no absorbent material is positioned between the one or more transmission layers and the backing layer. Some embodiments of the one or more transmission layers may comprise an acquisition distribution material having a similar footprint to the absorbent material, the acquisition distribution material configured to be positioned beneath the absorbent material. The one or more transmission layers may further comprise a spacer material configured to distribute negative pressure, the spacer material having a similar footprint to the acquisition distribution material, the spacer material configured to be positioned beneath the acquisition distribution material. The one or more transmission layers can comprise an open-cell reticulated foam. The one or more transmission layers can be configured to experience less than a threshold pressure differential across a length of the one or more transmission layers. The one or more transmission layers can be configured with a threshold level of resiliency, such that, after compression from an initial height, the one or more transmission layers returns to a threshold percentage of the initial height. The one or more transmission layers can be configured with a threshold level of resiliency, such that, after compression from an initial height, the one or more transmission layers returns to a threshold second height.

The one or more ports may each comprise an opening in the backing layer covered with a releasable tab, and negative pressure may be applied to the backing layer through at least one of the openings. Some embodiments may comprise multiple ports configured to transmit negative pressure through the backing layer, each port corresponding to a separate negative pressure treatment module. Some embodiments may further comprise a wound contact layer configured to be positioned beneath the one or more transmission layers, the wound contact layer further configured to seal to the backing layer around the perimeter.

In some embodiments, the plurality of cells may be approximately the same size, approximately square, and configured in a grid. In other embodiments, the plurality of cells may be configured in a T-shape. In other embodiments, the plurality of cells may be configured into a roll. In other embodiments, the plurality of cells may be configured in a linear arrangement. In some embodiments, each of the plurality of cells may be configured with one of the one or more ports. In other embodiments, at least two of the plurality of cells may be each configured with one of the one or more ports. The apparatus may further comprise a source of negative pressure connected to some or all of the one or more ports. In some embodiments, the dressing may comprise an exposed portion of one or more transmission layers. The exposed portion may be sealed with a sealant or adhesive material.

In another embodiment, a wound treatment apparatus for treatment of a wound site comprises:
   a backing layer having an upper surface and a lower surface, otherwise termed a backing sheet having two faces, and defining a perimeter configured to be positioned over skin surrounding a wound site;
   at least one absorbent pad portion comprising:
      an absorbent layer positioned below the backing layer or otherwise positioned at or on one side of one face of the backing layer, and
      one or transmission layers positioned below the absorbent layer or otherwise positioned at or on one side of one face of the absorbent layer;
   at least one trimmable bridging portion comprising the one or more transmission layers positioned below the backing layer.

Optionally, a wound contact layer may be positioned below the one or more transmission layers, wherein the wound contact layer is sealed to the backing layer along a perimeter of the backing layer and the wound contact layer. The trimmable bridging portion in some embodiments may also include a portion of absorbent layer. In other embodiments, no absorbent layer is present in the bridging portion. In some embodiments, a width of the one or more transmission layers in the bridging portion is less than a width of the one or more transmission layers in the absorbent pad portion. In other embodiments, the width of the one or more transmission layers in the bridging portion is the same as the width of the one or more transmission layers in the absorbent pad portion In another embodiment, a wound treatment apparatus for treatment of a wound site comprises:
   a backing layer having an upper surface and a lower surface, otherwise termed a backing sheet having two faces, and defining a perimeter configured to be positioned over skin surrounding a wound site;
   a first portion underneath the backing layer, or otherwise positioned at or on one side of one face of the backing layer, the first portion comprising at least one material layer configured to transmit negative pressure to the wound site; and
   a bridging portion underneath the backing layer, or otherwise positioned at or on one side of one face of the backing layer, the bridging portion comprising at least one material layer configured to transmit negative pressure from the first portion through the bridging portion.

The backing layer may be configured to maintain negative pressure over the wound site. In some embodiments, the at least one material layer in the bridging portion has a smaller dimension or a different material structure than a corresponding dimension or material structure of the first portion. Optionally, a wound contact layer may be positioned below the backing layer, wherein the wound contact layer is sealed to the backing layer along a perimeter of the backing layer.

In some embodiments, the at least one material layer of the first portion comprises one or more of a transmission layer such as reticulated open-cell foam, woven material, non-woven material, 3D knit fabric, Baltex 7970 weft knitted polyester, acquisition distribution material, DryWeb TDL2, SlimCore TL4, or the like. The at least one material of the first portion can additionally or alternatively comprise an absorbent layer, for example a superabsorbent pad comprising cellulose fibers and superabsorbent particles, MH460.101, ALLEVYN™ foam, Freudenberg 114-224-4, or Chem-Posite™ 11C-450. In some embodiments, the bridging portion comprises at least one material layer comprising one or more of reticulated open-cell foam, woven material, non-woven material, 3D knit fabric, Baltex 7970 weft knitted polyester, acquisition distribution material, DryWeb TDL2, SlimCore TL4, or the like. In some embodiments, the at least one material layer of the bridging portion should transmit a negative pressure of at least −40 mmHg against a set point in the range −60 to −200 mmHg with an air leak of 50 cc/minute. In some embodiments, the at least one material layer of the bridging portion should experience a pressure differential of approximately −25 mmHg or less (that is, closer to zero) at a set point of −200 mmHg with an air leak of 50 cc/minute over an approximately 20 mm±1 mm distance. In other embodiments, the at least one material layer of the bridging portion should experience a pressure differential of approximately −5 mmHg or less (that is, closer to zero) at a set point of −200 mmHg with an air leak of 50 cc/minute over an approximately 20 mm±1 mm distance. In some embodiments, the at least one material layer of the bridging portion has a height, in an uncompressed state, of at least 1 mm (or approximately 1 mm), at least 3 mm (or approximately 3 mm), at least 4 mm (or approximately 4 mm), or at least 5 mm (or approximately 5 mm), and a width of at least 1 mm (or approximately 1 mm), or at least 2 mm (or approximately 2 mm), at least 3 mm (or approximately 3 mm), at least 4 mm (or approximately 4 mm), or at least 5 mm (or approximately 5 mm). In some embodiments, the at least one material layer of the bridging portion has a maximum height, in an uncompressed state, of 9 mm (or approximately 9 mm) for purposes of being more easily re-sealable when cut. In some embodiments in which the dressing is sealed with a sealant, the at least one material layer can be resilient to compression such that a height of a sealed portion, in a compressed state, is substantially the same as the height of the sealed portion in an uncompressed state. In one embodiment, the at least one material layer of the bridging portion comprises a spacer material having a height of at least 2 mm (or approximately 2 mm) and a width of at least 1 mm (or approximately 1 mm). In one embodiment, the at least one material layer of the bridging portion comprises a reticulated open-cell foam having a height of at least approximately 5 mm and a width of at least approximately 3 mm, which, when wet, may experience a pressure differential of −8.9 (or approximately −8.9) mmHg. In another embodiment, the at least one material layer of the bridging portion comprises an acquisition distribution layer (e.g., SlimCore TL4) having a height of at least approximately 2 mm and a width of at least approximately 4 mm. Such dimensions can represent an uncompressed dimension of the material layer of the bridging portion. In one embodiment, the at least one material layer of the bridging portion is not compressible.

In some embodiments, the bridging portion comprises the same layer(s) as the first portion. In other embodiments, the bridging portion comprises fewer layers than the first portion. In some embodiments, the layer(s) in the bridging portion have a smaller width than the layer(s) in the first portion. In some embodiments, the layer(s) in the bridging portion have a dimension that is smaller than the layer(s) in the first portion (for example, the individual or combined height of the layer(s) in the bridging portion is smaller than the height of the layer(s) in the first portion. In other embodiments, the layer(s) in the bridging portion have the same width as the layer(s) in the first portion. In some embodiments, the bridging portion connects the first portion to an adjacent portion having a similar layered construction and/or width as the first portion. In some embodiments, there are multiple bridging portions that may connect a first portion to multiple adjacent portions, or may connect between multiple adjacent portions.

BRIEF DESCRIPTION OF THE DRAWINGS

FIG. 4A illustrates an exploded view of an embodiment of a wound dressing;

FIG. 4C illustrates another exploded view of an embodiment of a wound dressing;

FIG. 4D illustrates a cross sectional view of the wound dressing embodiment of FIG. 4C;

FIGS. 14A-14D illustrate one embodiment of a sealing strip assembly which may be used with a dressing and/or fluidic connector;

FIG. 18 illustrates an embodiment of a heel dressing;

FIG. 19 illustrates an embodiment of an extremity dressing;

DETAILED DESCRIPTION OF THE PREFERRED EMBODIMENTS

I. Introduction

Figure 1:
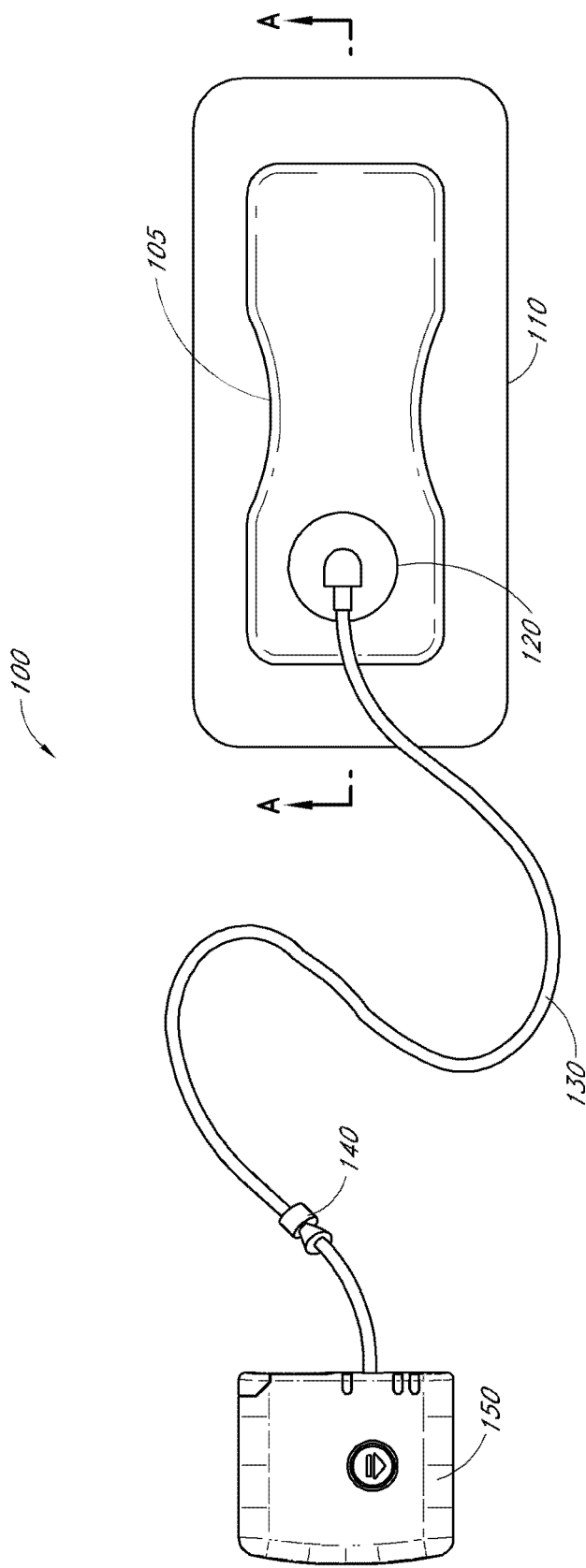
FIG. 1 illustrates an embodiment of a wound treatment system.

Embodiments disclosed herein relate to apparatuses and methods of treating a wound with reduced pressure, including pump and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, cosmetic wounds, trauma and venous ulcers or the like. Wounds may include readily accessible and difficult to access wounds, exposed and concealed wounds, large and small wounds, regular and irregular shaped wounds, planar and topographically irregular, uneven or complex wounds, more preferably on a site selected from the torso, limb and extremities such as heel, sacrum, axial, inguinal, shoulder, neck, leg, foot, digit, knee, axilla, arm and forearm, elbow, hand or for sealing a crevice adjacent or adjoining a wound site, selected from such as sacral cleft, fossar and the like.

It will be understood that embodiments of the present disclosure are generally applicable to use in topical negative pressure ("TNP") therapy systems. TNP therapy has sometimes been referred to as vacuum assisted closure V.A.C. or negative pressure wound therapy (NPWT), and is applicable to a broad range of wounds such as chronic wounds, incisional wounds, open wounds and abdominal wounds or the like. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability. During TNP therapy, a suction source such as a vacuum pump or the like is utilized to create a negative pressure region—that is to say, a region where an experienced pressure is below that of the surroundings. The suction source creates a negative pressure via a dressing or drape positioned over and sealed about or around the periphery of the wound. Wound exudate and other potentially harmful material is enclosed under the dressing or drape and extracted therefrom.

As is used herein, reduced or negative pressure levels, such as −X mmHg, represent pressure levels that are below standard atmospheric pressure, which corresponds to 760 mmHg (or 1 atm, 29.93 in HG, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less", "smaller" or "<" than −X mmHg corresponds to pressure that is closer to atmospheric pressure (e.g., −40 mmHg is less than −60 mmHg). Negative pressure that is "more", "greater" or ">" than −X mmHg corresponds to pressure that is further from atmospheric pressure (e.g., −80 mmHg is more than −60 mmHg). However, set point pressures may be referred to as positive in charts in the figures for purposes of generating chart data in a conventional format.

The negative pressure range for some embodiments of the present disclosure can be approximately −80 mmHg, or between about −20 mmHg and −200 mmHg. Note that these pressures are relative to normal ambient atmospheric pressure. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Canisterless NPWT (omitting a dedicated canister to contain wound exudate) has also been considered using negative pressure values in the same range as conventional NPWT, more preferably −40 to −200 mmHg, and more preferably −40 to −140 mmHg.

II. Overview of Example Systems

FIG. 1 illustrates an embodiment of a TNP wound treatment system 100 comprising a wound dressing 110 in combination with a pump 150. As stated above, the wound dressing 110 can be any wound dressing embodiment disclosed herein including without limitation dressing embodiment or have any combination of features of any number of wound dressing embodiments disclosed herein. Here, the dressing 110 may be placed over a wound as described previously, and a conduit 130 may then be connected to the port 120, although in some embodiments the dressing 101 may be provided with at least a portion of the conduit 130 preattached to the port 120. Preferably, the dressing 110 is provided as a single article with all wound dressing elements (including the port 120) pre-attached and integrated into a single unit. The wound dressing 110 may then be connected, via the conduit 130, to a source of negative pressure such as the pump 150. The pump 150 can be miniaturized and portable, although larger conventional pumps may also be used with the dressing 110. In some embodiments, the pump 150 may be attached or mounted onto or adjacent the dressing 110. A connector 140 may also be provided so as to permit the conduit 130 leading to the wound dressing 110 to be disconnected from the pump, which may be useful for example during dressing changes.

Figure 2A:
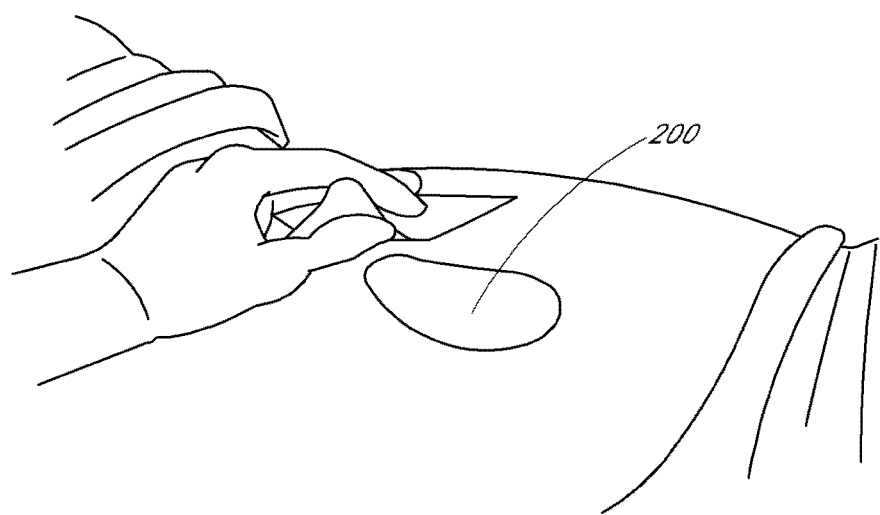
FIGS. 2A-2D illustrate the use and application of an embodiment of a wound treatment system onto a patient.

FIGS. 2A-2D illustrate the use of an embodiment of a TNP wound treatment system being used to treat a wound site on a patient. FIG. 2A shows a wound site 200 being cleaned and prepared for treatment. Here, the healthy skin surrounding the wound site 200 is preferably cleaned and excess hair removed or shaved. The wound site 200 may also be irrigated with sterile saline solution if necessary. Optionally, a skin protectant may be applied to the skin surrounding the wound site 200. If necessary, a wound packing material, such as foam or gauze, may be placed in the wound site 200. This may be preferable if the wound site 200 is a deeper wound.

Figure 2B:
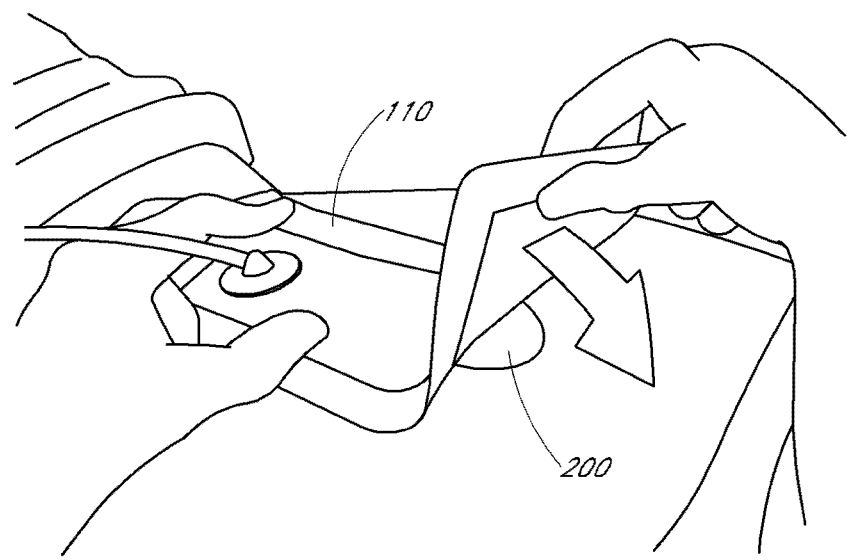

After the skin surrounding the wound site 200 is dry, and with reference now to FIG. 2B, the wound dressing 110 may be positioned and placed over the wound site 200. Preferably, the wound dressing 110 is placed with the wound contact layer 2102 over and/or in contact with the wound site 200. In some embodiments, an adhesive layer is provided on the lower surface 2101 of the wound contact layer 2102, which may in some cases be protected by an optional release layer to be removed prior to placement of the wound dressing 110 over the wound site 200. Preferably, the dressing 110 is positioned such that the port 2150 is in a raised position with respect to the remainder of the dressing 110 so as to avoid fluid pooling around the port. In some embodiments, the dressing 110 is positioned so that the port 2150 is not directly overlying the wound, and is level with or at a higher point than the wound. To help ensure adequate sealing for TNP, the edges of the dressing 110 are preferably smoothed over to avoid creases or folds.

Figure 2C:
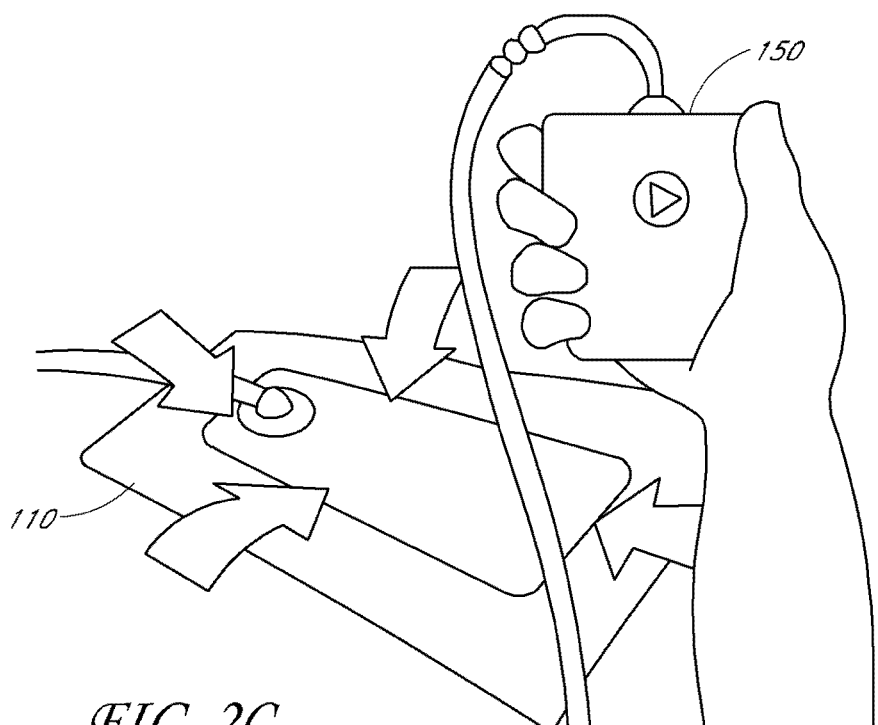

With reference now to FIG. 2C, the dressing 110 is connected to the pump 150. The pump 150 is configured to apply negative pressure to the wound site via the dressing 110, and typically through a conduit. In some embodiments, and as described above in FIG. 1, a connector may be used to join the conduit from the dressing 110 to the pump 150.

Upon the application of negative pressure with the pump 150, the dressing 110 may, in some embodiments, partially collapse and present a wrinkled appearance as a result of the evacuation of some or all of the air underneath the dressing 110. In some embodiments, the pump 150 may be configured to detect if any leaks are present in the dressing 110, such as at the interface between the dressing 110 and the skin surrounding the wound site 200. Should a leak be found, such leak is preferably remedied prior to continuing treatment.

Figure 2D:
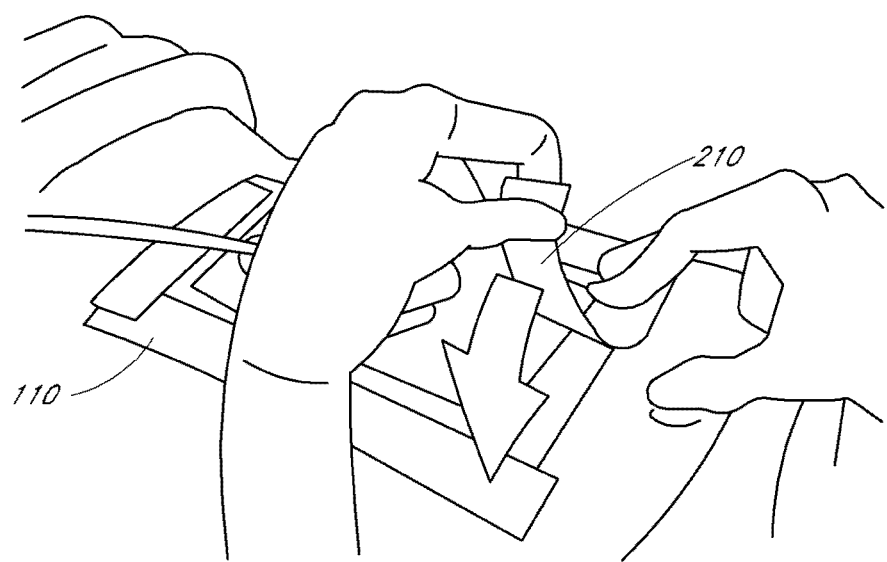

Turning to FIG. 2D, additional fixation strips 210 may also be attached around the edges of the dressing 110. Such fixation strips 210 may be advantageous in some situations so as to provide additional sealing against the skin of the patient surrounding the wound site 200. For example, the fixation strips 210 may provide additional sealing for when a patient is more mobile. In some cases, the fixation strips 210 may be used prior to activation of the pump 150, particularly if the dressing 110 is placed over a difficult to reach or contoured area.

Treatment of the wound site 200 preferably continues until the wound has reached a desired level of healing. In some embodiments, it may be desirable to replace the dressing 110 after a certain time period has elapsed, or if the dressing is full of wound fluids. During such changes, the pump 150 may be kept, with just the dressing 110 being changed.

III. Overview of Example Layers

Figure 3A:
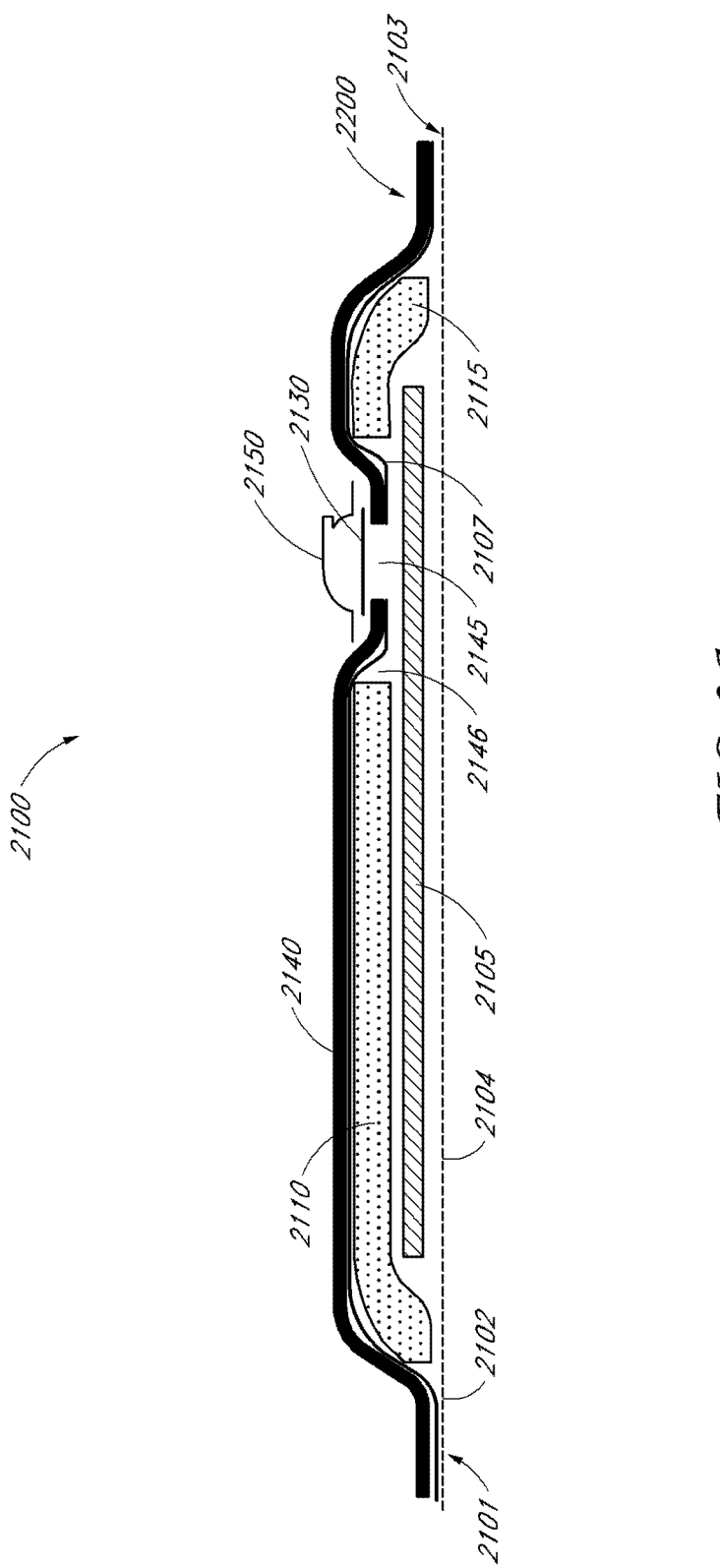
FIG. 3A illustrates an embodiment of a wound dressing in cross-section.
Figure 3B:
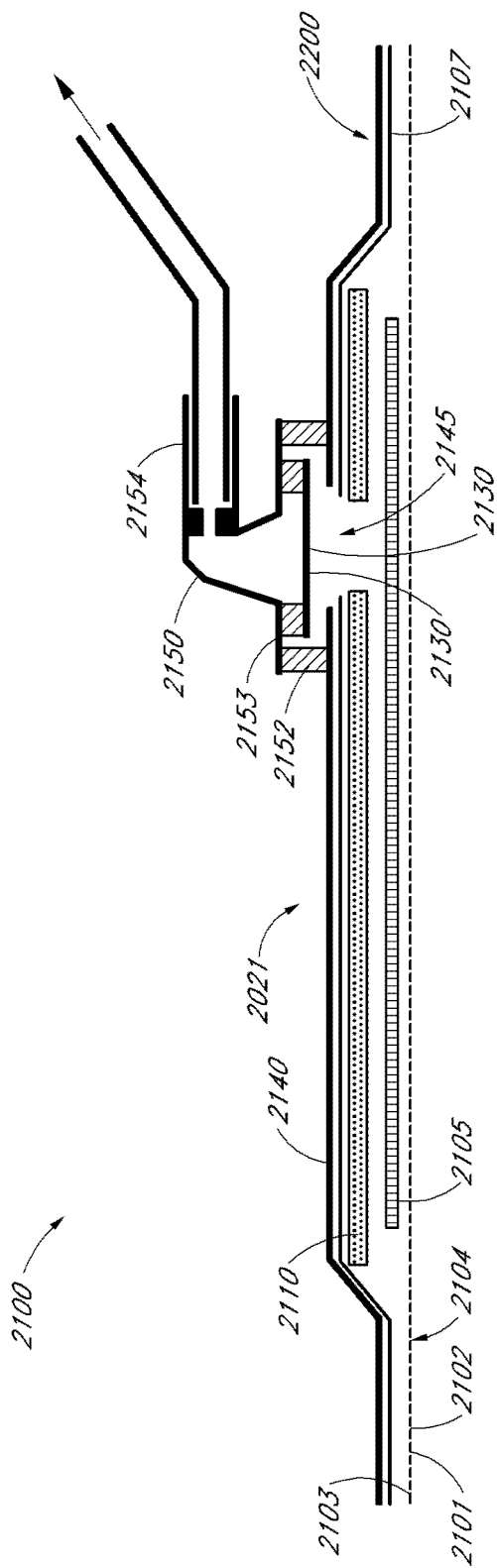
FIG. 3B illustrates another embodiment of a wound dressing in cross-section.
Figure 3C:
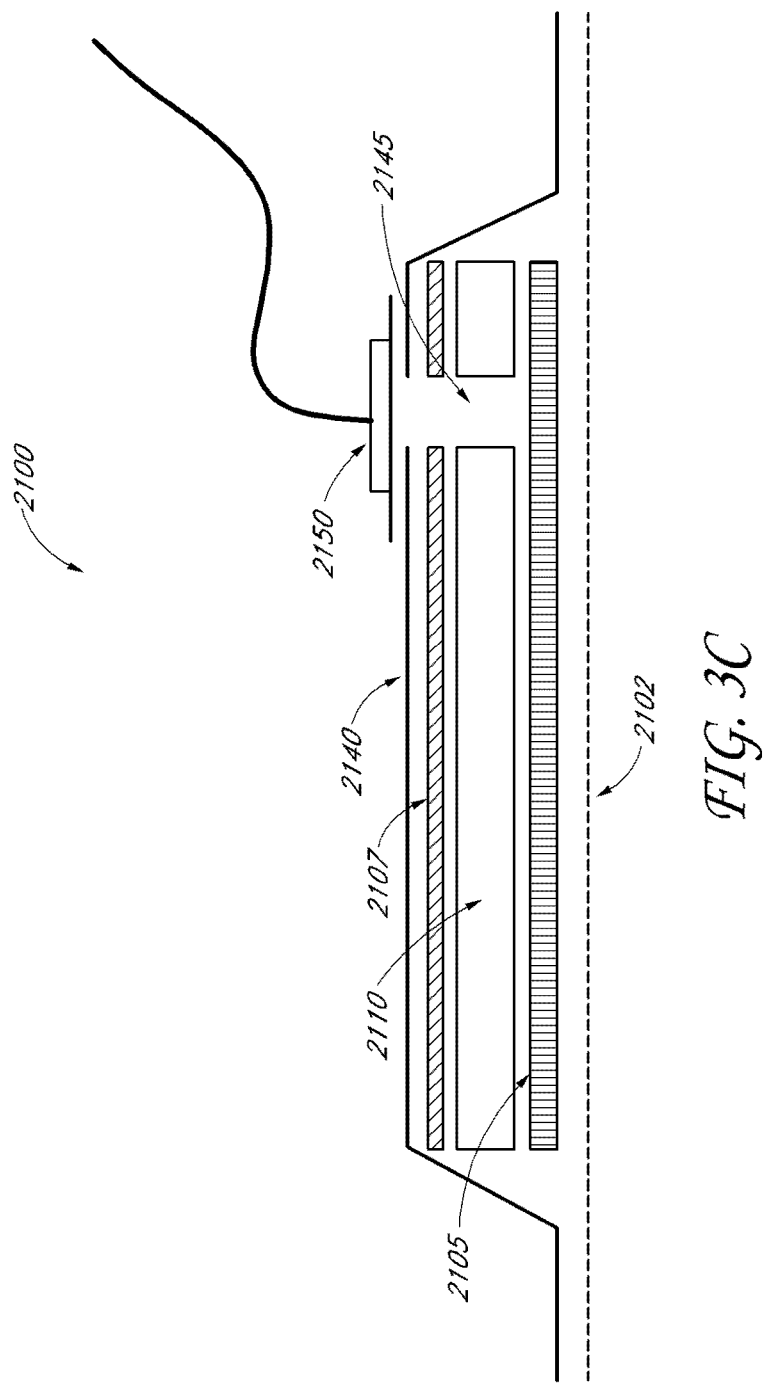
FIG. 3C illustrates another embodiment of a wound dressing in cross-section.

FIGS. 3A-3C illustrate cross-sections through a wound dressing 2100 similar to the wound dressing of FIG. 1 according to an embodiment of the disclosure. A view from above the wound dressing 2100 is illustrated in FIG. 1 with the line A-A indicating the location of the cross-section shown in FIGS. 3A and 3B. The wound dressing 2100, which can alternatively be any wound dressing embodiment disclosed herein including without limitation wound dressing 110 or any combination of features of any number of wound dressing embodiments disclosed herein, can be located over a wound site to be treated. The dressing 2100 may be placed to as to form a sealed cavity over the wound site. In a preferred embodiment, the dressing 2100 comprises a backing layer 2140 attached to a wound contact layer 2102, both of which are described in greater detail below. These two layers 2140, 2102 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 2105 and an absorbent layer 2110.

As illustrated in FIGS. 3A-3C, a lower surface 2101 of the wound dressing 2100 may be provided with an optional wound contact layer 2102. The wound contact layer 2102 can be a polyurethane layer or polyethylene layer or other flexible layer which is perforated, for example via a hot pin process, laser ablation process, ultrasound process or in some other way or otherwise made permeable to liquid and gas. The wound contact layer 2102 has a lower surface 2101 and an upper surface 2103. The perforations 2104 preferably comprise through holes in the wound contact layer 2102 which enable fluid to flow through the layer 2102. The wound contact layer 2102 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 2102 may help maintain the integrity of the entire dressing 2100 while also creating an air tight seal around the absorbent pad in order to maintain negative pressure at the wound.

Some embodiments of the wound contact layer 2102 may also act as a carrier for an optional lower and upper adhesive layer (not shown). For example, a lower pressure sensitive adhesive may be provided on the lower surface 2101 of the wound dressing 2100 whilst an upper pressure sensitive adhesive layer may be provided on the upper surface 2103 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 2100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 2105 of porous material can be located above the wound contact layer 2102. This porous layer, or transmission layer, 2105 allows transmission of fluid including liquid and gas away from a wound site into upper layers of the wound dressing. In particular, the transmission layer 2105 preferably ensures that an open air channel can be maintained to communicate negative pressure over the wound area even when the absorbent layer has absorbed substantial amounts of exudates. The layer 2105 should preferably remain open under the typical pressures that will be applied during negative pressure wound therapy as described above, so that the whole wound site sees an equalized negative pressure. The layer 2105 may be formed of a material having a three dimensional structure. For example, a knitted or woven spacer fabric (for example Baltex 7970 weft knitted polyester) or a non-woven fabric could be used.

A layer 2110 of absorbent material is provided above the transmission layer 2105. The absorbent material, which comprise a foam or non-woven natural or synthetic material, and which may optionally comprise a super-absorbent material, forms a reservoir for fluid, particularly liquid, removed from the wound site. In some embodiments, the layer 2100 may also aid in drawing fluids towards the backing layer 2140.

With reference to FIGS. 3A-3C, a masking or obscuring layer 2107 can be positioned beneath at least a portion of the backing layer 2140. In some embodiments, the obscuring layer 2107 can have any of the same features, materials, or other details of any of the other embodiments of the obscuring layers disclosed herein, including but not limited to having any viewing windows or holes. Additionally, the obscuring layer 2107 can be positioned adjacent to the backing layer, or can be positioned adjacent to any other dressing layer desired. In some embodiments, the obscuring layer 2107 can be adhered to or integrally formed with the backing layer. Preferably, the obscuring layer 2107 is configured to have approximately the same size and shape as the absorbent layer 2110 so as to overlay it. As such, in these embodiments the obscuring layer 2107 will be of a smaller area than the backing layer 2140.

The material of the absorbent layer 2110 may also prevent liquid collected in the wound dressing 2100 from flowing freely within the dressing, and preferably acts so as to contain any liquid collected within the absorbent layer 2110. The absorbent layer 2110 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 2110 may typically be manufactured from ALLEVYN™ foam, Freudenberg 114-224-4 and/or Chem-Posite™11C-450. In some embodiments, the absorbent layer 2110 may comprise a composite comprising superabsorbent powder, fibrous material such as cellulose, and bonding fibers. In a preferred embodiment, the composite is an airlaid, thermally-bonded composite.

An orifice 2145 is preferably provided in the backing layer 2140 to allow a negative pressure to be applied to the dressing 2100. A suction port 2150 is preferably attached or sealed to the top of the backing layer 2140 over an orifice 2145 made into the dressing 2100, and communicates negative pressure through the orifice 2145. A length of tubing 2220 may be coupled at a first end to the suction port 2150 and at a second end to a pump unit (not shown) to allow fluids to be pumped out of the dressing. The port may be adhered and sealed to the backing layer 2140 using an adhesive such as an acrylic, cyanoacrylate, epoxy, UV curable or hot melt adhesive. The port 2150 is formed from a soft polymer, for example a polyethylene, a polyvinyl chloride, a silicone or polyurethane having a hardness of 30 to 90 on the Shore A scale. In some embodiments, the port 2150 may be made from a soft or conformable material.

Preferably the absorbent layer 2110 and the obscuring layer 2107 include at least one through hole 2146 located so as to underlie the port 2150. The through hole 2146, while illustrated here as being larger than the hole through the obscuring layer 2107 and backing layer 2140, may in some embodiments be bigger or smaller than either. Of course, the respective holes through these various layers 2107, 2140, and 2110 may be of different sizes with respect to each other. As illustrated in FIGS. 3A-3C a single through hole can be used to produce an opening underlying the port 2150. It will be appreciated that multiple openings could alternatively be utilized. Additionally should more than one port be utilized according to certain embodiments of the present disclosure one or multiple openings may be made in the absorbent layer and the obscuring layer in registration with each respective port. Although not essential to certain embodiments of the present disclosure the use of through holes in the superabsorbent layer may provide a fluid flow pathway which remains unblocked in particular when the absorbent layer 2100 is near saturation.

The aperture or through-hole 2146 is preferably provided in the absorbent layer 2110 and the obscuring layer 2107 beneath the orifice 2145 such that the orifice is connected directly to the transmission layer 2105. This allows the negative pressure applied to the port 2150 to be communicated to the transmission layer 2105 without passing through the absorbent layer 2110. This ensures that the negative pressure applied to the wound site is not inhibited by the absorbent layer as it absorbs wound exudates. In other embodiments, no aperture may be provided in the absorbent layer 2110 and/or the obscuring layer 2107, or alternatively a plurality of apertures underlying the orifice 2145 may be provided.

The backing layer 2140 is preferably gas impermeable, but moisture vapor permeable, and can extend across the width of the wound dressing 2100. The backing layer 2140, which may for example be a polyurethane film (for example, Elastollan SP9109) or hydrocolloid film, having a pressure sensitive adhesive on one side, is impermeable to gas and this layer thus operates to cover the wound and to seal a wound cavity over which the wound dressing is placed. In this way an effective chamber is made between the backing layer 2140 and a wound site where a negative pressure can be established. The backing layer 2140 is preferably sealed to the wound contact layer 2102 in a border region 2200 around the circumference of the dressing, ensuring that no air is drawn in through the border area, for example via adhesive or welding techniques. The backing layer 2140 protects the wound from external bacterial contamination (bacterial barrier) and allows liquid from wound exudates to be transferred through the layer and evaporated from the film outer surface. The backing layer 2140 preferably comprises two layers; a polyurethane or hydrocolloid film and an adhesive pattern spread onto the film. The film is preferably moisture vapor permeable and may be manufactured from a material that has an increased water transmission rate when wet.

The absorbent layer 2110 may be of a greater area than the transmission layer 2105, such that the absorbent layer overlaps the edges of the transmission layer 2105, thereby ensuring that the transmission layer does not contact the backing layer 2140. This provides an outer channel 2115 of the absorbent layer 2110 that is in direct contact with the wound contact layer 2102, which aids more rapid absorption of exudates to the absorbent layer. Furthermore, this outer channel 2115 ensures that no liquid is able to pool around the circumference of the wound cavity, which may otherwise seep through the seal around the perimeter of the dressing leading to the formation of leaks.

As shown in FIG. 3A, one embodiment of the wound dressing 2100 comprises an aperture 2146 in the absorbent layer 2110 situated underneath the port 2150. In use, for example when negative pressure is applied to the dressing 2100, a wound facing portion of the port 150 may thus come into contact with the transmission layer 2105, which can thus aid in transmitting negative pressure to the wound site even when the absorbent layer 2110 is filled with wound fluids. Some embodiments may have the backing layer 2140 be at least partly adhered to the transmission layer 2105. In some embodiments, the aperture 2146 is at least 1-2 mm larger than the diameter of the wound facing portion of the port 2150, or the orifice 2145.

A filter element 2130 that is impermeable to liquids, but permeable to gases is provided to act as a liquid barrier, and to ensure that no liquids are able to escape from the wound dressing. The filter element may also function as a bacterial barrier. Typically the pore size is 0.2 µm. Suitable materials for the filter material of the filter element 2130 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the backing layer 2140 over the orifice 2145. For example, the filter element 2130 may be molded into the port 2150, or may be adhered to both the top of the backing layer 2140 and bottom of the port 2150 using an adhesive such as, but not limited to, a UV cured adhesive.

In FIG. 3B, an embodiment of the wound dressing 2100 is illustrated which comprises spacer elements 2152, 2153 in conjunction with the port 2150 and the filter 2130. With the addition of such spacer elements 2152, 2153, the port 2150 and filter 2130 may be supported out of direct contact with the absorbent layer 2110 and/or the transmission layer 2105. The absorbent layer 2110 may also act as an additional spacer element to keep the filter 2130 from contacting the transmission layer 2105. Accordingly, with such a configuration contact of the filter 2130 with the transmission layer 2105 and wound fluids during use may thus be minimized. As contrasted with the embodiment illustrated in FIG. 3A, the aperture 2146 through the absorbent layer 2110 and the obscuring layer 2107 may not necessarily need to be as large or larger than the port 2150, and would thus only need to be large enough such that an air path can be maintained from the port to the transmission layer 2105 when the absorbent layer 2110 is saturated with wound fluids.

With reference now to FIG. 3C, which shares many of the elements illustrated in FIGS. 3A-3B, the embodiment illustrated here comprises the backing layer 2140, masking layer 2107, and absorbent layer 2110, all of which have a cut or opening made therethrough which communicate directly to the transmission layer 2105 so as to form the orifice 2145. The suction port 2150 is preferably situated above it and communicates with the orifice 2145.

In particular for embodiments with a single port 2150 and through hole, it may be preferable for the port 2150 and through hole to be located in an off-center position as illustrated in FIGS. 3A-3C and in FIG. 1. Such a location may permit the dressing 2100 to be positioned onto a patient such that the port 2150 is raised in relation to the remainder of the dressing 2100. So positioned, the port 2150 and the filter 2130 may be less likely to come into contact with wound fluids that could prematurely occlude the filter 2130 so as to impair the transmission of negative pressure to the wound site.

FIG. 4A illustrates an exploded view of a dressing 3400 for use in negative pressure wound therapy, wherein the various layers are illustrated in an exploded view. Although this figure illustrates a dressing having one particular shape, the construction of the layers can be applied to any of the embodiments identified below, including FIG. 5A—FIG. 8, and any of the dressing shapes and configurations described in the patent applications incorporated by reference herein. The dressing 3400 comprises a release layer 3480, wound contact layer 3460, a spacer or transmission layer 3450, an acquisition distribution layer 3440 (which may also be considered a transmission layer) and which may optionally have an orifice located so as to underlie the suction port and align with the orifices in 3410 (labelled 3411), 3420 and 3430, an absorbent layer 3430, an obscuring layer 3420, and a backing layer 3410. The dressing 3400 may be connected to a port. At least the wound contact layer 3460, spacer layer 3450, absorbent layer 3430, obscuring layer 3420, and backing layer 3410 may have properties as described with respect to particular embodiments above, such as the embodiments of FIGS. 3A-3C, as well as or instead of the properties described below.

The dressing 3400 may comprise a wound contact layer 3460 for sealing the dressing 3400 to the healthy skin of a patient surrounding a wound area. Certain embodiments of the wound contact layer may comprise three layers: a polyurethane film layer, a lower adhesive layer and an upper adhesive layer. The upper adhesive layer may assist in maintaining the integrity of the dressing 3400, and the lower adhesive layer may be employed for sealing the dressing 3400 to the healthy skin of a patient around a wound site. As described above, in some embodiments with respect to FIGS. 3A-3C, some embodiments of the polyurethane film layer may be perforated. Some embodiments of the polyurethane film layer and upper and lower adhesive layers may be perforated together after the adhesive layers have been applied to the polyurethane film. In some embodiments a pressure sensitive adhesive, which may be a silicone, hot melt, hydrocolloid or acrylic based adhesive or other such adhesives, may be formed on both sides or optionally on a selected one side of the wound contact layer. In certain embodiments, the upper adhesive layer may comprise an acrylic pressure sensitive adhesive, and the lower adhesive layer may comprise a silicone pressure sensitive adhesive. In other embodiments the wound contact layer 3460 may not be provided with adhesive. In some embodiments, the wound contact layer 3460 may be transparent or translucent. The film layer of the wound contact layer 3460 may define a perimeter with a rectangular or a square shape. A release layer 3480 may be removably attached to the underside of the wound contact layer 3460, for example covering the lower adhesive layer, and may be peeled off using flaps 3481. Some embodiments of the release layer 3480 may have a plurality of flaps extending along the length of the layer 3480.

Some embodiments of the dressing 3400 may comprise a spacer layer 3450, which is one type of transmission layer that may be provided for communicating fluid through the dressing 3400. The spacer layer 3450 may comprise a porous material or 3D fabric configured to allow for the passage of fluids therethrough away from the wound site and into the upper layers of the dressing 3400. In particular, the spacer layer 3450 can ensure that an open air channel can be maintained to communicate negative pressure over the wound area even when the absorbent layer 3430 has absorbed substantial amounts of exudates. The spacer layer 3450 should remain open under the typical pressures that will be applied during negative pressure wound therapy as described above, so that the whole wound site sees an equalized negative pressure.

Some embodiments of the spacer layer 3450 may be formed of a material having a three dimensional structure. For example, a knitted or woven spacer fabric (for example Baltex 7970 weft knitted polyester) or a non-woven fabric can be used. In some embodiments, the spacer layer 3450 can have a 3D polyester spacer fabric layer. This layer can have a top layer which is a 84/144 textured polyester, and a bottom layer which can be a 100 denier flat polyester and a third layer formed sandwiched between these two layers which is a region defined by a knitted polyester viscose, cellulose or the like monofilament fiber. In use, this differential between filament counts in the spaced apart layers tends to draw liquid away from the wound bed and into a central region of the dressing 3400 where the absorbent layer 3430 helps lock the liquid away or itself wicks the liquid onwards towards the cover layer 3410 where it can be transpired. Other materials can be utilized, and examples of such materials are described in U.S. Patent Pub. No. 2011/0282309, which are hereby incorporated by reference and made part of this disclosure. However, the spacer layer 3450 may be optional, and for example may be optional in embodiments of the dressing 3400 which comprise the acquisition distribution layer 3440, described below.

Some embodiments may comprise a wicking or acquisition distribution layer (ADL) 3440. The ADL is another type of transmission layer that may be provided for communicating fluid through the dressing 3400. The ADL may be configured to horizontally wick fluid such as wound exudate as it is absorbed upward through the layers of the dressing 3400. Lateral wicking of fluid may allow maximum distribution of the fluid through the absorbent layer 3430 and may enable the absorbent layer 3430 to reach its full holding capacity. This may advantageously increase moisture vapor permeation and efficient delivery of negative pressure to the wound site. Some embodiments of the ADL 3440 may comprise viscose, polyester, polypropylene, polyethylene, cellulose (for example polysaccharide or repeated disaccharide), or a combination of some or all of these, and the material may be needle-punched. Some embodiments of the ADL 3440 may comprise polyethylene in the range of 40-150 grams per square meter (gsm). Some embodiments of the ADL may comprise a heavy fibrous melt material. Some embodiments of the ADL may be relatively porous to allow for the passage of fluids, including gas, therethrough. One example of an ADL may comprise a lightweight, felt-like, viscose material, which may be 80 gsm (or approximately 80 gsm). Some embodiments of the ADL may comprise cellulose in the range of 40-160 gsm (or about 40 to about 160 gsm), for example 80 (or about 80) gsm. The ADL may be constructed from a material which resists compression under the levels of negative pressure commonly applied during negative pressure therapy.

The dressing 3400 may further comprise an absorbent or superabsorbent layer 3430. The absorbent layer can be manufactured from ALLEVYN™ foam, Freudenberg 114-224-4 and/or Chem-Posite™11C-450, cellulose-based air-laid, or any other suitable material. In some embodiments, the absorbent layer 3430 can be a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid.

For example, some embodiments of the absorbent layer 3430 may comprise a layered construction of an upper layer of non-woven cellulose fibers, superabsorbent particles (SAP), and a lower layer of cellulose fibers with 40-80% SAP. In some embodiments, the absorbent layer 3430 may be an air-laid material. Heat fusible fibers can optionally be used to assist in holding the structure of the pad together. Some embodiments may combine cellulose fibers and air-laid materials, and may further comprise up to 60% SAP. Some embodiments may comprise 60% SAP and 40% cellulose. Other embodiments of the absorbent layer may comprise between 60% and 90% (or between about 60% and about 90%) cellulose matrix and between 10% and 40% (or between about 10% and about 40%) superabsorbent particles. For example, the absorbent layer may have about 20% superabsorbent material and about 80% cellulose fibers. It will be appreciated that rather than using super-absorbing particles or in addition to such use, super-absorbing fibers can be utilized according to some embodiments of the present invention. An example of a suitable material is the Product Chem-Posite™ 11 C-450 available from Emerging Technologies Inc (ETi) in the USA.

Super-absorber particles/fibers can be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc. The absorbent layer 3430 can have one or more through holes 3431 located so as to underlie the suction port.

Some embodiments of the present disclosure may optionally employ a masking or obscuring layer 3420 to help reduce the unsightly appearance of a dressing 3400 during use due to the absorption of wound exudate. The obscuring layer 3420 may be a colored portion of the absorbent material, or may be a separate layer that covers the absorbent material. The obscuring layer 3420 may be one of a variety of colors such as blue, orange, yellow, green, or any color suitable for masking the presence of wound exudate in the dressing 3400. For example, a blue obscuring layer 3420 may be a shade of blue similar to the shade of blue commonly used for the material of medical gowns, scrubs, and drapes. Some embodiments of the obscuring layer 3420 may comprise polypropylene spunbond material. Further, some embodiments of the obscuring layer 3420 may comprise a hydrophobic additive or coating. Other embodiments may comprise a thin fibrous sheet of 60, 70, or 80 gsm.

The obscuring layer may comprise at least one viewing window 3422 configured to allow a visual determination of the saturation level of the absorbent layer. The at least one viewing window 3422 may comprise at least one aperture made through the obscuring layer. The at least one viewing window 3422 may comprise at least one uncolored region of the obscuring layer. Some embodiments of the obscuring layer may comprise a plurality of viewing windows or an array of viewing windows.

The masking capabilities of the obscuring layer 3420 should preferably only be partial, to allow clinicians to access the information they require by observing the spread of exudate across the dressing surface. A obscuring layer 3420 may be partial due to material properties allowing wound exudate to slightly alter the appearance of the dressing or due to the presence of at least one viewing window 3422 in a completely obscuring material. The partial masking nature of the obscuring layer 3420 enables a skilled clinician to perceive a different colour caused by exudate, blood, by-products etc. in the dressing allowing for a visual assessment and monitoring of the extent of spread across the dressing. However, since the change in colour of the dressing from its clean state to a state with exudate contained is only a slight change, the patient is unlikely to notice any aesthetic difference. Reducing or eliminating a visual indicator of wound exudate from a patient is likely to have a positive effect on their health, reducing stress for example.

The obscuring layer 3420 can have one or more through holes located so as to underlie the suction port. Some embodiments may have a maltese cross 3421 or other shaped cutout underlying the suction port, wherein the diameter of the maltese cross 3421 is greater than the diameter of the port. This may allow a clinician to easily asses the amount of wound exudate absorbed into the layers beneath the port.

The dressing 3400 may also comprise a backing layer, or cover layer 3410 extending across the width of the wound dressing. The cover layer 3410 may be gas impermeable but moisture vapor permeable. Some embodiments may employ a polyurethane film (for example, Elastollan SP9109) or any other suitable material. For example, certain embodiments may comprise translucent or transparent 30 gsm EU33 film (from Smith & Nephew Extruded Films). The cover layer 3410 may have a pressure sensitive adhesive on the lower side, thereby creating a substantially sealed enclosure over the wound in which negative pressure may be established. The cover layer can protect the wound as a bacterial barrier from external contamination, and may allow liquid from wound exudates to be transferred through the layer and evaporated from the film outer surface.

The cover layer 3410 can have an orifice 3411 located so as to underlie the suction port. The orifice 3411 may allow transmission of negative pressure through the cover layer 3410 to the wound enclosure. The port may be adhered and sealed to the cover film using an adhesive such as an acrylic, cyanoacrylate, epoxy, UV curable or hot melt adhesive. Some embodiments may have a plurality of orifices for the attachment of multiple ports or other sources of negative pressure or other mechanisms for distributing fluid.

Figure 4B:
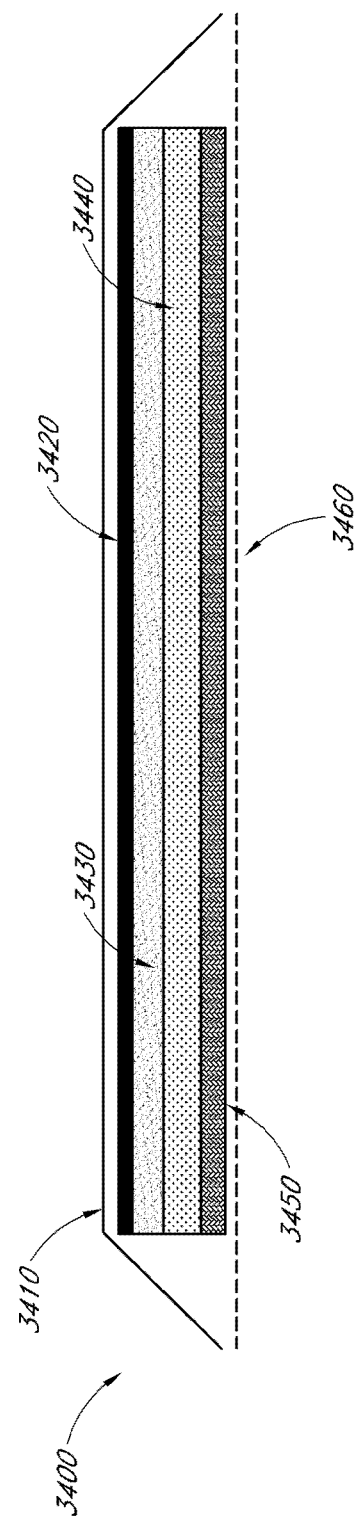
FIG. 4B illustrates a cross sectional view of an embodiment of a wound dressing.

FIG. 4B illustrates a cross sectional view of the wound dressing 3400, displaying an embodiment of the relative thicknesses of layers of the dressing 3400. In some embodiments, the wound contact layer 3460 may be flat and the top film layer 3410 may be contoured over the inner layers of the dressing 3400. The spacer layer 3450 may be half as thick as the acquisition distribution layer 3440 in some embodiments. In some embodiments, the absorbent layer 3430 may be about 1.5 times thicker than the spacer layer 3450. The obscuring layer 3420 may be about half the thickness of the spacer layer 3450.

FIG. 4C illustrates another embodiment of a wound dressing 3900, with the various layers illustrated in an exploded view. Although this figure illustrates a dressing having one particular shape, the construction of the layers can be applied to any of the embodiments identified below, including FIG. 5A-FIG. 8, and any of the dressing shapes and configurations described in the patent applications incorporated by reference herein. The wound dressing may comprise a release layer 3980, wound contact layer 3960, a transmission layer 3950, an acquisition distribution layer 3940, an adhesive layer 3970, an absorbent layer 3930, an obscuring layer 3920, and a backing layer 3910. At least the wound contact layer 3960, transmission layer 3950, absorbent layer 3930, obscuring layer 3920, and backing layer 3910 may have properties as described with respect to particular embodiments above, such as the embodiments of FIGS. 3A-3C, as well as or instead of the properties described below.

The dressing 3900 may be connected to a port 3990, as illustrated in FIG. 4D (shown without the release layer 3980). At least the backing layer 3910, obscuring layer 3920, absorbent layer 3930, and acquisition distribution layer 3940 may have openings underlying the port 3990, and the port 3990 may comprise a three-dimensional fabric 3997 and a filter element 3995 overlying the openings. In some embodiments, the opening 3921 in the obscuring layer may be cross-shaped. As illustrated, the cross-shaped opening 3921 may comprise four arms of roughly equal length extending outward from a central point of intersection of the arms, wherein the sides of each arm are angled or arced such that the far end of each arm is wider than the end closest to the intersection. The far ends of the four arms may comprise arcs, for example four arcs from a single circle, giving the cross a rounded shape. The opening 3911 in the backing layer 3910, opening 3931 in the absorbent layer 3930, and opening 3941 in the acquisition distribution layer 3940 may be aligned with the central intersection point of the cross-shaped opening 3921. The openings 3911, 3931, and 3941 may be the same size or of varying sizes.

The backing layer 3910 (as well as the backing layer of previously described embodiments) may comprise, in some embodiments, EU33 film and may optionally have a pressure-sensitive adhesive provided on a lower surface thereof. For example, the adhesive may be a water dispersible acrylic adhesive, for example K5. The adhesive may be able to be pattern spread, and may be hydrophilic.

The obscuring layer 3920 may be provided to increase patient comfort by masking the presence of wound exudate absorbed by the inner layers of the dressing. The obscuring layer 3920 may have an outer perimeter that is spaced 1 mm, or approximately 1 mm, or 0.5 mm to 3 mm, or approximately 0.5 to approximately 3 mm, beyond the adjacent perimeter edge of the dressing layer or layers provided beneath it, for example the absorbent layer 3930, ADL 3940, and/or transmission layer 3950. The obscuring layer 3920 may be provided with a plurality of viewing windows 3922 which may be used to assess the spread of exudate across the dressing 3900. The cross-shaped opening 3921 may be used as a viewing window to ascertain the level of saturation of the layer or layers underlying an attached port. The width of the cross-shaped opening 3921 may be greater than the width of an attached port to enable such assessment. Some embodiments of the obscuring layer 3920 (including other embodiments of the obscuring layer previously described) may comprise polypropylene spunbond material of suitable colors such as described above, including medical blue. Further, some embodiments of the obscuring layer 3920 may comprise a hydrophobic additive or coating.

The absorbent layer 3930 may be configured to absorb and retain exudate from a patient's wound. The absorbent layer 3930 will preferably be constructed from a material which has good absorbent qualities under negative pressure. In some embodiments (including any of the earlier described embodiments), the absorbent layer may comprise cellulose fibers or air-laid materials. Some embodiments may comprise a cellulose fibers with 40-80% superabsorbent particles (SAP), for example 40%-60% (or about 40% to about 60%) SAP or 60%-80% (or about 60% to about 80%) SAP. Heat fusible fibers can optionally be used to assist in holding the structure of the absorbent pad together. Some embodiments may combine cellulose fibers and air-laid materials, for example as a hybrid bonded airlaid composite in the range of 400-500 gsm (or about 400 to about 500 gsm), for example 460 (or about 460) gsm. The absorbent layer 3930 may include polyacrylate superasorber powder to increase the absorbent capabilities of the material. Some embodiments of the absorbent layer 3930 comprise a tissue dispersant layer. This may, in some embodiments, be provided along the lower surface of the layer, resulting in an asymmetric construction of the absorbent layer. The tissue dispersant layer may comprise a heat fusible binder to aid in holding the layer structure together. The tissue dispersant layer may provide the advantage of enabling fluid transport. In some embodiments, the tissue dispersant layer may comprise a hot melt adhesive such as ethylene vinyl acetate (EVA), for example applied as a solution to cellulose fibers of the absorbent layer.

The adhesive layer 3970 may bond an upper surface of the acquisition distribution layer 3940 to a lower surface of the absorbent layer 3930. As illustrated, in some embodiments the adhesive layer 3970 may comprise an adhesive web or net, for example a fusible web such as Wonder-Web®. In other embodiments, the adhesive layer 3970 may comprise adhesive tape, for instance strips or mesh of double sided adhesive film. In yet other embodiments the acquisition distribution layer 3940 and the absorbent layer 3930 may be heat laminated. Some embodiments may employ a hot melt adhesive, such as ethylene vinyl acetate (EVA). For example, EVA hot melt adhesive powder may be sprinkled over the ADL 3940, which may then be heat bonded (heat laminated) to the absorbent layer 3930. In some embodiments the acquisition distribution layer 3940 and the absorbent layer 3930 may be stitched or sewn together, and the adhesive layer 3970 may comprise suitable fibers, strands, or threads. In some embodiments of a trimmable dressing 3900, other layers may be bonded together in a similar manner to provide consistency with respect to layer alignment when the dressing is cut on one or more sides, such that the layers remain together when the sides of the dressing are cut, and such that there is not vertical separation of the layers at the cut portions. Preferred embodiments of the adhesive layer 3970 are hydrophilic so as not to affect the transport of water and/or water-based solutions between the acquisition distribution layer 3940 and absorbent layer 3930. In some embodiments, the adhesive layer may comprise a fine sprinkle of adhesive powder such that the acquisition distribution layer 3940 and absorbent layer 3930 are not bonded together across the entire upper and lower surfaces, respectively, but may be merely tacked together in a number of locations. However, some embodiments of the dressing may be constructed without the use of an adhesive between the acquisition distribution layer 3940 and absorbent layer 3930.

The acquisition distribution layer (ADL) 3940 may be constructed so as to advantageously horizontally wick fluid, such as wound exudate, as it is absorbed upward through the layers of the dressing 3900. Such lateral wicking of fluid may allow maximum distribution of the fluid through the absorbent layer 3930, enabling the absorbent layer 3930 to reach its full holding capacity. Some embodiments of the ADL 3940 (including any embodiments of the ADL previously described) may comprise cellulose in the range of 40-160 gsm (or about 40 to about 160 gsm), for example 80 (or about 80) gsm. The ADL may be constructed from a material which resists compression under the levels of negative pressure commonly applied during negative pressure therapy. The acquisition distribution layer (ADL) 3940 may be constructed so as to advantageously vertically wick fluid, such as wound exudate. Facilitating rapid movement of wound exudate from the transmission layer to the absorbent layer is desirable. Additionally judicious choice of material can reduce re-wetting of liquid from the absorbent layers down into lower layers, this phenomenon is known as "back wetting" or "re-wetting". Suitable materials that show an enhancement of this effect include Slimcore TL4 (150 gsm) from Libeltex BVBA or equivalent.

Some embodiments of the acquisition distribution layer (ADL) 3940 may include several internal layers. For example, one material suitable for use as an ADL includes a lower wicking or acquisition layer comprising substantially vertically extending fibers for vertical wicking of fluid and further includes an upper distribution layer comprising substantially horizontally extending fibers for horizontal wicking of fluid. Some ADL materials can include three or more layers, for example a lower wicking layer and two upper distribution layers. Other configurations can have one or more distribution layers positioned between upper and lower acquisition layers.

Some embodiments of the dressing 3900 may optionally comprise a spacer or transmission layer 3950. The transmission layer 3950 may comprise a porous material or 3D fabric configured to allow for the passage of fluids therethrough away from the wound site and into the upper layers of the dressing 3900. In particular, the transmission layer 3950 should remain open under the typical pressures that will be applied during negative pressure wound therapy as described above, so that the whole wound site sees an equalized negative pressure. In some embodiments, the acquisition distribution layer 3940 may be sufficient to maintain even transmission of negative pressure throughout the dressing 3900 and the transmission layer 3950 may be excluded. An outer perimeter of the transmission layer may be spaced 5 mm, or approximately 5 mm, or 2 mm to 8 mm, or approximately 2 mm to approximately 8 mm, inward of the adjacent perimeter edge of the dressing layer positioned above the transmission layer, for example the ADL 3940 or absorbent layer 3930.

The dressing 3900 may optionally comprise a wound contact layer 3960 for sealing the dressing 3900 to the healthy skin of a patient surrounding a wound area. As discussed above with respect to FIG. 4A, the wound contact layer 3960 may comprise flexible polyurethane film, and may be provided with a silicone adhesive on a lower surface thereof. The wound contact layer 3960 may be perforated to allow for the transmission of fluids such as wound exudate therethrough, so that the fluids may be passed through or retained by the inner layers of the dressing 3900. Prior to use, the wound contact layer 3960 may be protected by a protective release layer 3980, which may be provided with at least one set of flaps 3981 for removing or peeling off the release layer 3980.

IV. Overview of Example Dressing and Bridge Configurations

Figure 5A:
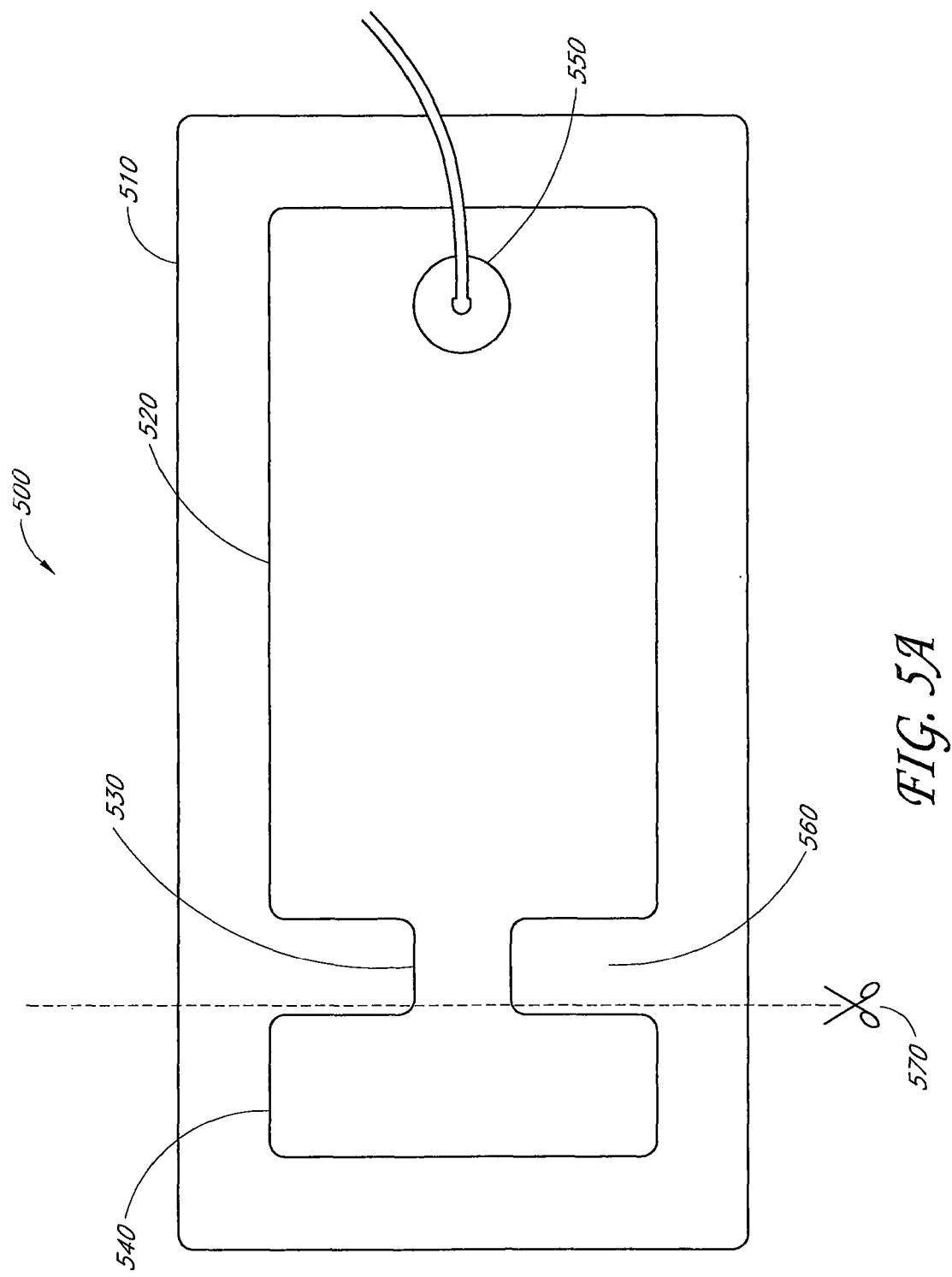
FIG. 5A illustrates an embodiment of a wound dressing trimmable at a bridge portion.
Figure 5B:
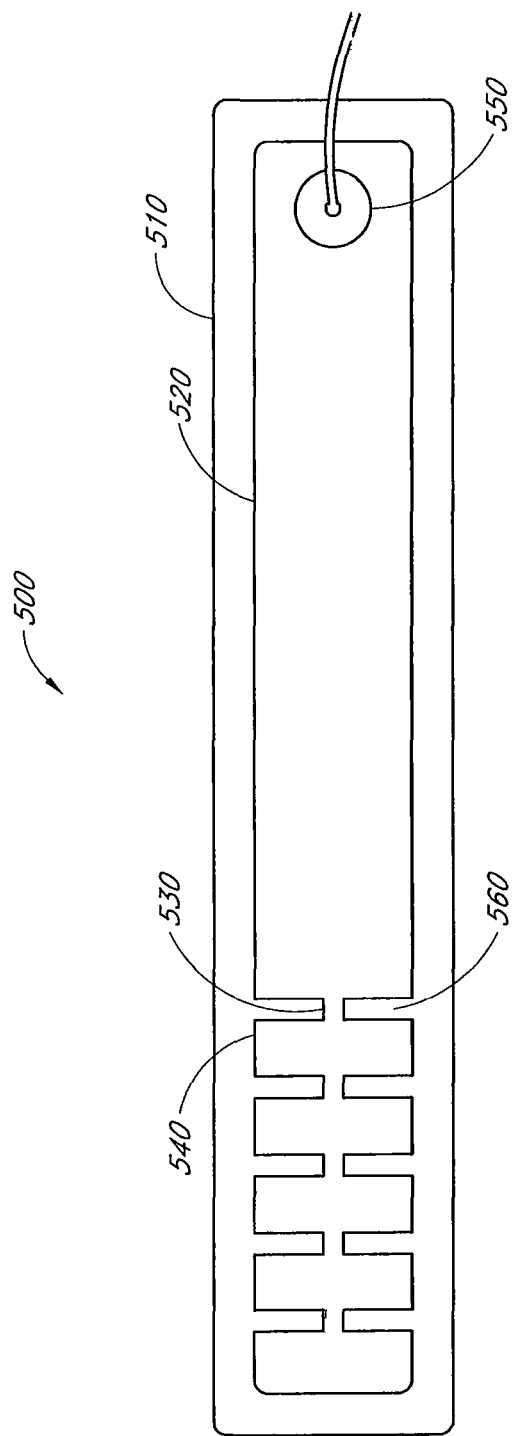
FIG. 5B illustrates another embodiment of a wound dressing trimmable at a bridge portion.

FIGS. 5A and 5B illustrate various embodiments of a wound dressing 500 which may be trimmable at a bridge portion 530. As used herein, a bridge or bridging or skirt portion can refer to a section of a dressing that bridges transmission of negative pressure across at least a portion of the dressing. Such bridge or bridging or skirt portions may, in some embodiments, bridge two segments of absorbent pad portions, however in other embodiments only one absorbent pad portion may connect to a bridge portion. Bridge portions can also function to bridge negative pressure transmission to other bridge portions.

The dressing 500 may comprise a backing layer 510, an absorbent layer and/or one or more transmission layers formed in a main portion 520 and at least one additional portion 540 separated by a gap 560 and connected by a bridge portion 530, and a port 550. In some embodiments, the main portion 520, additional portion 540 and bridge portion 530 comprise one or more transmission layers such as described above between an optional wound contact layer and a backing layer 510. The transmission layer(s) may comprise any material configured to transmit fluid and/or negative pressure. For example some embodiments of the transmission layer(s) may comprise the spacer layer 3450 of FIG. 4A, discussed above, which may be configured to evenly distribute negative pressure and vertically wick fluids. Other embodiments of the transmission layer(s) may comprise the acquisition distribution layer 3440 of FIG. 4A, discussed above, which may be configured to horizontally or laterally wick fluid. Other embodiments of the spacer layer and acquisition distribution layer are discussed with respect to FIGS. 4C and 9A, 9B, and 10A-10B discussed below. Further embodiments of the transmission layer can include an open-cell reticulated foam, as discussed below with respect to Table 1 and FIGS. 15A-16J. Some embodiments of the transmission layer(s) may comprise a first layer configured to vertically wick fluid and a second layer, positioned above the first layer, configured to horizontally wick fluid. One or both of the first and second layer may be present in the main portion 520, additional portion 540 and bridge portions 530. In some embodiments, the same layers may be found throughout the main portion 520, additional portion 540 and bridge portions 530.

In some embodiments, the portions of dressing 500 may have different layered structures. For example, in some embodiments the bridge portions 530 can comprise a material not included in the main portion 520 or additional portion 540, for example open-cell reticulated foam. In other embodiments a transmission layer may extend across the bridge portions 530, main portion 520, and additional portion 540, and the main portion 520, and additional portion 540 can additionally include an absorbent layer.

In any or all of the main portion 520, additional portion 540, and bridge portion 530, the dressing 500 may further comprise an optional absorbent material such as described herein positioned between the backing layer 510 and the one or more transmission layers. In some embodiments, the absorbent layer may have a similar footprint to the one or more transmission layers. In other embodiments, the absorbent layer may be located at main portion 520 and at least one additional portion 540, but the absorbent layer may not be included in the bridge portion 530. As illustrated, the dressing has an elongate, rectangular shape, though other shapes are also contemplated. The absorbent layer preferably has a smaller footprint than the backing layer, so that the absorbent layer is completely surrounded by the backing layer. It will be appreciated that in some embodiments, the absorbent layer is an integral, one-piece layer of material that extends across the main portion 520, the additional portion 540 and in the bridge portion 530 or alternatively extends across the main portion 520 but not the additional portion 540 or the bridge portion 530. Some embodiments may be manufactured without the port 550 and may include at least one area for attaching a port. For example, the port 550 may simply be an opening in the backing layer for attaching a separate port member.

The dressing 500 may also comprise other layers as discussed above with respect to FIGS. 3A-4B. For instance, the dressing 500 may comprise a wound contact layer which may be sealed to the backing layer 510, thereby creating an enclosed chamber for the absorbent layer and/or one or more transmission layers and any other layers within the dressing. The wound contact layer and backing layer may be sealed along a perimeter with a certain distance from the edge of the sealed perimeter to the edge of the absorbent layer. The wound contact layer and backing layer may also be sealed together throughout some or all of the area of a gap 560 between portions of the inner layers.

The transmission layers, as described above, may be provided for the transmission of negative pressure throughout the dressing and for drawing wound exudate away from the wound site and into the upper layers of the dressing 500 and/or laterally spreading wound exudate across the area of the dressing 500. As described above, the transmission layer(s) may comprise one or both of the spacer layer and acquisition distribution layer described with respect to FIG. 4A. Use of one or more of these layers may advantageously maintain fluid transmission through narrow portions of the dressing such as the bridge portions, and may keep these narrow portions from partially or completely collapsing under negative pressure. Further, having material such as the acquisition distribution material and/or absorbent material sized to overlap the edge of the transmission layer(s) may beneficially mitigate discomfort or pressure on skin during wear of the dressing.

Further, use of one or both of the spacer layer and acquisition distribution layer as the transmission layer(s) in the bridge portion 530 may provide advantages for internally sealing a trimmed portion of the dressing 500. Some embodiments of the spacer and acquisition distribution layers may have open, fibrous structures. After a dressing is trimmed or cut, in order to reseal the dressing, an adhesive such as curing silicone may be injected into the exposed portion of the transmission layer(s), thus creating a plug that substantially seals the exposed edge internally. Absorbent material may not be present in the bridge portion 530, as some embodiments of the absorbent material may be too dense to allow adhesive to flow into the layer and thus does not allow for an exposed edge to be sealed internally. However, in embodiments containing a dense absorbent material in the bridge portion 530, an exposed end may be still be sealed externally, such as by covering the entire exposed edge with silicone from backing layer to skin or sealing the exposed edge with adhesive tape or a sealing strip. Having absorbent material and/or acquisition distribution material in the bridge portion 530 may provide the benefit of distributing absorbed liquid between the main portion 520 and any additional portions 540.

As illustrated in FIG. 5B, the absorbent layer and/or one or more transmission layers may comprise a main portion 520 and a plurality of additional portions 540. The additional portions may be smaller than or the same size as the main portion 550. For example, as measured along the longitudinal length of a rectangular dressing, the length of the additional portions may be smaller than the length of the main portion, and each additional portion may have the same length. As illustrated, the main portion 520 is connected to the first additional portion 540 by one bridge portion 530 aligned along the center longitudinal axis of the dressing 500, and each additional portion is connected to the next additional portion by a similar bridge. The bridge portion may in FIGS. 5A and 5B may also be located off the center axis, for example at the side of the dressing. Other embodiments may employ a plurality of bridges for connecting the portions of the dressing. For example, one embodiment may employ two bridges to connect adjacent portions, wherein the bridges are located at the side edges of the adjacent portions next to the sealed perimeter. Another embodiment may employ two bridges each located a distance away from the side edges of the adjacent portions.

In some embodiments the main portion 520 may be a precalculated minimum length, and some or all of the additional portions 540 may have lengths that can be removed for custom sizing of the dressing to a variety of lengths exceeding the minimum length. The main portion length may be longer than the additional portion lengths, or the main portion may have the same length as the additional portions. Such embodiments may be advantageous for a long incision such as a leg incision made for a vein harvest. In an embodiment, the main portion 520 may be a minimum incision length or minimum leg length, and the additional portions 540 may be included in the dressing to achieve a length up to a maximum incision length or a maximum leg length. In use, the dressing may be trimmed according to the incision or leg length of the patient across the bridge portions, for example at cut line 570 described below. In some embodiments, additional ports or port attachment sites may be located on some or all of the additional portions in order to maintain a substantially even level of negative pressure throughout a relatively long dressing.

The bridge portion 530 in FIGS. 5A and 5B creates a continuous path for negative pressure delivery between multiple portions of the dressing. The bridge portion 530 may have a width that is less than ⅛, ¼, or ⅓ the width of adjacent portions of absorbent material and/or one or more transmission layers. A wider bridge portion allows for greater transmission of negative pressure and fluids such as wound exudate, however a narrower bridge portion is advantageous for sealing a dressing trimmed at the bridge portion. Further, patient comfort may be enhanced if the bridge portion 530 is wide enough to cover a wound or an incision. Embodiments of the dressings described herein may balance these factors according to a variety of purposes and/or considerations, and therefore the width of bridge portion 530 may vary. In some embodiments the bridge portion 530 may be approximately 15 mm wide, however other embodiments may be 10 mm to 20 mm (or about 10 mm to about 20 mm) wide or thinner or thicker. For example, a spacer material used as a transmission layer in a bridge portion can have a width of approximately 1 mm and a height of approximately 2 mm and maintain clinically appropriate negative pressure transmission. Accordingly, in some embodiments, the cross-sectional area of a bridge portion may be 2 mm² or approximately 2 mm², or more. Other materials may have varying minimum widths and heights for use in bridge portions according to their negative pressure transmission properties. The bridges can have any of the ranges of dimensions from the examples discussed below with respect to FIGS. 15A-16J. In embodiments employing a plurality of bridge portions, the bridge portions may all be a uniform width or may have varying widths. In some embodiments, the bridge portion 530 may comprise a wound contact layer, one or more transmission layers (which may be one or both of the wicking layer or acquisition distribution layers described above with respect to FIG. 4A), and a backing layer. Some embodiments of the bridge portion 530 may further comprise an absorbent or superabsorbent layer. The layers in the bridge portions 530 may be continuous with layers found in the portions 520 or 540 of the dressing, or they may be discrete layers positioned side-by-side. In some embodiments, the bridge portions 530, main portion 520, and additional portions 540 may be a continuous layer of a single material, for example open-cell reticulated foam, positioned between a wound contact layer and a top film layer.

In a dressing applied to a nonplanar surface, the bridge portions may also advantageously provide enhanced flexing of the dressing for conforming to the nonplanar surface. Further, the bridge portions may enhance side flexing capabilities of the dressing for covering a curved or arcuate incision. In some embodiments, the location and width of the bridge portions may be selected for both connecting a plurality of trimmable portions as well as for flexibility of the dressing.

The dressing 500 may be trimmed at or across the bridge portion 530. Although the dressing may be trimmed at any portion, trimming the dressing at bridge portion 530, for example perpendicular to the length of the dressing, enables easier sealing as a narrower cross sectional area is exposed, and thus less area requires sealing after trimming. In some embodiments, the gap 560 may have the same width as the distance from the sealed perimeter edge to the absorbent layer, such that when the dressing is trimmed along a trim line 570 adjacent to the additional portion 540 the sealed perimeter around the inner layer(s) is substantially unchanged. In some embodiments this width may be approximately 2.5 cm, and in other embodiments may be any width suitable for maintaining the seal between the backing layer and the wound contact layer. It will be appreciated that the dressing may be trimmed at locations other than the illustrated trim line 570, which is included for illustrative purposes only, for example at a trim line in the center of the bridge portion 530 or at a diagonal or curved trim line.

In some embodiments, the absorbent layer and/or other layers of the wound dressing may be prescored for sizing. Other layers, such as the transmission layer(s) or acquisition distribution layer, may also be prescored. The backing layer may not be scored, as a through hole may limit the ability of the backing layer to function as a bacterial barrier or compromise the ability of the dressing to maintain negative pressure. Other embodiments may include a printed or indented pattern on some or all of the layers to indicate possible trim lines.

Each of the main portion 520 and additional portion(s) 540 may be considered a negative pressure treatment module, all or some of which may be used to provide negative pressure to a wound site. For example, if the dressing 500 of FIG. 5A or 5B is left untrimmed, all of the modules cooperate together to provide negative pressure to a wound site. Alternatively, if one or more of the additional portions 540 is trimmed and removed, the remaining portion(s) or module(s) can be used to provide negative pressure to the wound site. After trimming, the dressing 500 may be sealed by an adhesive strip, a piece of a sealing drape, by another dressing, or by a sealant. In some embodiments, a retention strip may be applied at the interface of the dressing edge and the skin. The retention strips may be applied to cover trimmed dressing borders. In some embodiments the retention strips may comprise a pressure-sensitive adhesive on the lower surface, and in other embodiments may be applied over a sealant. It will be appreciated that any other adhesive method or mechanism may be used to seal the dressing. For example, a sealant may be applied with a tool such as a syringe around the trimmed area in order to reseal the chamber of the dressing or to seal the dressing to a patient. Some embodiments of the dressing may be self-sealing.

Figure 6:
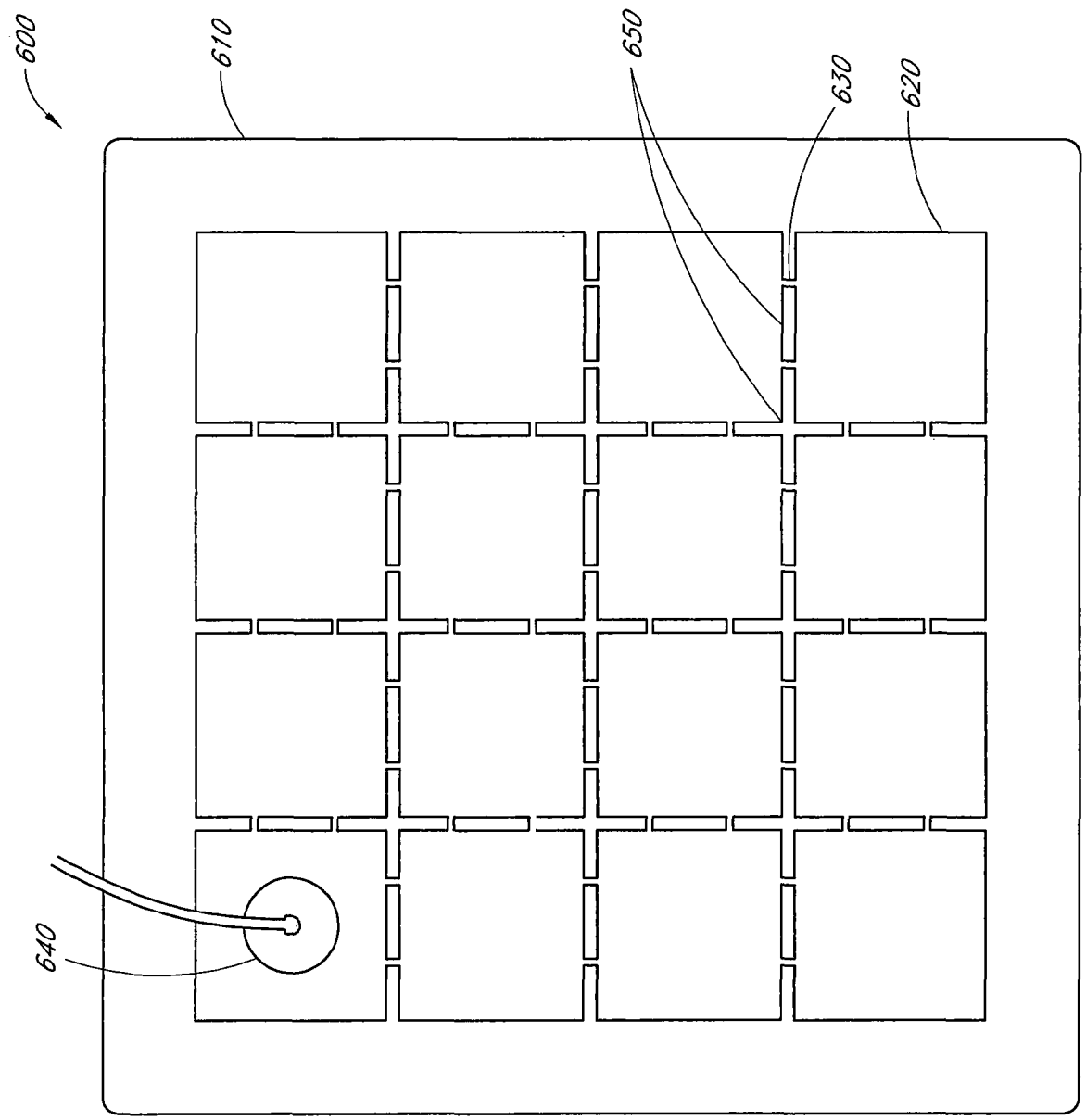
FIG. 6 illustrates an embodiment of a trimmable wound dressing comprising a plurality of portions or cells.

FIG. 6 illustrates an embodiment of a trimmable wound dressing 600 comprising a plurality of portions or cells 620. As illustrated, the cells 620 are repeating to form a plurality of repeating negative pressure treatment modules. The dressing 600 may comprise a sealed perimeter 610 of a backing layer and a wound contact layer, a plurality of cells 620, a plurality of bridges 630 connecting adjacent portions, and a port member 640. As described above, the dressing 600 may be trimmed at the bridge portions and sealed along the trim line. Each of the cells 620 may include absorbent material and/or one or more transmission layers as described above, along with other optional layers. The bridge portions 630 may comprise a wound contact layer, one or more transmission layers (which may be one or both of the wicking layer or acquisition distribution layers described above with respect to FIG. 4A), and a backing layer. Some embodiments of the bridge portions 630 may further comprise an absorbent or superabsorbent layer. The layers in the bridge portions 630 may be continuous with layers found in the cells 620, or they may be discrete layers positioned side-by-side. The cells 620 and bridge portions 630 can be formed from a continuous single layer in some embodiments, for example open-cell reticulated foam.

As illustrated, the dressing comprises a 4×4 array of cells 620. Other embodiments may comprise any suitable array of cells, or may be configured as a long rolled dressing N cells wide. The cells may be connected by one or more narrow bridge portions 630 and separated by gaps 650. The backing layer and wound contact layer may be sealed together throughout the gaps. By trimming at the bridge portions 630, the integrity of the dressing may be maintained even as the dressing is significantly resized. For example, the dressing may be trimmed so that only one inner cell or a group of inner cells remain, and the layers of the dressing will not separate due to the sealing of the backing layer and wound contact layer throughout the area of the gaps 650.

In some embodiments, the center cells of the dressing 600 may be removed. This may provide benefits, for example, when the dressing is used to cover a grafted skin flap or sutured skin flap. The dressing may be resized so that the unsutured skin is substantially uncovered by the dressing. Thus, the removed sections would otherwise cover the healthy skin of the flap. Covering the healthy skin with the dressing potentially creates problem such as exposing the wound to bacteria on the surface of the flap and exposing the healthy skin of the flap to excess moisture. The dressing may also be resized accordingly to cover circular, curved, or otherwise irregularly shaped suture lines.

The port member 640 may be located, as illustrated, on a corner cell of the dressing 600. However, in other embodiments the port may be located on a different cell. Some embodiments may employ multiple ports, each port connected to a different cell. For example, a large dressing or longed rolled dressing may comprise a port at an edge cell of every N rows, such every as four rows or five rows. Some embodiments may, instead of the illustrated port member 640, comprise a port attachment site or sites.

Figure 7:
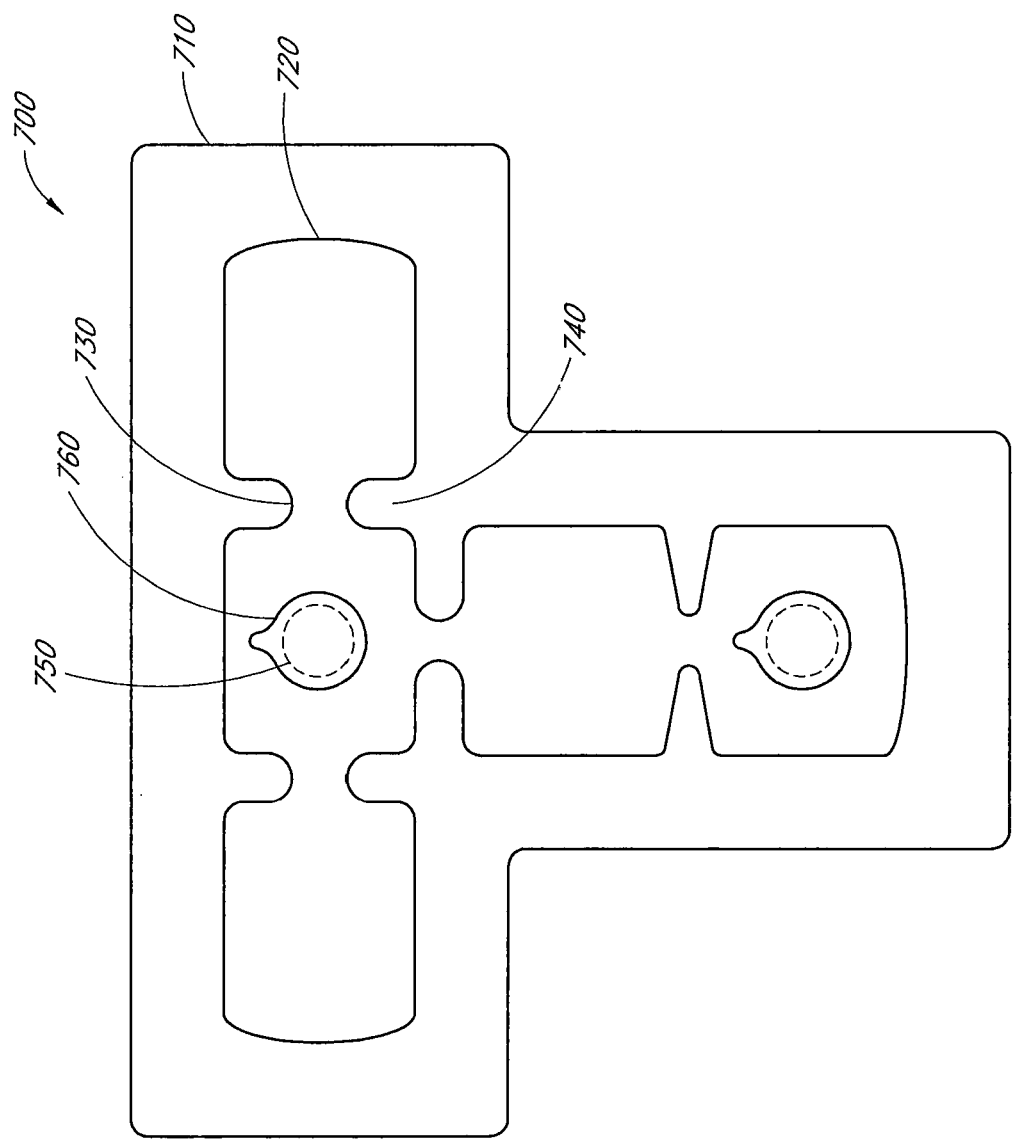
FIG. 7 illustrates an embodiment of a trimmable T-shaped wound dressing comprising a plurality of portions with multiple port attachment sites.

FIG. 7 illustrates an embodiment of a trimmable wound dressing 700 comprising a plurality of portions with multiple port attachment sites 760. Similar to the dressing 600 described above, the T-shaped dressing 700 comprises a backing layer and wound contact layer having a sealed perimeter 710 around a plurality of cells 720 containing absorbent material and/or one or more transmissions layer connected by bridge portions 730 and separated by gaps 740. The bridge portions 730 may comprise a wound contact layer, one or more transmission layers (which may be one or both of the wicking layer or acquisition distribution layers described above with respect to FIG. 4A), and a backing layer. Some embodiments of the bridge portions 730 may further comprise an absorbent or superabsorbent layer. The layers in the bridge portions 730 may be continuous with layers found in the cells 720, or they may be discrete layers positioned side-by-side. The backing layer and wound contact layer may also be sealed together throughout some or all of the area of the gaps 740. As described above, the dressing 700 may be trimmed at the bridge portions and sealed along the trim line. Although the dressing is illustrated as being T-shaped, this is for illustrative purposes only, and the dressing may be a variety of branched shapes. Each branch may comprise one or more cells connected by one or more bridge portions. The cells 720 and bridge portions 730 can be formed from a continuous single layer in some embodiments, for example open-cell reticulated foam.

The dressing comprises a plurality of port attachment sites 760. Each attachment site 760 may be a hole in the backing layer and may be covered with a removable tab 760. The tab may comprise a suitable backing material with a layer of adhesive on some or all of the lower surface. Some embodiments may comprise a ring of adhesive sized to surround the hole 750 in the backing layer. The tab 760 may be removed so that a port may be attached to the backing layer over the hole 750 for transmission of negative pressure into the dressing 700. In some embodiments, port attachments may be secured at just one port attachment site. In other embodiments, port attachments may be secured over a plurality of attachment sites as needed for transmission of negative pressure throughout the dressing. Some ports may comprise an adhesive on the lower surface thereof for attachment to the dressing. Some embodiments of the dressing may comprise an adhesive layer for attaching the port.

Figure 8:
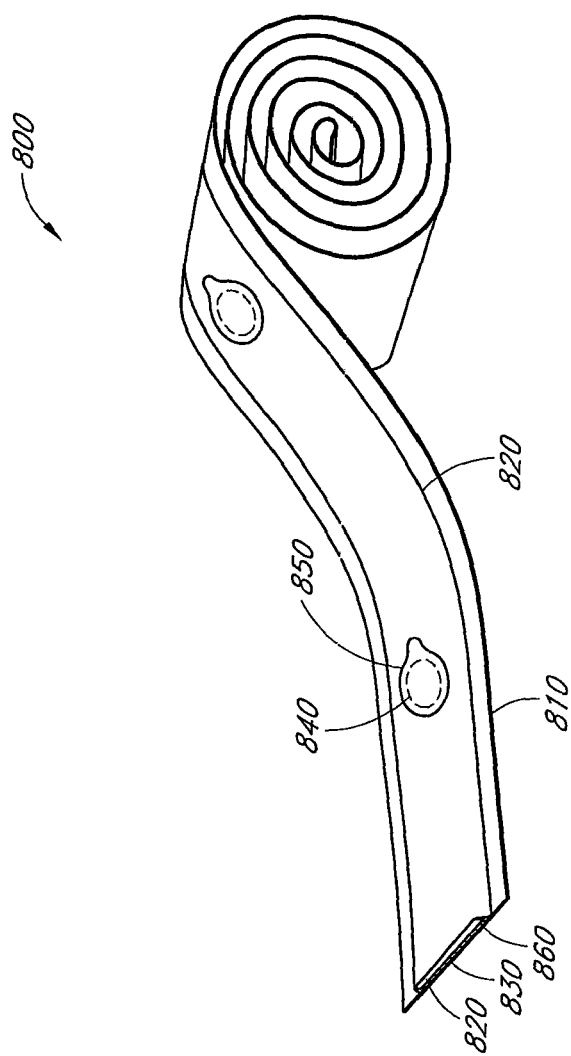
FIG. 8 illustrates an embodiment of a trimmable wound dressing with multiple port attachment sites.

FIG. 8 illustrates an embodiment of a trimmable wound dressing 800 with multiple port attachment sites 840. The dressing comprises a backing layer and wound contact layer having a sealed perimeter 810, an absorbent layer 820, a spacer layer 830 below the absorbent layer, and a plurality of holes 840 in the backing layer covered by tabs 850. The spacer layer 830 may be one or both of the transmission layer and acquisition distribution layer discussed above. It will be appreciated that in some embodiments, only one of the absorbent layer or spacer layer may be provided, with the other layer being optional.

The dressing 800 is configured as a roll with port attachment sites 840 spaced a distance apart along the upper surface. Trimmable portions may be located between adjacent port attachment sites 840 where the dressing 800 may be cut or separated. Accordingly, the dressing 800 may be considered to include a plurality of repeating negative pressure treatment modules, where one or more of the modules can be removed and the removed module(s) can subsequently be used to provide negative pressure to the wound site. In some embodiments this distance may be uniform between all port attachment sites, and in other embodiments the distance may vary. The dressing roll may be custom sized by unrolling a length of dressing, trimming the dressing, sealing the two sides, and attaching a port or ports to one or more port attachment sites. In some embodiments, unused port attachment sites 840 may remain sealed by adhesive tabs 850. In some embodiments, the spacer layer 830, and optionally the absorbent layer 820, may comprise a bridge portion or plurality of bridge portions located between each port attachment site for ease of sealing a trimmed dressing. It will be appreciated that any of the dressings described above may be configured as a trimmable roll with a plurality of port attachment sites located a distance apart on the roll. For example, an elongate dressing configured as a roll may include narrower bridging portions spaced along a length of the dressing between port attachment sites to facilitate trimming of the dressing to a suitable size.

In some embodiments, a wound contact layer 860 can be positioned under the spacer layer 830. At least a portion of lower surface of wound contact layer 860 may be provided with an adhesive for sealing to a patient's healthy skin. Prior to use, the adhesive can be covered with a protective layer (not illustrated). Similar to the multi-part protective layer employing folded handles, as illustrated in FIGS. 14C and 14D and discussed in more detail below, the protective layer over the lower adhesive of dressing 800 can have a central portion and two outer handle portions. The handle portions can run lengthwise, for example along or near the sealed perimeter 810, so that the handles will be available for easy removal of the protective layer on any cut portion of the dressing 800.

Such adaptable, resizable dressings may provide the advantage of reducing the inventory of dressings that a hospital or clinic is required to keep. Rather than maintaining a large inventory of dressings consisting of a multitude of shapes and sizes for all possible wound or incision sites, a hospital or clinic may only require one or several of the dressings described herein which can be modified to suit any patient needs. Further, it may be advantageous from a manufacturing perspective to produce adaptable dressings.

V. Overview of Example Layer Materials

Figure 9A:
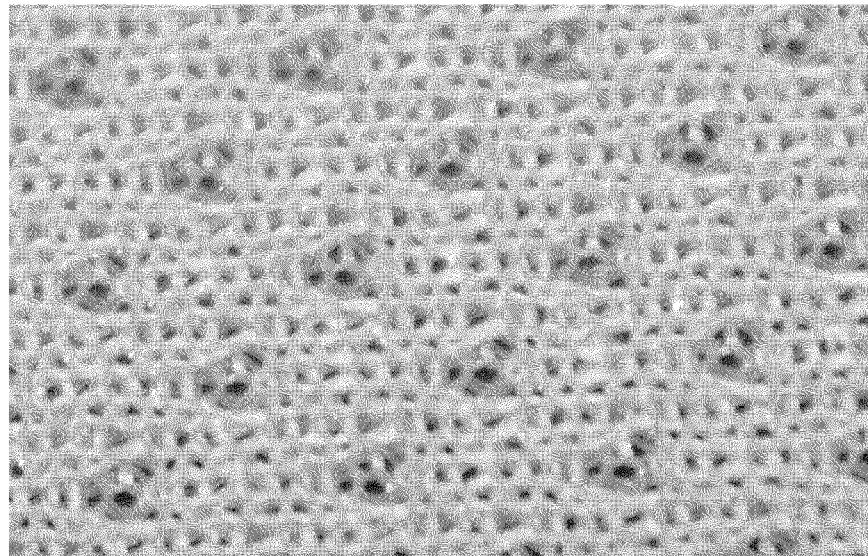
FIGS. 9A and 9B illustrate one embodiment of spacer layer material.
Figure 9B:
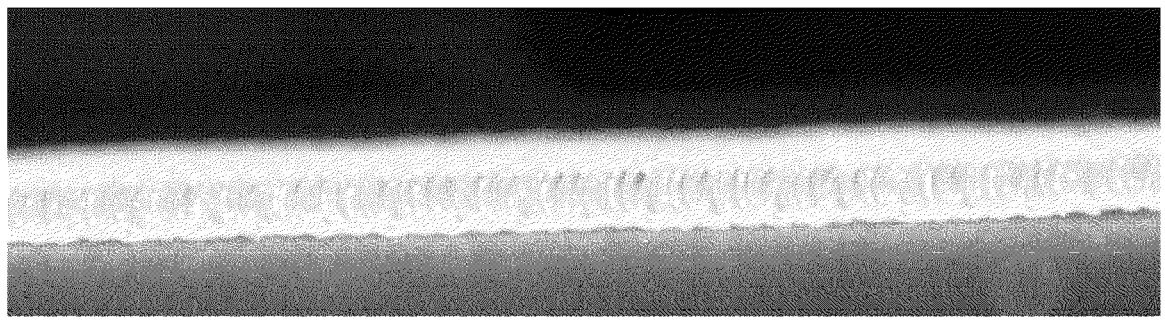

FIGS. 9A and 9B illustrate one embodiment of spacer layer, or transmission layer, material which may be used in any of the dressing embodiments described above, and which may also be used in any of the port or fluidic connector embodiments described above. The spacer or transmission material is preferably formed of a material having a three dimensional structure, and may have a top layer and a bottom layer comprising a knit pattern. For example, a knitted or woven spacer fabric (for example Baltex 7970 weft knitted polyester) or a non-woven fabric could be used. The top and bottom fabric layers may comprise polyester, such as 84/144 textured polyester or a flat denier polyester. Other materials and other linear mass densities of fiber could of course be used. In some embodiments, the top and bottom fabric layers may be the same pattern and the same material, and in other embodiments they may be different patterns and/or different materials. The top fabric layer may have more filaments in a yarn used to form it than the number of filaments making up the yarn used to form the bottom fabric layer, in order to control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. FIG. 9A illustrates one possible knit pattern for a top or bottom fabric layer.

As illustrated in the side view of FIG. 9B, between the top and bottom fabric layers may be a plurality of filaments. The filaments may comprise a monofilament fiber or a multistrand fiber, and may be knitted polyester viscose or cellulose. In some embodiments, a majority of the filaments, by volume, may extend vertically (that is, perpendicular to the plane of the top and bottom layers), or substantially or generally vertically. In another embodiment, 80%-90% (or approximately 80% to approximately 90%) of the filaments or more, by volume, may extend vertically, or substantially or generally vertically. In another embodiment, all or substantially all of the filaments, by volume, may extend vertically, or substantially or generally vertically. In some embodiments, a majority, 80%-90% (or approximately 80% to approximately 90%) of the filaments or more, or even all or substantially all of the filaments, extend upward from the bottom fabric layer and/or downward from the top fabric layer, and in some embodiments, such filaments extend over a length more than half the distance between the top and bottom fabric layers. In some embodiments, a majority, 80%-90% (or approximately 80% to approximately 90%) of the filaments or more, or even all or substantially all of the filaments, span a distance that is greater in a direction perpendicular to the top and bottom fabric layers (a vertical direction) than in a direction parallel to the top and bottom fabric layers (a horizontal direction). The orientation of such filaments may promote vertical wicking of fluid through the spacer layer. In some embodiments, the ratio of the amount of fluid wicked vertically through the spacer material to the amount of fluid wicked laterally across the spacer material when under negative pressure may be 2:1 or more, or approximately 2:1 or more, or may be up to 10:1 or more, or approximately 10:1 or more, in some embodiments. Such filaments may also keep the top and bottom layers spaced apart when exposed to compressive forces or negative pressure. Some embodiments of the spacer layer may have a tensile strength that substantially prevents tearing by typical force applied by human hands, and accordingly would need to be severed by other means, such as being cut or sliced, if implemented in a trimmable dressing.

FIGS. 10A-10D illustrate one embodiment of acquisition distribution layer (ADL) material which may be used in any of the dressing embodiments described above, and which may also be used in any of the port or fluidic connector embodiments described above. To those versed in the art of acquisition distribution layers it would be obvious that other ADL materials may be used to achieve a similar effect. Such ADL layers may be composed of multiple fibre types and be complex in structure and design. The ADL material, in an uncompressed state, may be 0.1 mm to 4 mm thick, or approximately 0.1 mm to approximately 4 mm thick, and in some embodiments may be 1.2 mm thick, or approximately 1.2 mm thick, in an uncompressed state. The ADL material may comprise a plurality of loosely packed fibers, which may be arranged in a substantially horizontal fibrous network.

In some embodiments, the ADL material may consist of a mix of two fiber types. One may be a flat fiber which may be 20 µm to 50 µm in width, or approximately 20 µm to approximately 50 µm in width, and may comprise a cellulosic based material. The other fiber may be a two component fiber that has an inner core that is 8 µm to 10 µm in diameter, or approximately is 8 µm to approximately 10 µm in diameter, and an outer layer with a thickness of 1 µm to 2 µm, or approximately 1 µm to approximately 2 µm. The two component fiber may be a mix of a polyethylene (PE) type material, and polyethylene terephthalate (PET). In some embodiments the inner core of the two component fiber may be PET and the outer layer may be PE. The PE/PET fibers may have a smooth surface morphology, while the cellulosic fibers may have a relatively rougher surface morphology. In some embodiments the ADL material may comprise about 60% to about 90% cellulosic fibers, for example approximately 75% cellulosic fibers, and may comprise about 10% to about 40% PE/PET fibers, for example approximately 25% PE/PET fibers.

Figure 10A:
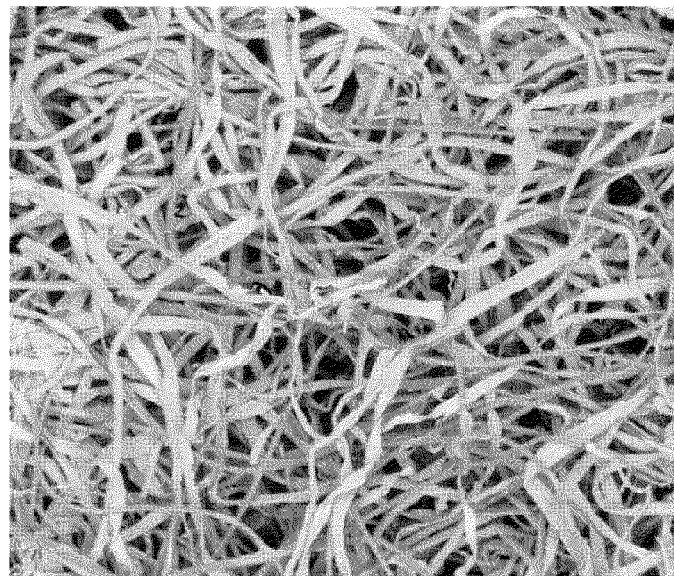
FIGS. 10A-10D illustrate one embodiment of acquisition distribution layer material.
Figure 10B:
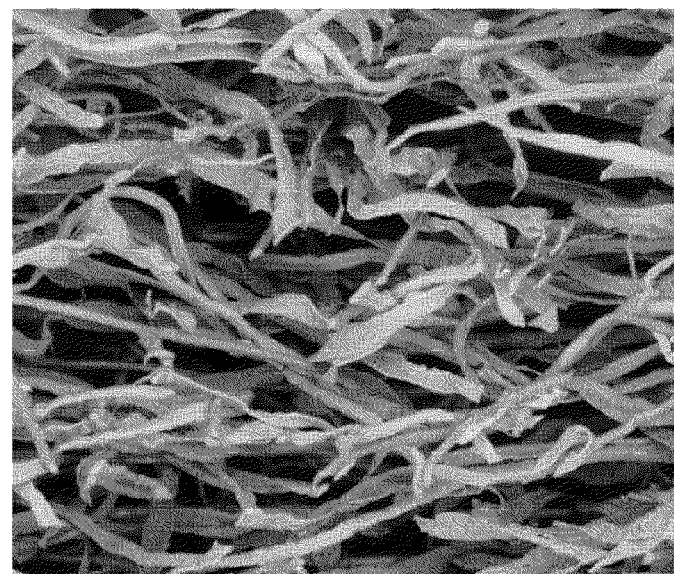

FIG. 10A illustrates a backscatter scanning electron microscope (SEM) plan view of a sample portion of acquisition distribution layer material at 140× magnification. FIG. 10B illustrates an SEM cross sectional view at 250× magnification. As illustrated in FIG. 10B, a majority of the fiber volume may extend horizontally (that is, parallel to the plane of the top and bottom surfaces of the material), or substantially or generally horizontally. In another embodiment, 80%-90% (or approximately 80% to approximately 90%) or more of the fiber volume may extend horizontally, or substantially or generally horizontally. In another embodiment, all or substantially all of the fiber volume may extend horizontally, or substantially or generally horizontally. In some embodiments, a majority, 80%-90% (or approximately 80% to approximately 90%) of the fibers or more, or even all or substantially all of the fibers, span a distance perpendicular to the thickness of the ADL material (a horizontal or lateral distance) that is greater than the thickness of the ADL material. In some embodiments, the horizontal or lateral distance spanned by such fibers is 2 times (or about 2 times) or more, 3 times (or about 3 times) or more, 4 times (or about 4 times) or more, 5 times (or about 5 times) or more, or 10 times (or about 10 times) or more the thickness of the ADL material. The orientation of such fibers may promote lateral wicking of fluid through the ADL material. This may more evenly distribute fluid such as wound exudate throughout the ADL material. In some embodiments, the ratio of the amount of fluid wicked laterally across the ADL material to the amount of fluid wicked vertically through the ADL material under negative pressure may be 2:1 or more, or approximately 2:1 or more, or may be up to 10:1 or more, or approximately 10:1 or more, in some embodiments.

Figure 10C:
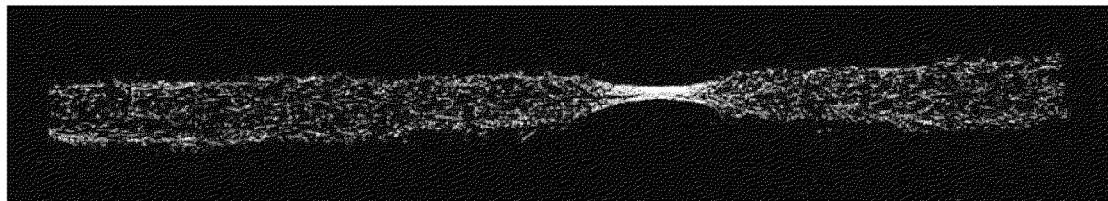
Figure 10D:
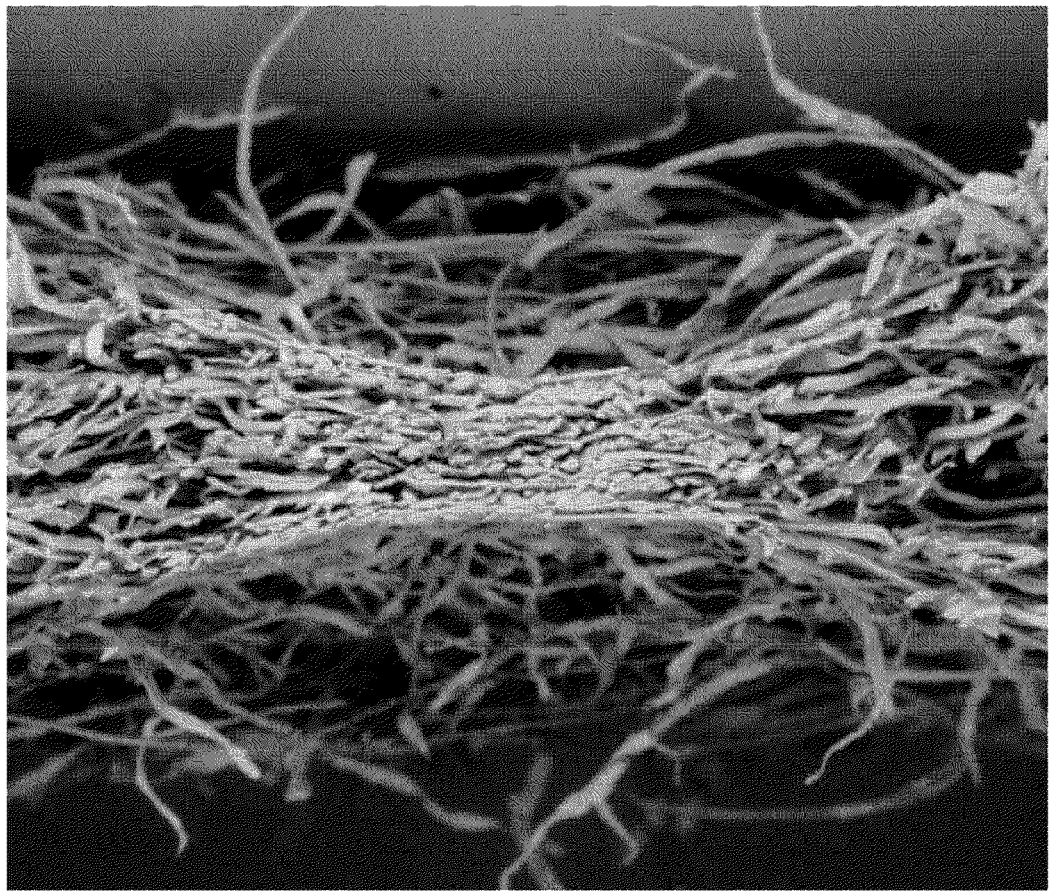

FIG. 10C is a two dimensional microtomographic cross sectional view of a compressed portion of a sample of ADL material which is approximately 9.2 mm long. FIG. 10D is an SEM cross sectional view at 130× magnification of the compressed portion illustrated in FIG. 10C. Such compressed portions may occur in the ADL material may occur due to the application of pressure to the material. FIGS. 10C and 10D further illustrate the horizontal network of ADL fibers.

Figure 11A:
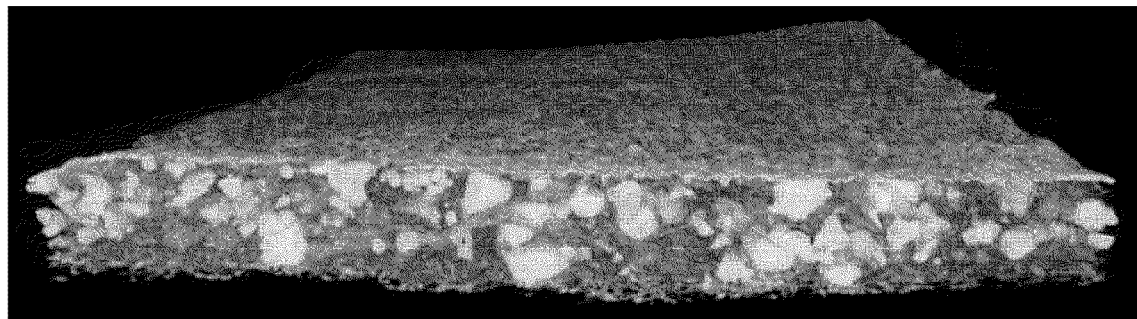
FIGS. 11A and 11B illustrate one embodiment of absorbent layer material.
Figure 11B:
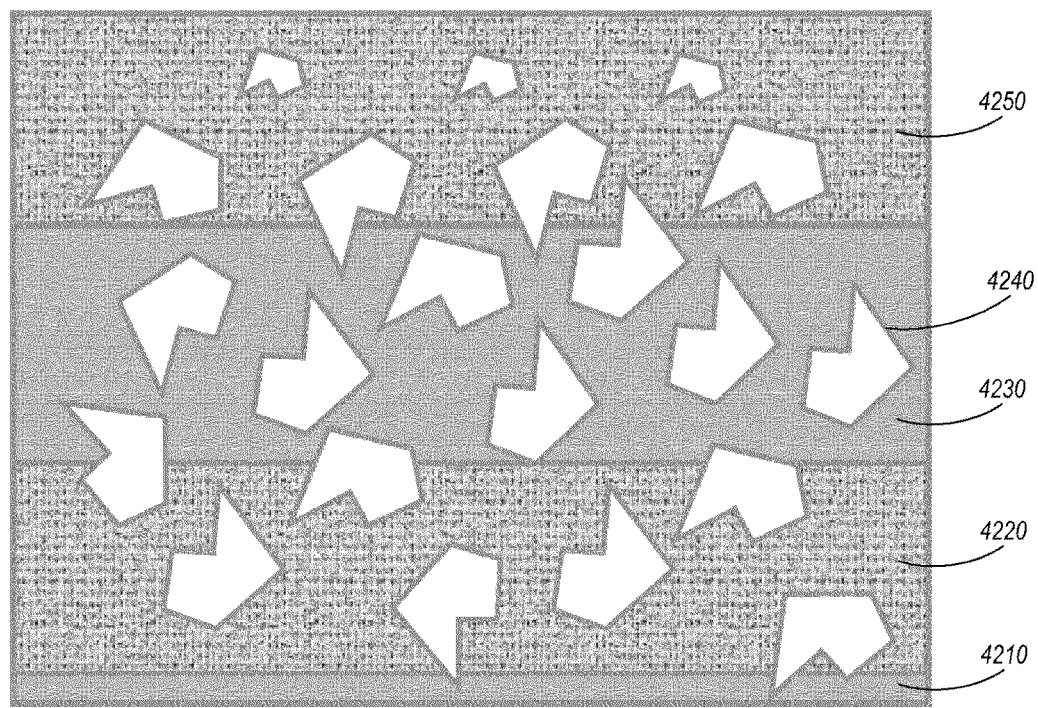

FIGS. 11A and 11B illustrate one embodiment of absorbent material which may be used in any of the dressing embodiments described above. FIG. 11A illustrates a three dimensional microtomographic cross sectional view of a sample of absorbent material, depicting a fibrous composition interspersed with superabsorbent particles. The absorbent material may, for example, be any of the materials described in U.S. Patent Pub. No. 2012/308780, titled "Absorbent Structure," filed May 25, 2012, the contents of which are hereby incorporated by reference in their entirety.

FIG. 11B is a cross sectional schematic diagram of an embodiment of the absorbent material illustrating a plurality of layers within the absorbent material. The absorbent material may have a textured layer 4210 on one side of a fibrous network, the fibrous network defining the bulk of the absorbent material and comprising layers 4220, 4240, and 4250. Superabsorbent particles 4230 may be dispersed throughout layers 4220, 4240, and 4250. The textured layer 4210, also referred to as the "tissue dispersant layer" in above portions of this specification, may be configured to laterally transmit fluid. Though depicted as the lowermost layer of the absorbent material, the textured layer 4210 may in some embodiments be positioned as the uppermost layer of the absorbent material, and in some embodiments may be positioned as both the lowermost and uppermost layers of the absorbent material. The textured layer 4210 may comprise flat fibers 20 µm to 50 µm in width, or approximately 20 µm to approximately 50 µm in width. The textured layer 4210 may comprise 1 to 2 or approximately 1 to approximately 2 layers of the flat fibers, and the textured layer 4210 may have an overall thickness of 0.04 mm, or approximately 0.04 mm.

The bulk of the absorbent material, comprising layers 4220, 4240, and 4250, may have a thickness of 1.7 mm, or approximately 1.7 mm, or may have a thickness in the range of 0.5 mm to 5.0 mm, or about 0.5 mm to about 5.0 mm. The bulk of the absorbent material may comprise a mix of two fiber types arranged in a fibrous network, for example the cellulosic fiber having a width of 20 µm to 50 µm, or approximately 20 µm to approximately 50 µm, and the PE/PET composite fiber, described above with respect to the ADL material. The superabsorbent particles 4230 may be irregularly shaped and varied in size, and may have a diameter of up to 1 mm, or approximately 1 mm. The superabsorbent particles 4230 may comprise a sodium acrylate type material. There may be relatively fewer superabsorbent particles in a portion of the uppermost surface of the bulk of the absorbent material (the surface of layer 4250 opposite the textured layer 4210), for example in an uppermost surface having a thickness of approximately 0.1 mm.

Layer 4220 may be a liquid absorption layer configured to draw liquid upward through the material towards layers 4240 and 4250. Layer 4240 may be a storage layer configured to hold absorbed liquid. Layer 4220 may be a liquid distribution layer configured to apply a "reverse suction" effect to the liquid storage layer 4240 in order to inhibit (or substantially inhibit) absorbed liquid from leaking back down through the lower layers of the absorbent material, a phenomenon which is commonly known as "back wetting."

Superabsorbent particles 4230 may be distributed primarily within the storage layer, may extend partially into the absorption layer 4220 and liquid distribution layer 4250, or may be distributed evenly (or substantially evenly) throughout the layers. The layers 4220, 4240, and 4250 may overlap with a portion of adjacent layers, and may or may not be separable.

Figure 12A:
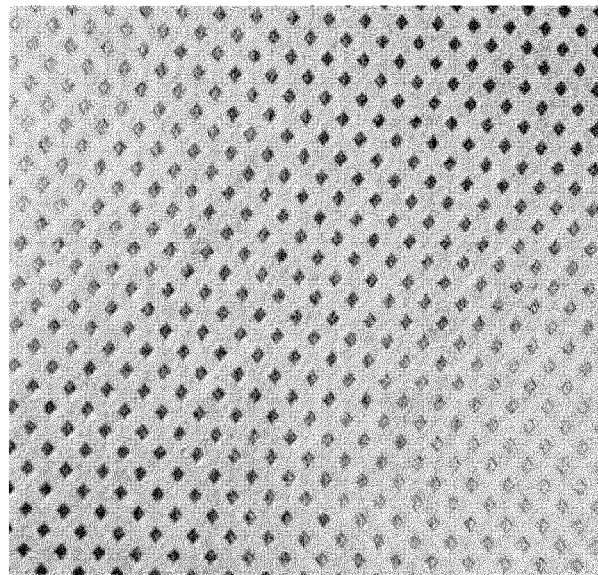
FIGS. 12A and 12B illustrate one embodiment of obscuring layer material.
Figure 12B:
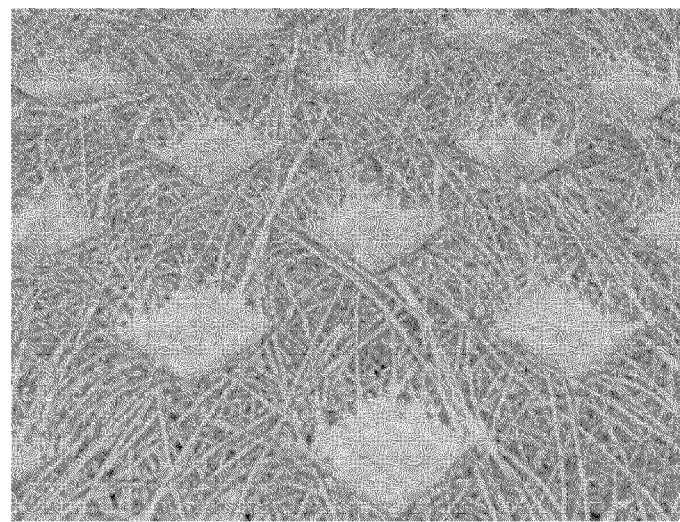

FIGS. 12A and 12B illustrate one embodiment of obscuring layer material which may be used in any of the dressing embodiments described above. FIG. 12A illustrates a photographic plan view of obscuring material, depicting a material comprising a fibrous network having a reoccurring regularly spaced criss-cross diamond pattern. The diamond shaped pattern may, in one embodiment, be 1.2 mm long by 1.0 mm wide, and may have a thickness of approximately 0.04 mm thick, consisting of fibers that are more densely packed relative to the surrounding area of the material. The diamond shaped pattern may increase structural stability of the fibrous network of the material, for example serving as "tacking" points. FIG. 12B illustrates a three dimensional microtomographic perspective view of the compressed diamond pattern and the surrounding uncompressed fibers.

Some embodiments of the obscuring material may comprise polypropylene spunbond material. Further, some embodiments of the obscuring material may comprise a hydrophobic additive or coating, for example a hydrophobic wash designed to permeate the fibers of the obscuring material to make the material substantially waterproof while permitting vapor permeability. Other embodiments may comprise a thin fibrous sheet of 60, 70, or 80 gsm. The fibers of the obscuring material may, in one embodiment, comprise layers of polypropylene (PP) fibers having a smooth surface morphology, and the PP fibers may have a thickness of approximately 25 µm. In some embodiments, the obscuring material may have a thickness of 0.045 mm or about 0.045 mm, or may have a thickness in the range of 0.02 mm to 0.5 mm, or about 0.02 mm to about 0.5 mm.

Figure 13:
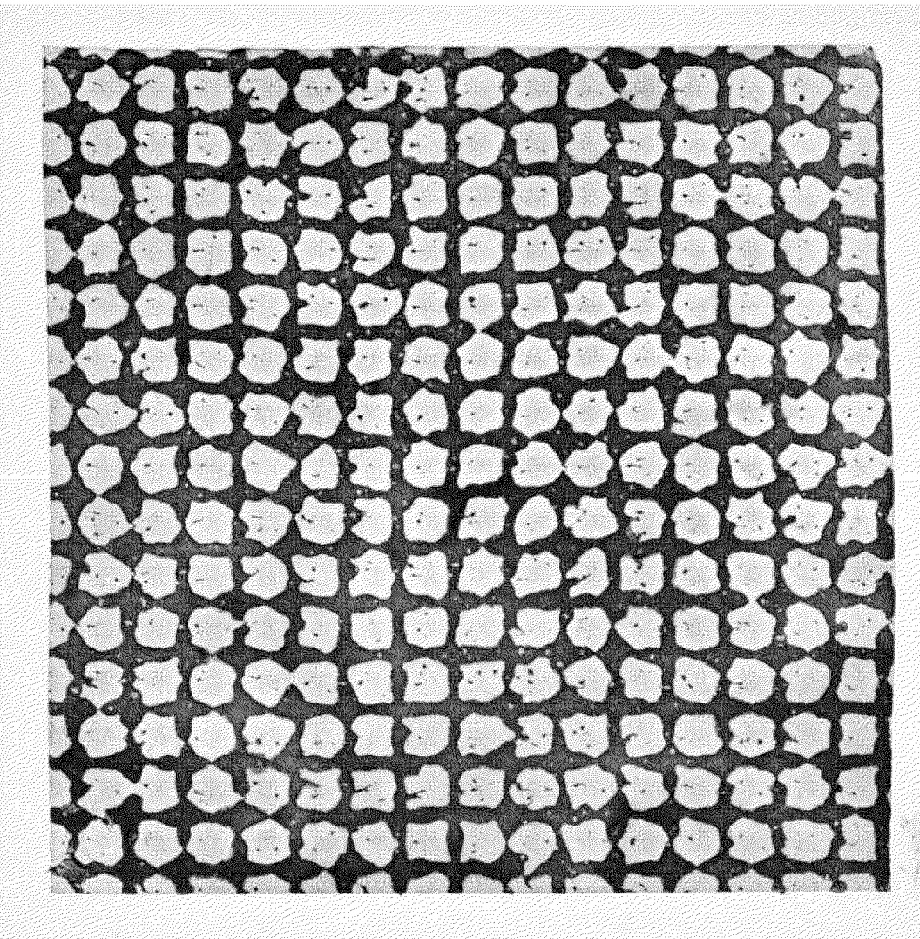
FIG. 13 illustrates one embodiment of an adhesive spread on cover layer material.

FIG. 13 illustrates one embodiment of an adhesive spread on approximately one square centimeter of a film material, which may be used as the cover or backing layer in any of the dressing embodiments or fluidic connector embodiments described above. The adhesive on the film has been covered with carbon powder for ease of illustrating the spread of the adhesive. The adhesive may comprise, for example, an acrylate type adhesive, for example K5 adhesive, and may be laid down in a criss cross pattern. In some embodiments, the adhesive material may cover approximately 45.5%±approximately 1.3% of the film surface. The pattern and coverage of the adhesive may vary so long as the configuration is suitable for desired vapor permeability.

VI. Overview of Example Sealing Strips

FIGS. 14A-14D illustrate one embodiment of a sealing strip assembly 4501 which may be used with a wound dressing and/or fluidic connector to provide additional sealing against the skin of the patient surrounding the wound dressing or fluidic connector. Sealing strips may also be used to reseal a cut or punctured wound dressing or fluidic connector. The sealing strips of FIGS. 14A-14D may be used, for example, like the fixation strips 210 of FIG. 2D.

As illustrated in FIG. 14A (top view), a plurality of sealing strips 4501 (labeled 4501a-4501f) may be provided together on one sheet 4500 with a plurality of perforations or weakened lines 4515, separating the individual sealing strips on the sheet. In some embodiments anywhere from 2 to 10 or more sealing strips may be provided on one sheet. As illustrated, six sealing strips 4501a, 4501b, 4501c, 4501d, 4501e and 4501f are provided on one sheet 4500 in FIG. 14A. In other embodiments each sealing strip may be provided separately, or a plurality of separate sealing strips may be provided, for example in a kit. A kit may be provided in the form of a tray, for example a sealed tray, which may include one or more sheets containing a plurality of sealing strips 4501 separated by the plurality of perforations or weakened lines 4515, or other embodiments of sealing strips as described. The kit may also contain a wound dressing with a fluidic connector that may be pre-connected to the wound dressing or separately provided. The wound dressing may have any of the shapes and layer configurations described above, and the fluidic connector may be any of the soft or hard ports described above. In some embodiments, the kit may further comprise a pump configured to connect to the fluidic connector and transmit negative pressure to the wound dressing.

An example perforation pattern of a perforated cut 4515 is illustrated in FIG. 14B, which an enlarged view of the portion of FIG. 14A labeled with the reference number 14B. In some embodiments, a repeating perforation gap 4525 may extend across the perforation, each gap separated by a connected or intact portion 4590. These perforation gaps 4525 may extend through some or all of the layers of the sealing strip assembly described further below. In some embodiments, a perforation gap 4525 may be 10 mm, or approximately 10 mm, in length, wherein length is the dimension measured along the perforation line. The perforation gap length may be also in the range of 2 mm to 20 mm, or approximately 2 mm to approximately 20 mm, in some embodiments. The intact portion 4590 separating perforation gaps may be in the range of 0.25 mm to 3 mm, or approximately 0.25 mm to approximately 3 mm, in length, for example 0.5 mm, or approximately 0.5 mm, in length.

As shown in FIGS. 14C and 14D (which are side or cross-sectional views of FIG. 14A), the sheet 4500 of sealing strips 4501, or an individual sealing strip 4501, may comprise an adhesive film 4545, which may be a flexible film material provided with a pressure-sensitive adhesive on a lower surface thereof. The adhesive film 4545 may, in some embodiments, be thin and prone to sticking to itself when folded or handled. Therefore, the adhesive film 4545 may be provided with a carrier layer 4535 on an upper, non-adhesive surface having the same length and width as the adhesive film 4545, and may also be provided with a one or protective layers 4570, 4580 on its lower, adhesive surface. The protective layers 4570, 4580 may be configured to protect the adhesive surface of the adhesive film 4545. First and second outer protective layers 4570 may be provided at opposite ends of the sheet 4500 or an individual sealing strip assembly 4501 (on the right and left sides of FIGS. 14A and 14C, with only the right side shown in FIG. 14D), thereby covering the opposite ends of the individual sealing strips 4501. A central protective layer 4580 may be provided over a central portion of the sheet 4500 or an individual sealing strip assembly 4501 and therefore over a central portion of adhesive film 4545, between the opposite ends of the adhesive film 4545 and partially overlapping with and underlying the outer protective layers 4570. As illustrated, the protective layers 4570 may have an outer edge (shown on the right in FIG. 14D) that is positioned beyond the outer edge of the adhesive film 4545, and may also include a folded handle 4575 that is covered by the central protective layer 4580. The folded handles 4575 of protective layer 4570 are therefore not in direct contact with the adhesive surface of the adhesive film 4545 to facilitate removal of the outer protective layers 4570. Similarly, the portions 4585 of the central protective layer 4580 overlapping the outer protective layers 4570 are not in direct contact with the adhesive surface of the adhesive film 4545, and are not adhered to the outer protective layers 4570, thereby forming handles to facilitate removal of the central protective layer 4580.

The carrier layer 4535 that may be provided on the upper surface of the adhesive film may be configured to releasably attach to the non-adhesive surface of the adhesive film 4545, and may comprise a sheet of paper or film with relatively more rigidity than the adhesive film. Release tabs 4595 may be provided on one or both opposite ends of the carrier layer 4535 for ease of removing the carrier layer 4535 from the adhesive film 4545. As illustrated in FIG. 14D, the release tabs 4595 may extend outwardly from the adhesive film 4545 and carrier layer 4535 to an outer edge aligned with an outer edge of the outer protective layer 4570. In some embodiments, graphical and/or numbered instructions for removal of the protective layer and carrier layer may be provided on one or both of the protective layer and carrier layer.

To utilize the sealing strips as described above, one or more sealing strips 4501 may be removed from the sheet 4500 by cutting or tearing along the perforations 4515. The central protective layer 4580 may be removed using the non-adhered portions 4585 of the central protective layer 4580, which serve as handles, for the exposing a central adhesive surface of the adhesive film 4545. The adhesive surface may then be applied to skin and/or a dressing or any desired location, or the adhesive surface may be applied after one or both of the outer protective layers 4570 is removed. The folded handle 4575 of outer protective layers 4570 may be grasped to remove the outer protective layers 4570, exposing the entirety of the lower adhesive surface of the adhesive film 4545. The outer edges of the adhesive surface of the adhesive film 4545 may be placed in a desired location. After sealing the adhesive film 4545, the release tab or tabs 4595 may be used to remove the carrier layer 4535 from the adhesive film 4545. This may be repeated with as many adhesive strips as are needed.

FIG. 14A illustrates a top view of assembly sheet 4500 of sealing strip assemblies 4501, in which the release tabs 4595 and carrier layer 4535 on adhesive film 4545 would be seen. The dashed lines in FIG. 14A illustrate edges or fold locations of the adhesive film 4545, central protective layer 4580, outer protective layers 4570, and carrier layer 4535. In some embodiments, each sealing strip 4501 may have a width 4530 of 40 mm, or approximately 40 mm, or a width in the range of 20 mm to 80 mm, or approximately 20 mm to 80 mm. The overall length 4510 of each sealing strip assembly (or the sheet 4500, including release tabs 4595 and outer protective layers 4570) may be 250 mm or 300 mm in some embodiments, or approximately 250 mm or approximately 300 mm, or in the range of 100 mm to 400 mm, or approximately 100 to approximately 400 mm. The length 4520 of the adhesive film 4545 and carrier layer 4535 may be 280 mm or 330 mm in some embodiments, or approximately 280 mm or approximately 330 mm, or in the range of 90 mm to 380 mm, or approximately 90 to approximately 380 mm. The length 4505 of central protective layer 4580 may be 210 mm or 260 mm in some embodiments, or approximately 210 mm or approximately 260 mm, or may be in the range of 100 mm to 300 mm, or approximately 100 mm to approximately 300 mm.

The length 4565 of outer protective layers 4570 (not including the folded portion) may be 85 mm or 110 mm in some embodiments, or approximately 85 mm or approximately 110 mm, or may be in the range of 50 mm to 200 mm, or approximately 500 mm to approximately 200 mm. The length 4555 of the folded portion or handle 4575 of outer protective layer 4570 may be 20 mm plus or minus 5 mm, in some embodiments, or approximately 20 mm plus or minus approximately 5 mm. The distance 4550 from the outer edge of the folded tab 4575 to the outer edge of the central protective layer 4580 may be 20 mm plus or minus 5 mm, in some embodiments, or approximately 20 mm plus or minus approximately 5 mm.

VII. Overview of Example Negative Pressure Delivery Testing

Figure 15A:
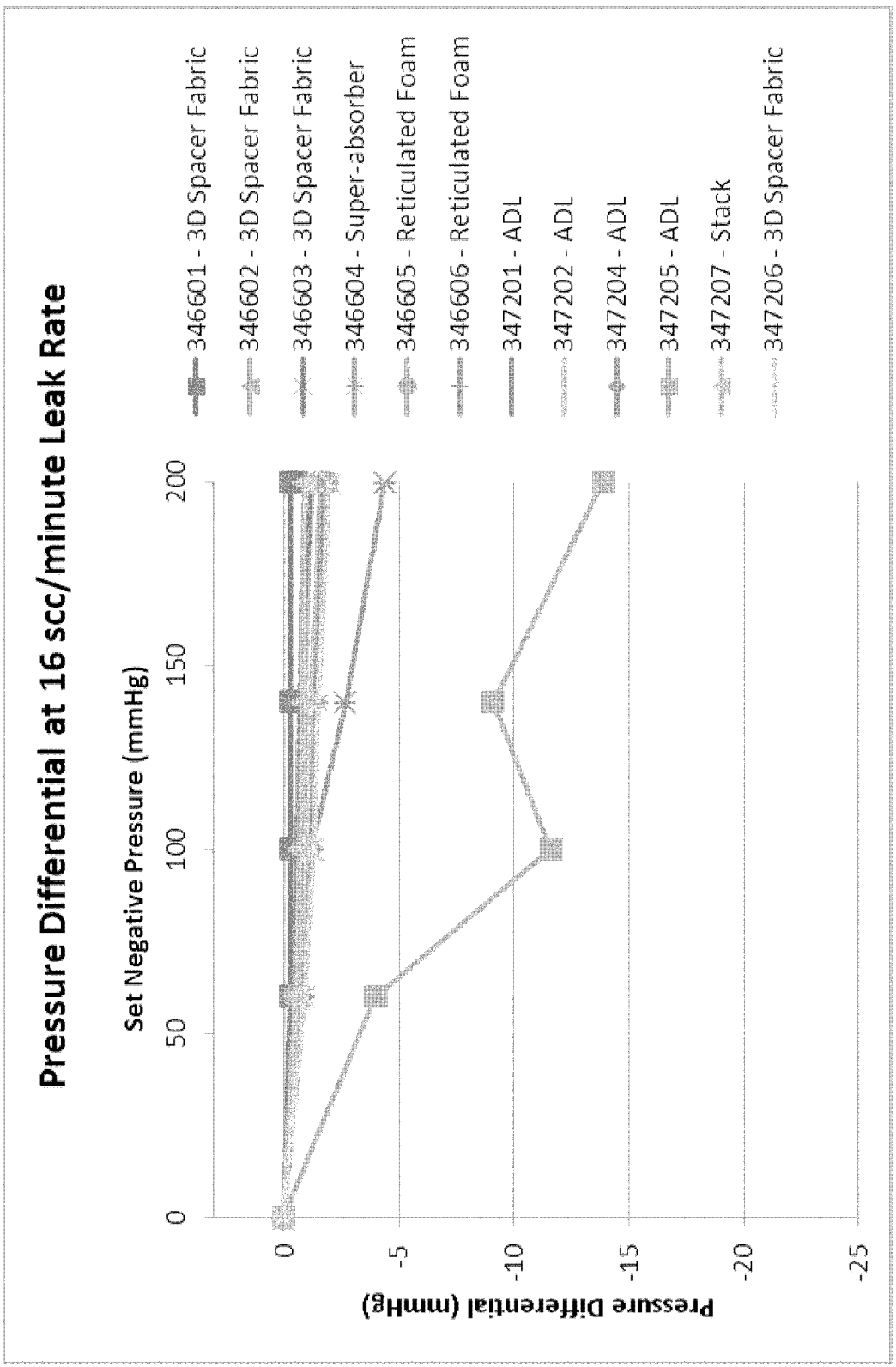
FIGS. 15A-15L illustrate differential pressure results of dry testing various materials for bridge sections of a dressing.
Figure 15B:
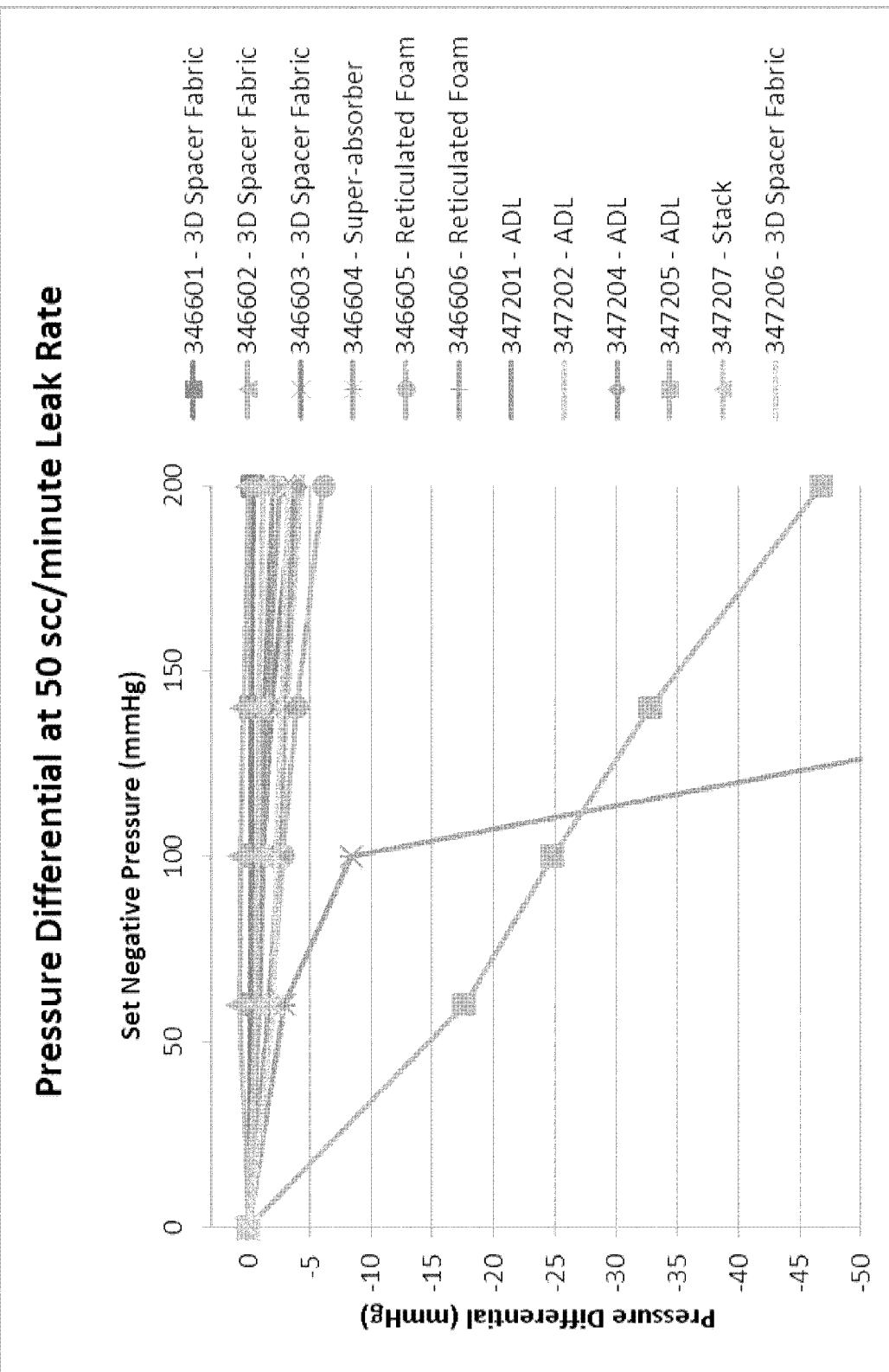
Figure 15C:
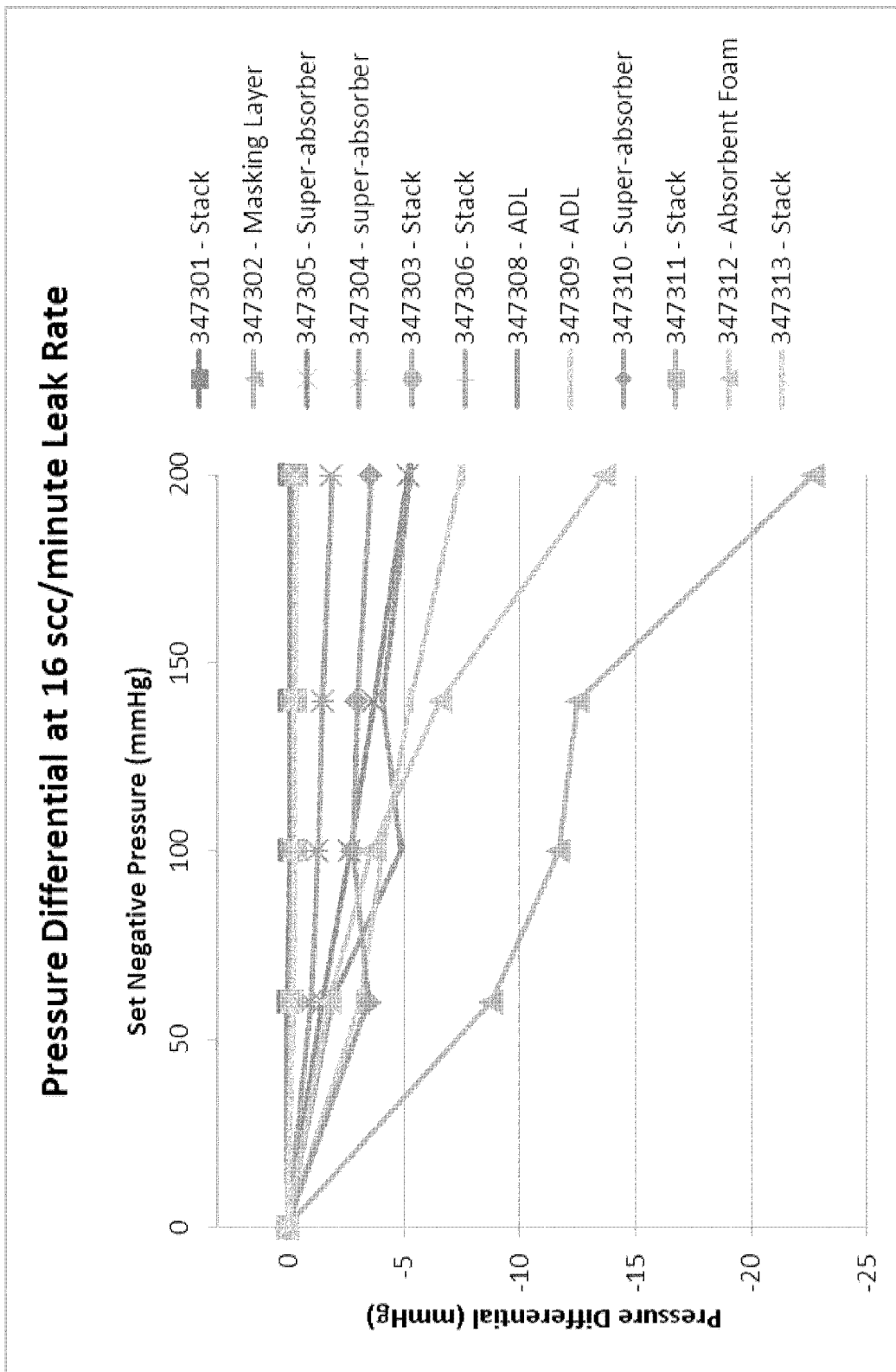
Figure 15D:
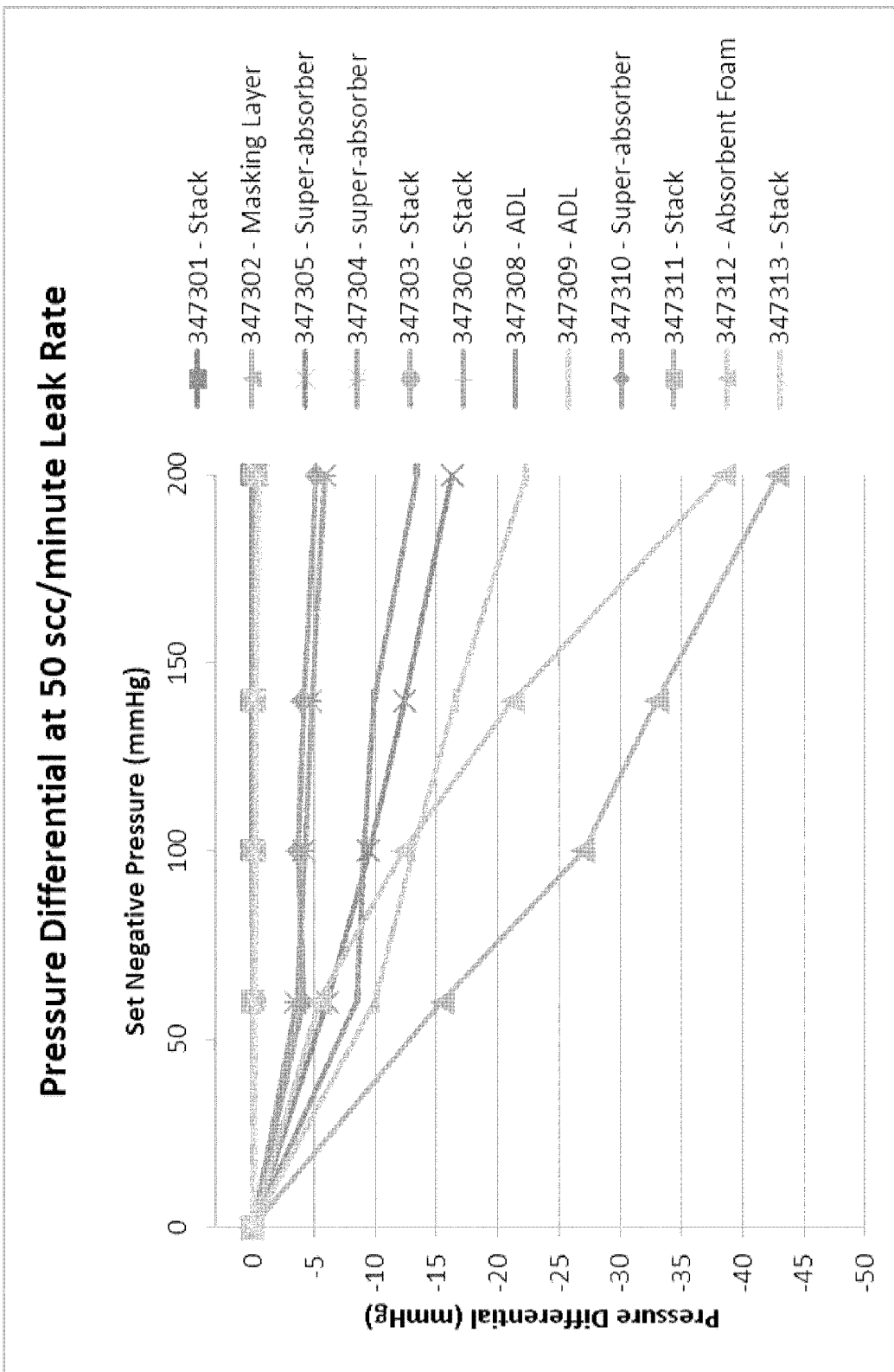
Figure 15E:
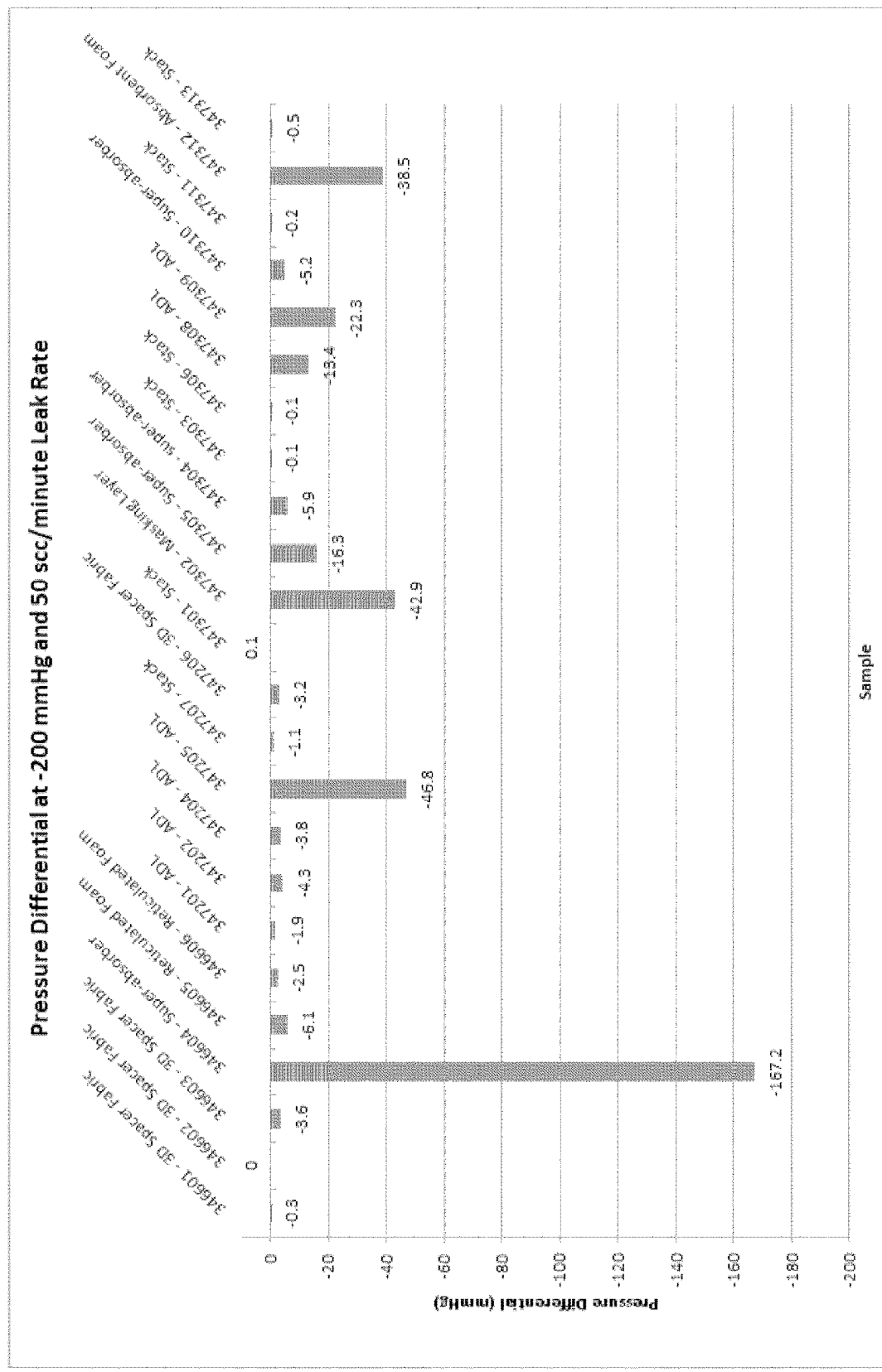
Figure 15F:
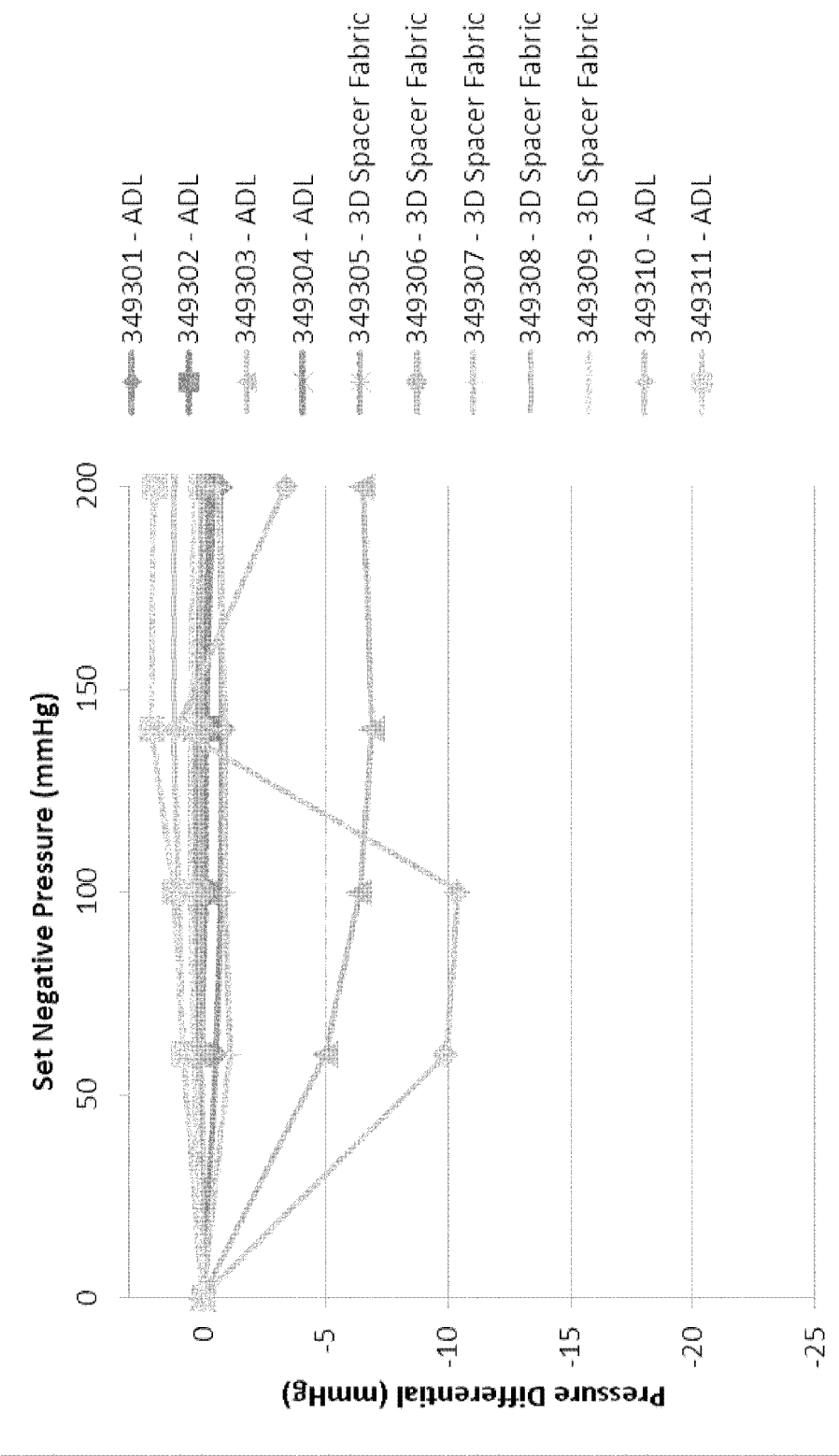
Figure 15G:
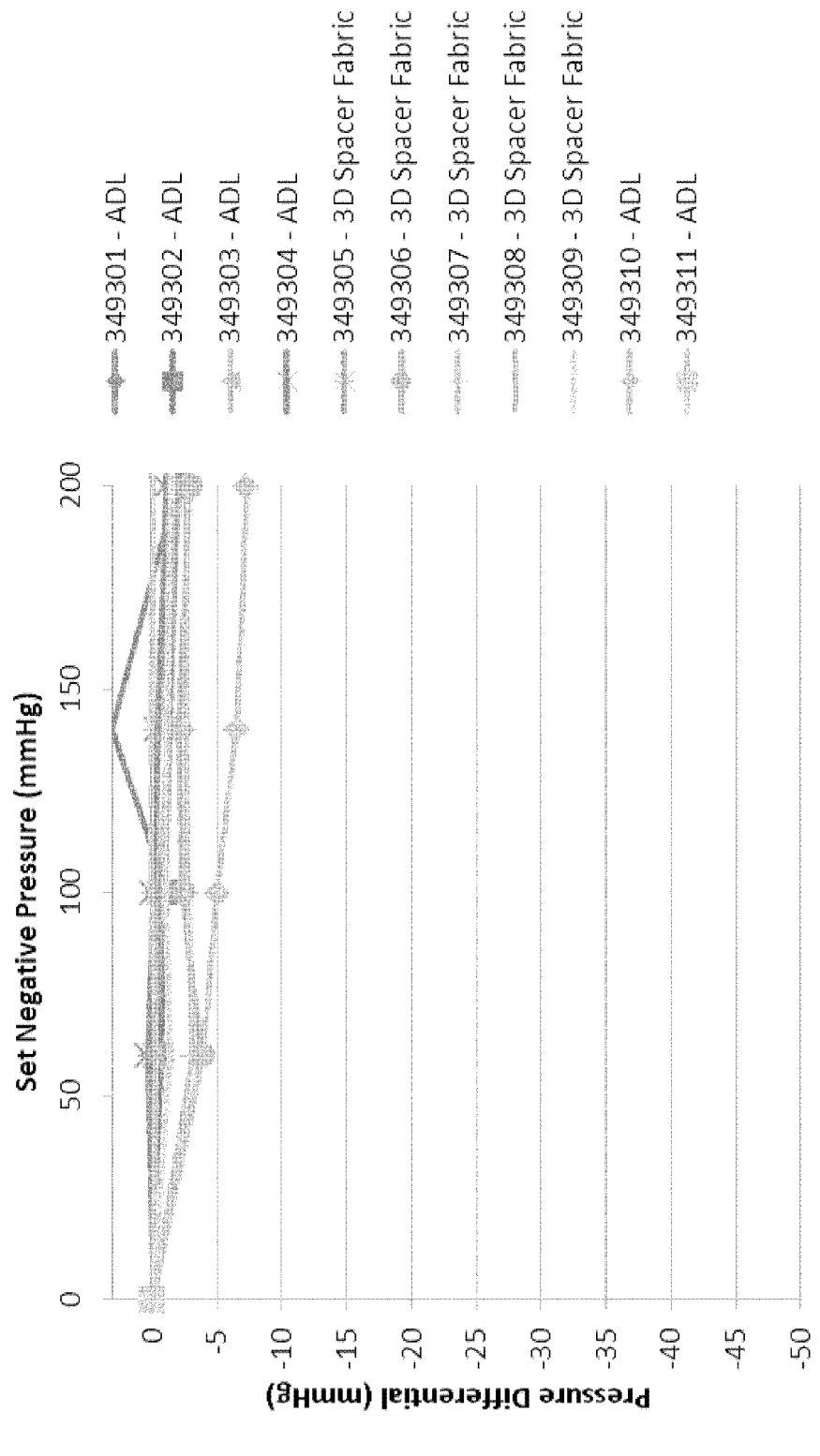
Figure 15H:
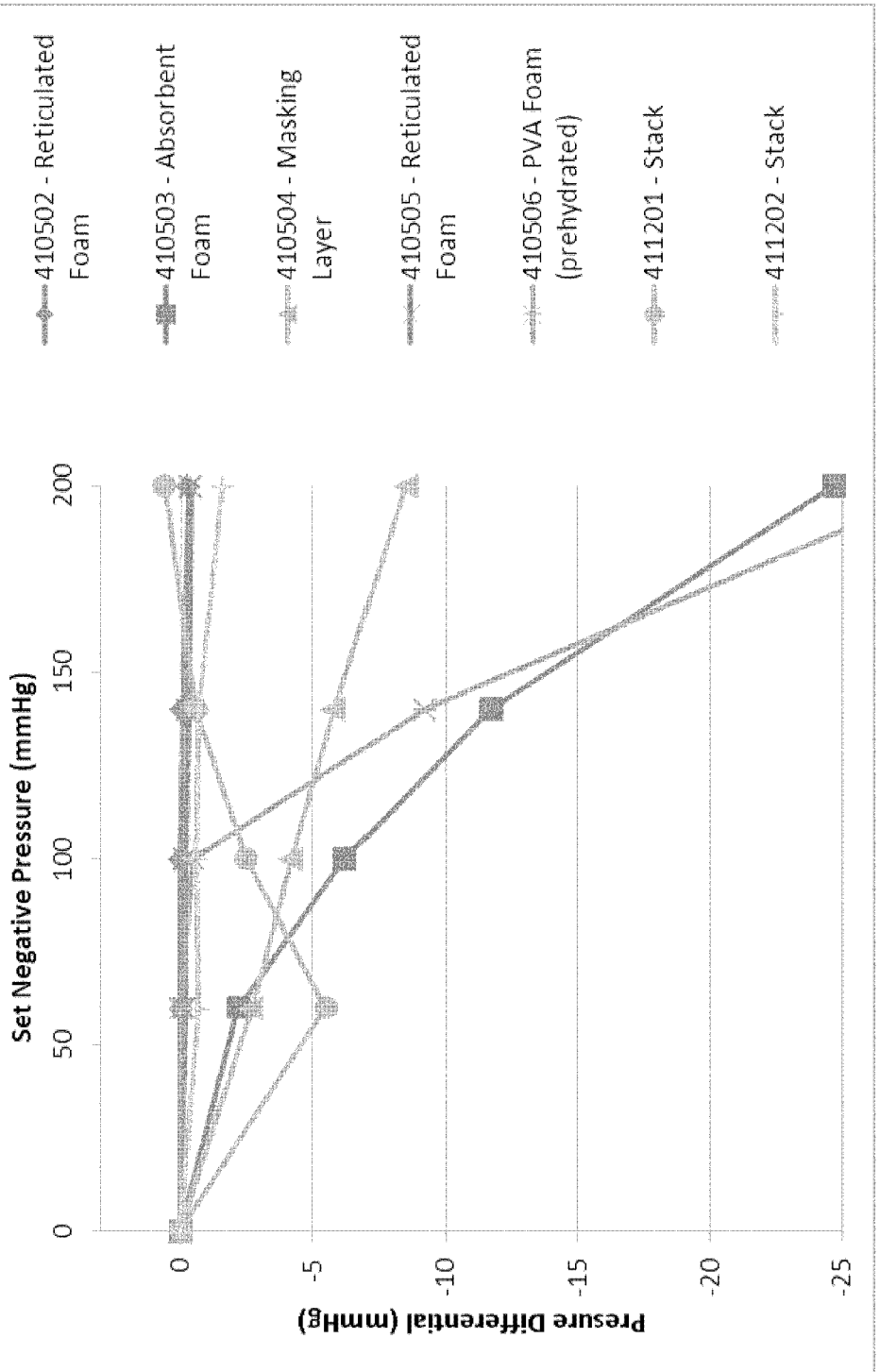
Figure 15I:
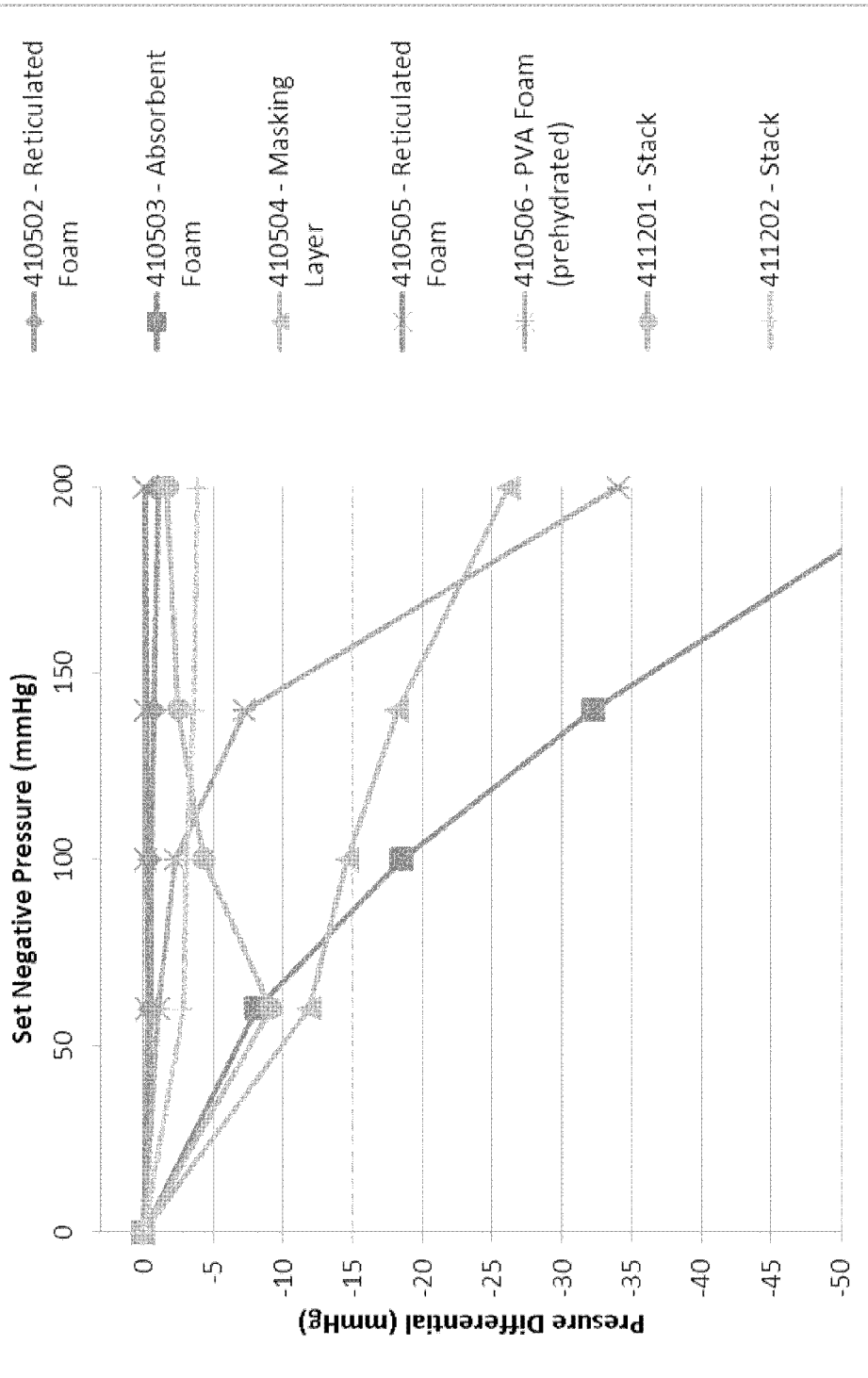
Figure 15J:
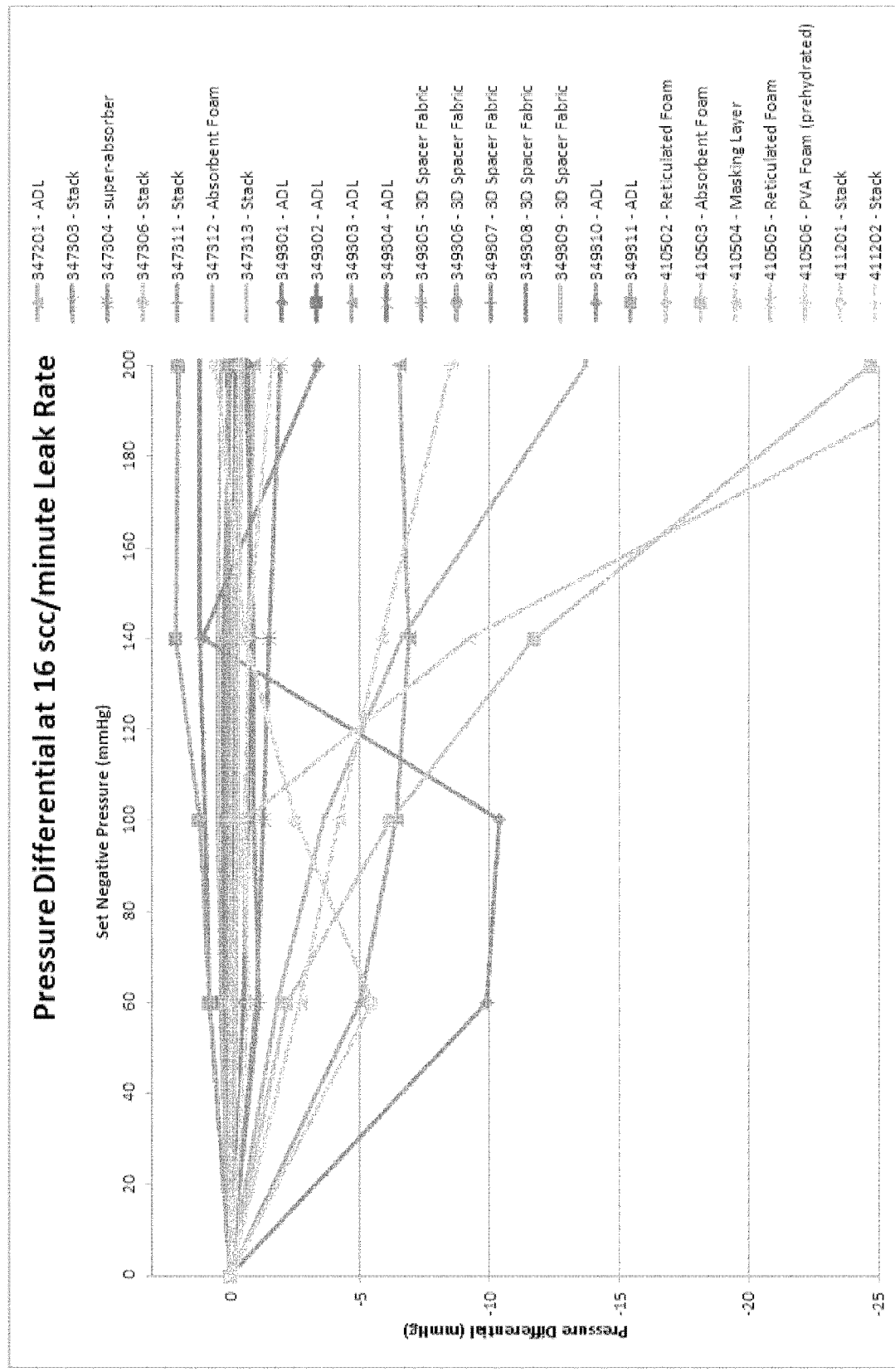
Figure 15K:
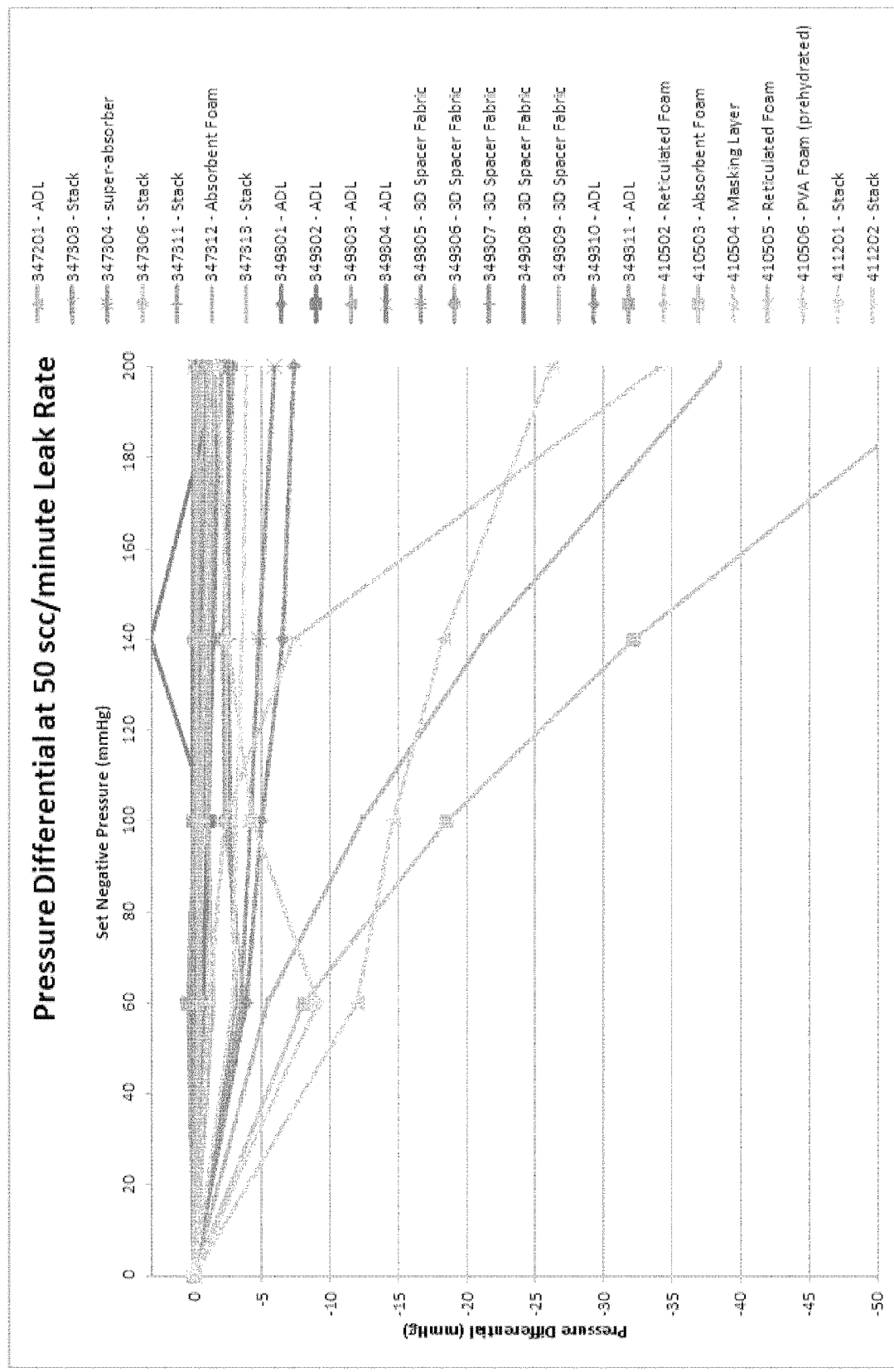
Figure 15L:
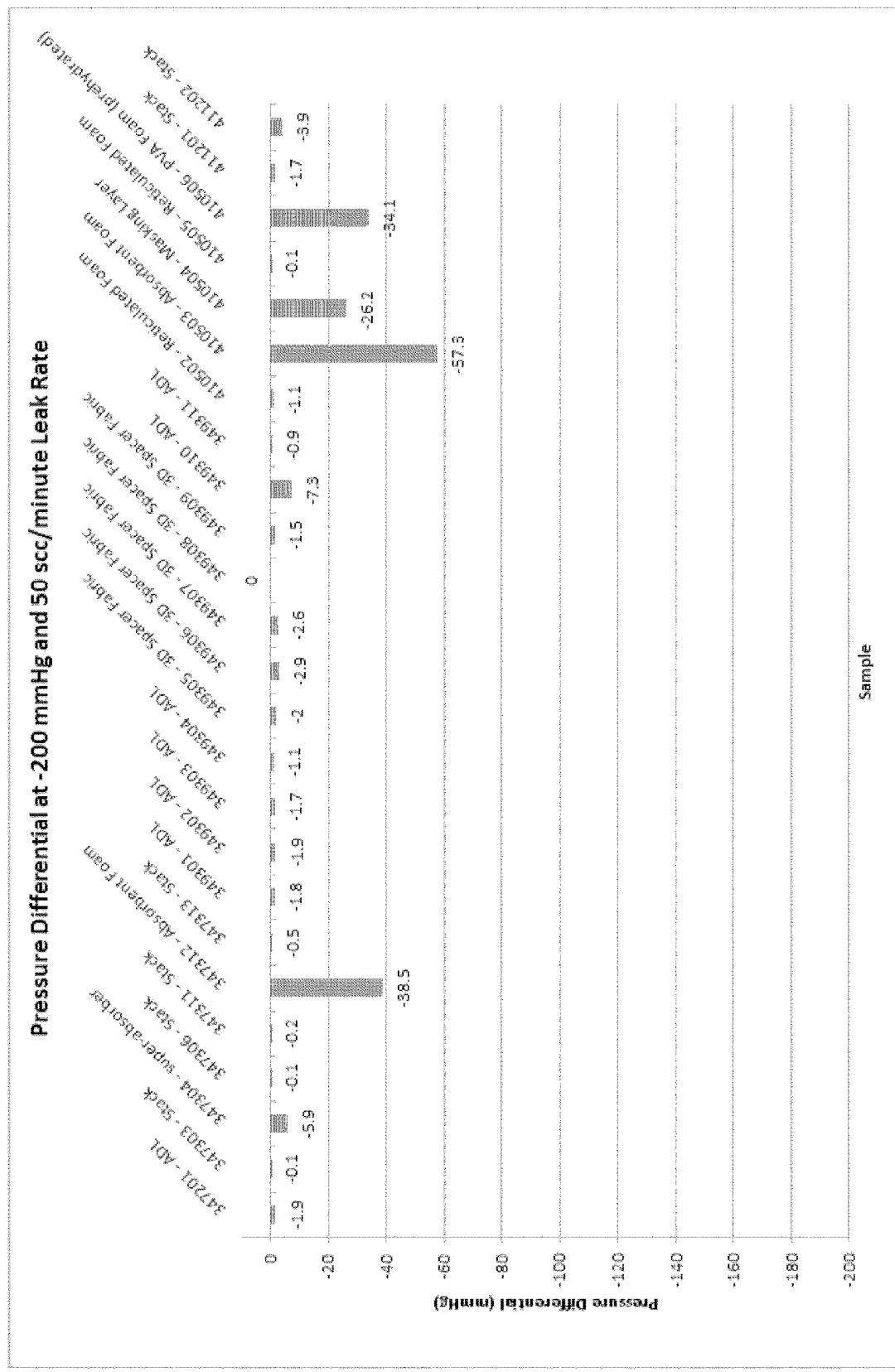
Figure 16A:
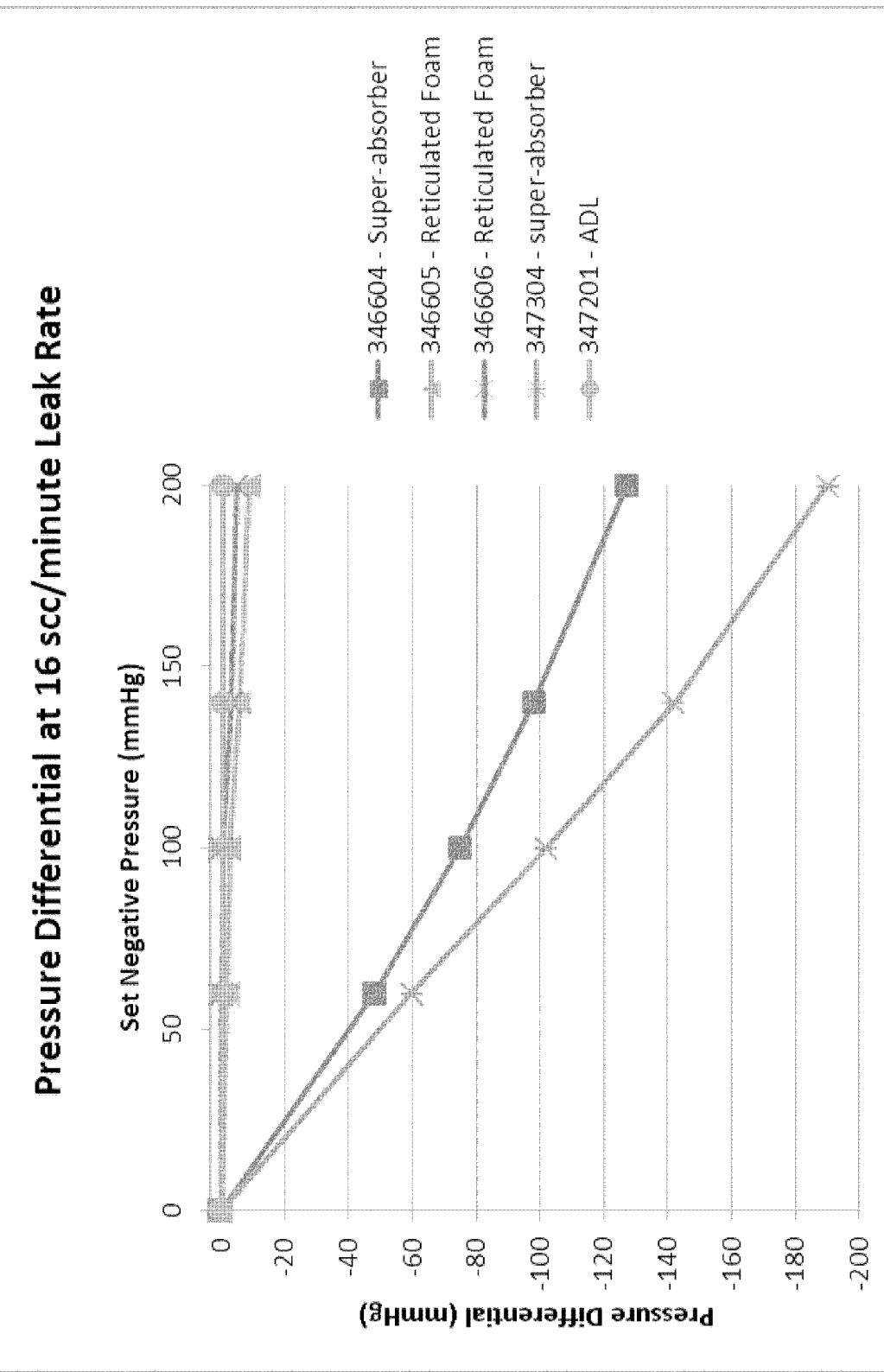
FIGS. 16A-16J illustrate differential pressure results of wet testing various materials for bridge sections of a dressing.
Figure 16B:
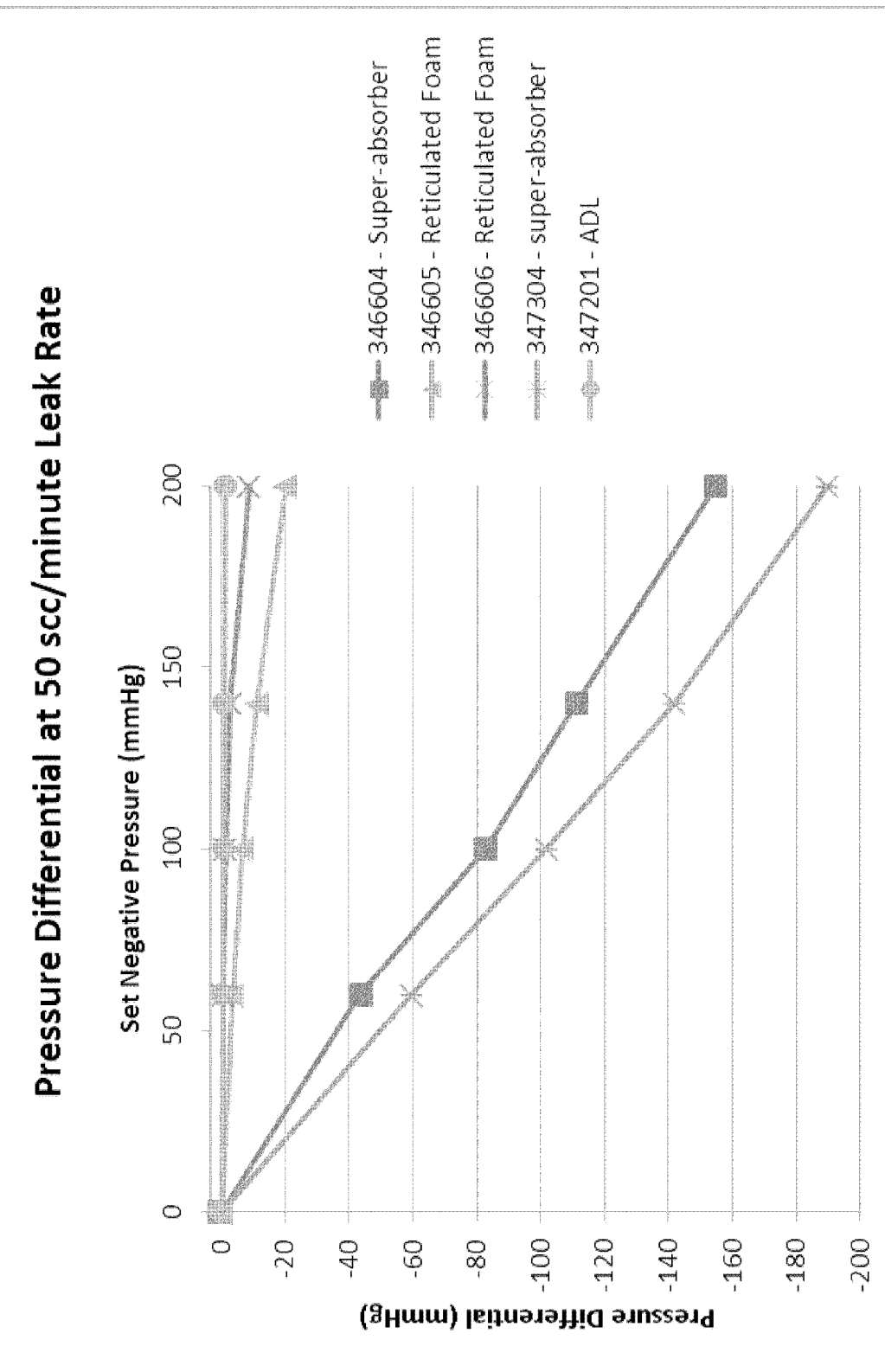
Figure 16C:
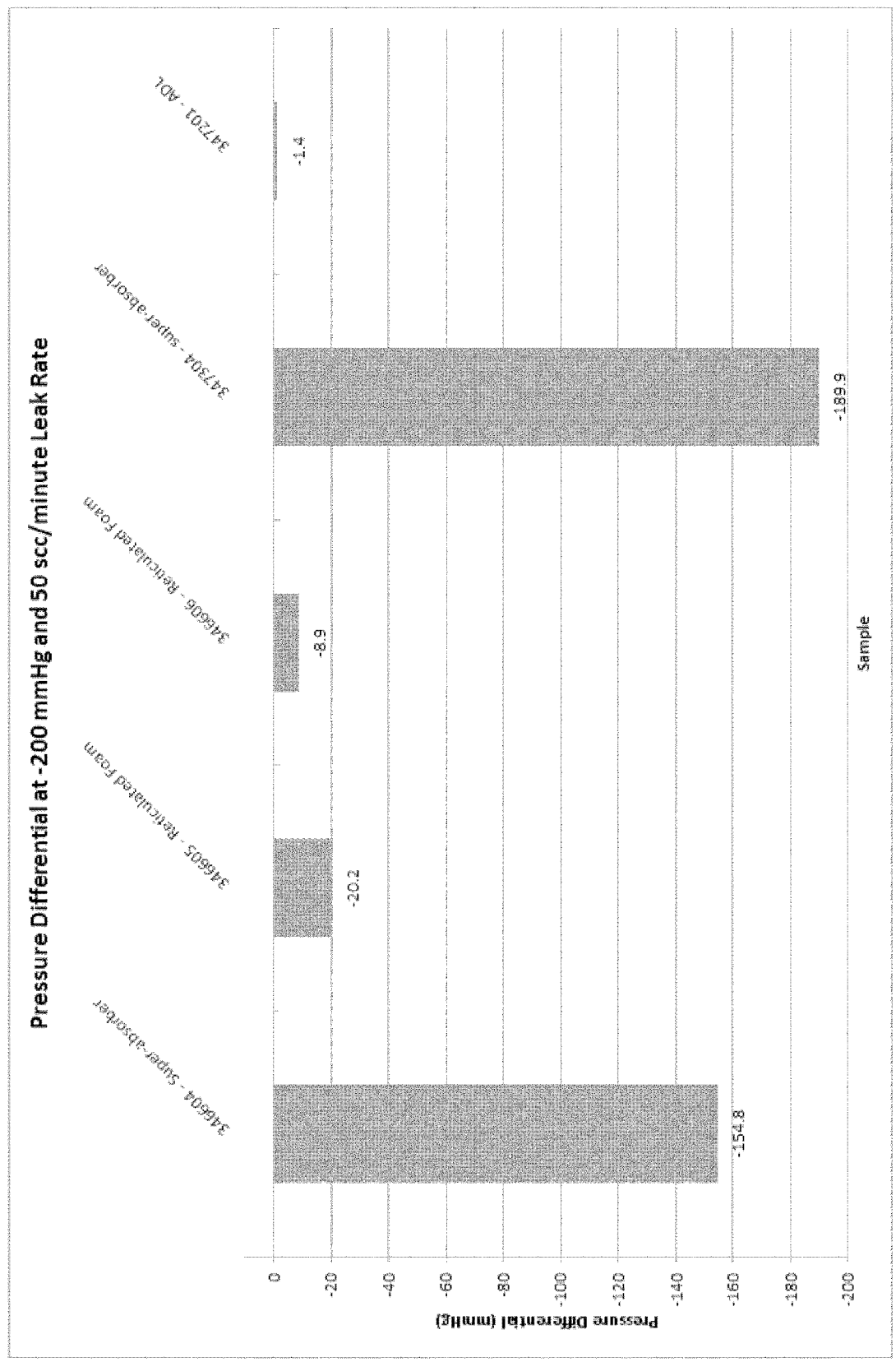

FIGS. 15A-15L illustrate differential pressure results of dry testing various materials for bridge sections of a dressing such as described herein, and FIGS. 16A-16C illustrate differential pressure results of wet testing various materials. The testing methodology was designed to assess the ability of dressing bridges to deliver negative pressure.

A wound model plate was constructed for both wet and dry testing of the sample dressings. In this testing embodiment, the wound model plate was an aluminum flat plate, however other materials can also provide suitable testing models. Two 2 mm±1 mm diameter holes were formed in the wound model plate to act as ports for negative pressure delivery and testing, with a first hole along a center line for placement of a sample dressing. A first segment of each hole was drilled in from the side of the plate, and a second segment connecting to the first segment was drilled in through the top of the plate. The path length from hole to hole (center to center) was approximately 22 mm±1 mm, corresponding to a minimum path length hole to hole (between proximal edges) of approximately 20 mm±1 mm. Other implementations of the testing method could reposition the port locations and distance. This testing model allows a negative pressure pump with settable pressures, for example RENASYS EZ in one embodiment, to draw negative pressure at a given set point down a first tube with a first in-line pressure sensor. This tube feeds into a first of the two ports. A second tube with a second in-line pressure sensor is arranged in a second of the two ports with a mass flow controller. The mass flow controller is capable of introducing a controlled leak into the system. As it is desirable to consider the leak rate as a function of volume per unit time, volume was set on the mass flow meter in units of standard cubic centimeters per minute (scc/minute, which can also be abbreviated to scc/m, scc/min or sccm). Any settable gas leak generator can be used in other testing implementations.

Each sample dressing was created having a wound contact layer, a cover layer, and the material or layered materials to be tested sandwiched between the wound contact layer and the cover layer. The wound contact layer and cover layer were sealed together around the material having a perimeter width of at least 2.5 cm or, in other embodiments, approximately 5 to 10 cm, where the width is measured from the inner materials to the edge of the sealed border. It will be appreciated, according to the layer material descriptions provided herein, that some of the materials tested can be "sided," that is asymmetric along a vertical axis. Accordingly, tested sample dressings were constructed with specific orientations of sided materials consistent with the material descriptions herein, though other orientations of the sided materials could be suitable for use in wound dressings.

For testing of the various sample dressings, each sample dressing sample was placed on the wound model with the first port approximately located along a center line of the dressing. The wound contact layer adhered to the wound model plate covering both of the first and second ports with the material to be tested so that negative pressure could be delivered to the material through the first port, so that a level of negative pressure within the material could be tested at the second port.

For each sample tested, a positive control was provided using an empty tube provided to connect the first port to the second port. In one implementation, the empty tube comprised a clear and flexible PVC tube, single bore with circular cross section, internal diameter of approximately 1.6 mm, outer diameter of approximately 3.2 mm and length of approximately 65 mm. The ends of this tube were pushed into the wound model ports affording snug fits between the outer surfaces of the tube and the inner surfaces of the ports.

For each sample the pressure differential between the two in-line sensors, i.e. the pressure drop across the sample, was measured at a variety of set points. The tested set points were 0, −60, −100, −140 & −200 mmHg, but the set points could be set to other values in other embodiments of the bridge testing. An air leak was introduced to each tested sample. In some tests, an air leak of approximately 16 scc/minute was introduced to represent what a negative pressure pump, for example PICO, can typically experience during its maintenance cycles. For example, negative pressure pumps can handle between about 12 scc/minute to about 20 scc/minute, with 16 scc/minute representing the average. In other tests, an air leak of approximately 50 scc/minute was introduced to test conditions approximating the 300 scc/minute to 350 scc/minute leak experienced during pump down. Other tests could be structured to test higher air leak rates as needed.

In order to calculate the pressure differential, first the positive control was measured.

The tests that were conducted, as discussed with respect to FIGS. 15A-15L, only allowed air into the system. Dealing with liquids such as wound exudate or irrigation fluids whilst simultaneously delivering negative pressure presents a different challenge to the bridges and is not accounted for in the test data of FIGS. 15A-15L. The test data of FIGS. 16A-16J accounts for liquid introduced into the tested system.

An embodiment of a dry differential pressure testing method, as implemented to produce the test data of FIGS. 15A-15L, can include the following steps:

1. Set-up the wound plate with the first hole connected to the pump via a gas pressure sensor and the second hole connected to the settable air leak via a second pressure sensor.

2. Stick the pad of a self-adhesive dressing sample across the two holes on the top of the plate so that the pad traverses across the two holes.
3. Zero each gas pressure sensor.
4. Record initial pressure differential (negative pressure side minus leak side).
5. Set air leak to 16 scc/minute and run pump at −60 mmHg negative pressure.
6. After 30 seconds, record pressure differential (negative pressure side minus leak side).
7. Record pressure differentials at set point pressures of −100, −140 and −200 mmHg in addition to −60 mmHg.
8. Record initial pressure differential (negative pressure side minus leak side).
9. Set air leak to 50 scc/minute and run pump at −60 mmHg negative pressure.
10. After 30 seconds, record pressure differential (negative pressure side minus leak side).
11. Record pressure differentials at set point pressures of −100, −140 and −200 mmHg in addition to −60 mmHg.
12. Repeat for all test samples.

An embodiment of a wet differential pressure testing method, as implemented to produce the test data of FIGS. 16A-16C, can include the following steps:

1. Set-up the wound plate with the first hole connected to the pump via a gas pressure sensor and the second hole connected to the settable air leak via a second pressure sensor.
2. Stick the pad of a self-adhesive dressing sample across the two holes on the top of the plate so that the pad traverses across the two holes.
3. Replace leak tube with a syringe containing 5.4 g saline.
4. Switch on pump (set to approximately −80 mmHg) to deliver negative pressure to the sample.
5. Allow substantially all of the saline to pass through the sample over approximately a 5 minute period.
6. Remove syringe and allow negative pressure to evacuate liquid from sample and tubes if unblocked, and otherwise leave saline in the sample and tubes, then turn pump off
7. Reattach leak tube with its pressure sensor.
8. Zero each gas pressure sensor.
9. Record initial pressure differential (negative pressure side minus leak side).
10. Set air leak to 16 scc/minute and run pump at −60 mmHg negative pressure.
11. After 30 seconds, record pressure differential (negative pressure side minus leak side).
12. Record pressure differentials at set point pressures of −100, −140 and −200 mmHg in addition to −60 mmHg.
13. Record initial pressure differential (negative pressure side minus leak side).
14. Set air leak to 50 scc/minute and run pump at −60 mmHg negative pressure.
15. After 30 seconds, record pressure differential (negative pressure side minus leak side).
16. Record pressure differentials at set point pressures of −100, −140 and −200 mmHg in addition to −60 mmHg.
17. Repeat for all test samples.

Prior to each run or prior to each day of testing, the in-line pressure sensors can be calibrated and the same data for a negative control (top plate holes blocked with self-adhesive film) and positive control (open tube connecting the two top holes in the plate) can be recorded.

An embodiment of a data processing method for calculating and plotting the negative pressure differential across a portion of a sample dressing at different set points can include the following steps:

1. Zero adjustment—for each individual run (including controls and test samples) subtract the zero pressure reading from each of the data readings in that run.
2. Baseline correction—to each (zero adjusted) data point in a test sample run subtract the (zero adjusted) positive control data point at the corresponding pressure setting.
3. Plot set pressure versus recorded differential pressure (after subtraction of zero pressure readings and subtraction of positive control).

The charts illustrated in FIGS. 15A-15L and 16A-16J will be discussed in conjunction with the Table 1, below, that includes the material or layered materials represented by the numbered legends in FIGS. 15A-15L and 16A-16J. For at least some of the tested material or materials indicated by the various legend numbers in Table 1, the dimensions of height, width, and cross sectional area specified may be approximate. For example, two, three, or more sample dressings of approximately the same dimensions were made for at least some of the tested materials, and the listed dimensions represent an approximation of a mean value of the material dimensions for the sample dressings tested for that material. In addition, all sample measurements were taken using calibrated digital calipers. In the case of compressible materials, the measurements reported are those of the uncompressed materials. Where variations in height readings were noted on a compressible material, height was recorded at 3 points along the fluid path and the mean was reported. In all cases width was recorded at 3 points along the fluid path and the mean reported. In considering the mean width of a sample it is implicit that the variation in width between readings is tolerable without any significant narrowings or constrictions along the fluid path.

As used in Table 1, "spacer" refers to an embodiment of spacer layer material of 200-220 g/m$^2$ (or approximately 200-220 g/m$^2$) Baltex 3D-knit fabric. DryWeb TDL2 refers to a 55 gsm (or approximately 55 gsm) Libeltex BVBA material that can be used for an ADL in the dressings described herein. SlimCore TL4 refers to a 150 gsm (or approximately 150 gsm) Libeltex BVBA material that can also be used for an ADL in the dressings described herein. Another possible ADL material tested and listed in Table 1 is MH080.121 a Glatfelter material slit to a width of 250 mm or approximately 250 mm. MH460.101 refers to a 460 gsm (or approximately 460 gsm) Glatfelter superabsorbent material that can be slit to a width of 250 mm. Masking layer, as used in Table 1, refers to a 70 gsm (or approximately 70 gsm) Don & Lowe blue woven material. DT360.100 refers to an approximately 360 gsm Glatfelter superabsorbent airlaid material including cellulose fibers with superabsorbent particles. Reticulated PU foam refers to an open-cell polyurethane foam, while PU foam refers to an open-cell foam that has not been reticulated. The configuration of dressing sample 347306 approximates the layer configuration illustrated in FIGS. 4A-4D. Basis weights reported refer to nominal basis weights and typically have a ±10% tolerance. "Stack" refers to the testing of multiple materials in a single arrangement. Where multiple materials were tested in one sample dressing, the materials are listed in order of top to bottom, for the tested arrangement.

TABLE 1

| Legend No. | Material(s) | Mean height (mm) | Mean width (mm) | Mean cross sectional area (mm2) |
|---|---|---|---|---|
| 346601—3D Spacer Fabric | Baltex 7970, weft knitted polyester spacer layer fabric, 210 gsm | 2 | 14 | 27 |
| 346602—3D Spacer Fabric | Baltex 7970, weft knitted polyester spacer layer fabric, 210 gsm | 2 | 3 | 7 |
| 346603—3D Spacer Fabric | Baltex 7970, weft knitted polyester spacer layer fabric, 210 gsm | 2 | 1 | 3 |
| 346604—Super-absorber | Glatfelter Inc., DT360.100, thermally bonded air-laid with super-absorbent powder and cellulose fibres, 360 gsm | 4 | 4 | 14 |
| 346605—Reticulated Foam | Smith & Nephew, RENASYS-F Foam, reticulated, open-cell, polyurethane foam | 5 | 3 | 15 |
| 346606—Reticulated Foam | Smith & Nephew, RENASYS-F Foam, reticulated, open-cell, polyurethane foam | 5 | 7 | 36 |
| 347201—ADL | Libeltex BVBA, SlimCore TL4, triple layered ADL, hydrophilic PET and bicomponent fibres, through air bonded web, 150 gsm | 2 | 11 | 27 |
| 347202—ADL | Libeltex BVBA, SlimCore TL4, triple layered ADL, hydrophilic PET and bicomponent fibres, through air bonded web, 150 gsm | 2 | 4 | 10 |
| 347204—ADL | Libeltex BVBA, DryWeb TDL2, through air bonded web, 55 gsm | 2 | 21 | 40 |
| 347205—ADL | Libeltex BVBA, DryWeb TDL2, through air bonded web, 55 gsm | 1 | 3 | 3 |
| 347206—3D Spacer Fabric | Baltex 7970, weft knitted polyester spacer layer fabric, 210 gsm | 2 | 15 | 31 |
| 347207—Stack | Libeltex BVBA, SlimCore TL4, triple layered ADL, hydrophilic PET and bicomponent fibres, through air bonded web, 150 gsm | 3 | 18 | 51 |
|  | Baltex 7970, weft knitted polyester spacer layer fabric, 210 gsm (smaller footprint than ADL) | 2 | 14 | 26 |
| 347301—Stack | Libeltex BVBA, DryWeb TDL2, through air bonded web, 55 gsm | 1 | 22 | 28 |
|  | Baltex 7970, weft knitted polyester spacer layer fabric, 210 gsm (smaller footprint than ADL) | 2 | 12 | 24 |
| 347302—Masking Layer | Don & Low Ltd Non Wovens, PP non woven fabric, blue, thermally bonded, 70 gsm | 0.4 | 14 | 6 |
| 347303—Stack | Don & Low Ltd Non Wovens, PP non woven fabric, thermally bonded, 70 gsm | 0.4 | 15 | 6 |
|  | Baltex 7970, weft knitted polyester spacer layer fabric, 210 gsm(smaller footprint than masking layer) | 2 | 11 | 20 |
| 347304—super-absorber | Glatfelter Falkenhagen GmbH, MH460.101, multibonded airlaid nonwoven containing super-absorbent powder, laminated against cellulose tissue, 460 gsm | 2 | 10 | 18 |
| 347305—Super-absorber | Glatfelter Falkenhagen GmbH, MH460.101, multibonded airlaid nonwoven containing super-absorbent powder, laminated against cellulose tissue, 460 gsm | 2 | 3 | 6 |
| 347306—Stack | Don & Low Ltd Non Wovens, PP non woven fabric, blue, thermally bonded, 70 gsm | 0.4 | 14 | 6 |
|  | Glatfelter Falkenhagen GmbH, MH460.101, multibonded airlaid nonwoven containing super-absorbent powder, laminated against cellulose tissue, 460 gsm | 2 | 14 | 25 |
|  | Glatfelter Falkenhagen GmbH, MH080.121, multibonded airlaid nonwoven | 1 | 15 | 11 |
|  | Baltex 7970, weft knitted polyester spacer layer fabric, 210 gsm (smaller footprint than upper layers) | 2 | 11 | 19 |
| 347308—ADL | Glatfelter Falkenhagen GmbH, MH080.121, multibonded airlaid nonwoven | 1 | 15 | 11 |
| 347309—ADL | Glatfelter Falkenhagen GmbH, MH080.121, multibonded airlaid nonwoven | 1 | 5 | 4 |
| 347310—Super-absorber | Glatfelter Inc., DT360.100, thermally bonded air-laid with super-absorbent powder and cellulose, 360 gsm | 3 | 14 | 47 |
| 347311—Stack | Glatfelter Inc., DT360.100, thermally bonded air-laid with super-absorbent powder and cellulose fibres, 360 gsm | 3 | 14 | 46 |
|  | Baltex 7970, weft knitted polyester spacer layer fabric, 210 gsm (smaller footprint than upper layer) | 2 | 10 | 18 |

TABLE 1-continued

| Legend No. | Material(s) | Mean height (mm) | Mean width (mm) | Mean cross sectional area (mm2) |
|---|---|---|---|---|
| 347312— Absorbent Foam | Smith & Nephew, Allevyn foam, from bulk, with a non-adhesive perforated wound contact layer (WCL) laminated to the top and bottom surfaces (WCL is the same as applied to the ProGuide Wound Contact Layer (WCL) surfaces) | 10 | 10 | 99 |
| 347313—Stack | Glatfelter Inc., DT360.100, thermally bonded air-laid with super-absorbent powder and cellulose fibres, 360 gsm | 4 | 11 | 40 |
| | Smith & Nephew, RENASYS-F Foam, reticulated, open-cell, polyurethane foam | 5 | 10 | 52 |
| 349301—ADL | Shalag Nonwovens, ST6CTPH90G, ADL, 90 gsm (longitudinal axis of the sample in line with the visually predominate fibre orientation of the distribution layer. Distribution layer orientated next to top film.) | 2 | 10 | 24 |
| 349302—ADL | Shalag Nonwovens, STAHTCT8OL, ADL, 80 gsm (Distribution layer orientated next to top film.) | 1 | 11 | 16 |
| 349303—ADL | Shalag Nonwovens, ST6CT8H65, ADL, 65 gsm (Distribution layer orientated next to top film.) | 3 | 9 | 26 |
| 349304—ADL | Shalag Nonwovens, ST6NT8H75, ADL, 75 gsm (Distribution layer orientated next to top film.) | 4 | 10 | 44 |
| 349305—3D Spacer Fabric | Apex Mills, 3D Spacer Fabric, DNB198A, polyester, 270 gsm (Face with larger holes orientated next to top film) | 2 | 10 | 21 |
| 349306—3D Spacer Fabric | Apex Mills, 3D Spacer Fabric, DNB197, polyester, 670 gsm | 6 | 10 | 60 |
| 349307—3D Spacer Fabric | Heathcote Fabrics Limited, SpaceTec, 2.5 mm gauge, polyester, 430 gsm (Face with larger holes orientated next to top film) | 3 | 10 | 25 |
| 349308—3D Spacer Fabric | Heathcote Fabrics Limited, SpaceTec, 3 mm gauge, polyester, 320 gsm (Face with larger holes orientated next to top film) | 3 | 10 | 30 |
| 349309—3D Spacer Fabric | Apex Mills, 3D Spacer Fabric, DNB22(6), polyester (Face with larger holes orientated next to top film) | 3 | 9 | 29 |
| 349310—ADL | Libeltex BVBA, DryWeb T28F, monolayered AQL, hydrophilic PET and bicomponent fibres, through air bonded web, 50 gsm | 1 | 10 | 14 |
| 349311—ADL | Libeltex BVBA SlimCore TL4, triple layered ADL, hydrophilic PET and bicomponent fibres, through air bonded web, 90 gsm | 3 | 10 | 29 |
| 410502— Reticulated Foam | Smith & Nephew, RENASYS-F Foam, reticulated, open-cell, polyurethane foam | 5 | 10 | 53 |
| 410503— Absorbent Foam | Smith & Nephew, Allevyn foam, from bulk | 6 | 10 | 61 |
| 410504—Masking Layer | Don & Low Ltd Non Wovens, PP non woven fabric, blue, thermally bonded, 70 gsm | 0 | 10 | 5 |
| 410505— Reticulated Foam | Smith & Nephew, RENASYS-F Foam, reticulated, open-cell, polyurethane foam | 10 | 10 | 100 |
| 410506—PVA Foam (prehydrated) | KCI, WhiteFoam, prehydrated open cell PVA foam | 10 | 10 | 96 |
| 411201—Stack | Glatfelter Inc., DT360.100, thermally bonded air-laid with super-absorbent powder and cellulose fibres, 360 gsm | 4 | 14 | 57 |
| | Smith & Nephew, RENASYS-F Foam, reticulated, open-cell, polyurethane foam (smaller footprint than upper layer) | 11 | 10 | 106 |
| 411202—Stack | Glatfelter Inc., DT360.100, thermally bonded air-laid with super-absorbent powder and cellulose fibres, 360 gsm | 4 | 15 | 57 |
| | Smith & Nephew, RENASYS-F Foam, reticulated, open-cell, polyurethane foam (smaller footprint than upper layer) | 13 | 10 | 131 |

A top film of EU33 PU IV3000 film with a K5 pattern spread was typically used for the top film of each tested sample dressing in Table 1, with the exception of samples that failed due to puncture that were reinforced with EU30 Opsite Flexigrid over the leaks, as well as the sample dressing 347206 that replaced the EU33 PU IV3000 film with the thicker, tougher, and less hydrophilic EU30 Opsite Flexigrid. Perforated silicone, specifically A8/EU30 PU film, was used for the wound contact layer. However, the dressings disclosed herein are not limited to the use of these materials for the top film and the wound contact layer, as any materials with similar properties to those tested can be implemented in various embodiments.

The tested materials were deemed to satisfy the testing criteria and be suitable for bridges if able to maintain negative pressure transmission under typical ranges of negative pressure. For example, one pump operates in a range of approximately −60 mmHg to −100 mmHg, and another pump embodiment operates in a range of approximately −60 mmHg to −200 mmHg. According to first testing criteria, a tested material was deemed to fail, or be unsuitable for bridges, if when assessed against a set point pressure in the range −60 to −200 mmHg with an air leak of 50 scc/minute a negative pressure less than approximately −40 mmHg (that is, closer to zero) was being transmitted to any intended part of the dressing. According to second testing criteria, materials having a pressure differential of approximately −25 mmHg or less (that is, closer to zero) at a set point of −200 mmHg with a leak rate of 50 scc/minute were determined to be clinically appropriate. According to third testing criteria, materials having a pressure differential of approximately −5 mmHg or less (that is, closer to zero) at a set point of −200 mmHg with a leak rate of 50 scc/minute were determined to be clinically appropriate. Such testing criteria account for the possibility that test results can include noise of ±3 mmHg.

One of the above testing criteria can be selected to determine appropriate materials for a particular dressing based on a variety of characteristics of the dressing including dressing shape, dressing dimensions, number of ports, port locations, number of bridges, bridge dimensions, or the like. As an example, the more robust transmission materials satisfying the third testing criteria could be used in some embodiments for long dressings having multiple bridging portions to reduce the compounding pressure drop effects of multiple bridging portions, for dressings with narrow bridges, dressings having a large number of bridges, or dressings having relatively long distances between ports. As discussed above, multiple port locations along a long dressing can also be used to maintain sufficient levels of negative pressure. As another example, materials satisfying the second criteria (and also the more restrictive first criteria) can be suitable for dressings with wider bridges, a greater number of ports, and/or smaller coverage areas.

Turning now to FIGS. 15A-15L, testing data for dry testing a plurality of sample dressings at a plurality of pressure set points is illustrated for test systems having air leaks of 16 scc/minute and 50 scc/minute, respectively.

Referring to FIG. 15A, the measured pressure differential (in mmHg) is illustrated for sample dressings 346601, 346602, 346603, 346604, 346605, 346606, 347201, 347202, 347204, 347205, 347206, and 347207 as a function of set negative pressure with a 16 scc/minute leak rate. Generally, if a spacer layer was in direct contact with the top film layer, the top film layer was punctured by the spacer layer filaments, producing a leak that was sealed using a layer of additional, thicker film to continue the testing. Sample dressing 346604 experienced decreased negative pressure transmission performance due to compression of the Airlaid SAP. Sample dressing 347205, constructed from Airlaid SAP having a smaller cross sectional area than the material used in sample dressing 346604, experienced failure due to compression of the Airlaid SAP under the set negative pressure points. The other tested materials generally performed well, as indicated by proximity of the corresponding plot line to the zero pressure differential axis.

FIG. 15B depicts the measured pressure differential of the same set of sample dressings as in FIG. 15A, however as a function of set negative pressure with a 50 scc/minute leak rate. Generally speaking, the higher leak rate reduced the negative pressure transmission performance of all tested materials, however all of the illustrated sample dressings maintained satisfactory levels of negative pressure throughout the dressing with the exception of sample dressings 346604 and 347205.

Turning to FIG. 15C, the measured pressure differential of a second set of sample dressings is depicted as a function of set negative pressure with a 16 scc/minute leak rate. The second set of sample dressings includes 347301, 347302, 347303, 347304, 347305, 347306, 347308, 347309, 347310, 347311, 347312, and 347313 from Table 1. As illustrated by the corresponding plot line, the masking layer tested in sample dressing 347302 was not suitable for transmission of sufficient negative pressure levels. The non-reticulated PU foam was also not suitable, as illustrated by the plot line corresponding to sample dressing 347312, and experienced significantly reduced performance as compared to reticulated PU foam. Dressing 347308, employing MH080.121, corresponds to a plot line trending downward, and the reduced-width MH080.121 of sample dressing 347309 also experienced unsuitable levels of negative pressure due to the pressure differential.

FIG. 15D illustrates test results for the second set of sample dressings also depicted in FIG. 15C, however using a 50 scc/minute leak rate. The plot lines of test data corresponding to sample dressings 347301, 347303, 347306, 347311, and 347313 all remain close to the zero pressure differential axis, indicating good performance with respect to negative pressure transmission.

FIG. 15E illustrates the pressure differential at a set point negative pressure of −200 mmHg and 50 scc/minute leak rate after subtraction of positive control for each of the dry tested sample dressings.

Turning to FIG. 15F, the measured pressure differential of another set of sample dressings is depicted as a function of set negative pressure with a 16 scc/minute leak rate. This set of sample dressings includes 349301, 349302, 349303, 349304, 349305, 349306, 349307, 349308, 349309, 349310 and 349311. With respect to both the ADL tested in sample 349303 and the ADL tested in sample 349310, the corresponding plot lines demonstrate that the pressure differential exceeds −5 mmHg at points across the range of negative pressure set points assessed. Accordingly, such materials would not be most suitable for use as a transmission layer. The plot lines of test data corresponding to sample dressings 349301, 349302, 349304, 349305, 349306, 349307, 349308, 349309 and 349311 all remain close to the zero pressure differential axis, indicating good performance of the materials or stacks tested in these samples with respect to negative pressure transmission at the specified heights and widths.

FIG. 15G illustrates test results for the same set of sample dressings depicted in FIG. 15F, however using a 50 scc/minute leak rate. With respect to the ADL tested in sample 349310, the corresponding plot line demonstrates that the pressure differential exceeds −5 mmHg at points across the range of negative pressure set points assessed, in line with the observation made for this sample at the lower leak rate. The plot lines of test data corresponding to sample dressings 349301, 349302, 349303, 349304, 349305, 349306, 349307, 349308, 349309 and 349311 all remain close to the zero pressure differential axis, indicating good performance of the materials or stacks tested in these samples with respect to negative pressure transmission at the specified heights and widths.

Turning to FIG. 15H, the measured pressure differential of another set of sample dressings is depicted as a function of set negative pressure with a 16 scc/minute leak rate. This set of sample dressings includes 410502, 410503, 410504, 410505, 410506, 411201 and 411202. As illustrated by the corresponding plot line an increase in the pressure differential was observed for sample 411201, a stack containing a reticulated PU foam transmission layer with dimensions of 10 mm mean width and 11 mm mean height, at a set-point of −60 mmHg, however this increased pressure differential abated at higher negative pressure set points. Sample 411202, a stack containing a reticulated PU foam transmission layer with slightly larger dimensions of 10 mm mean width and 13 mm mean height did not follow a similar trend to 411201 and showed no significant increase in pressure differential across the range of negative pressure set points tested. As illustrated by the corresponding plot line an increase in the pressure differential was observed for sample 410503, containing an absorbent PU foam. As illustrated by the corresponding plot line an increase in the pressure differential was observed for sample 410504, containing a masking layer, this result was probably driven largely by the fact that the masking layer has such a low profile (0.4 mm mean height). As illustrated by the corresponding plot line an increase in the pressure differential was observed for sample 410506 a prehydrated PVA foam, and according to the testing criteria this material appeared acceptable at negative pressure set points up to and including −100 mmHg but then demonstrated a significant increase in the pressure differential at negative pressure set points above this. The plot lines of test data corresponding to sample dressings 410502, 410505 and 411202 all remain close to the zero pressure differential axis, indicating good performance with respect to negative pressure transmission at the specified heights and widths for each material or stack.

FIG. 15I illustrates test results for the same set of sample dressings depicted in FIG. 15H, however using a 50 scc/minute leak rate. With respect to the absorbent PU foam tested in sample 410503, the masking layer tested in sample 410504, and the prehydrated PVA foam tested in sample 410506, the corresponding plot lines demonstrate that the pressure differential exceeds −5 mmHg at points across the range of negative pressure set points assessed, in line with the observation made for this sample at the lower leak rate. As illustrated by the corresponding plot line an increase in the pressure differential was observed for sample 411201, a stack containing a reticulated PU foam transmission layer with dimensions of 10 mm mean width and 11 mm mean height, at a set-point of −60 mmHg, however this increased pressure differential abated at higher negative pressure set points, consistent with the observation made for this sample at the lower leak rate. The plot lines of test data corresponding to sample dressings 410502, 410505 and 411202 all remain close to the zero pressure differential axis, indicating good performance with respect to negative pressure transmission at the specified heights and widths for each material or stack.

Turning now to FIG. 15J, a comparison graph illustrates the performance of all samples, normalized to a width of 10 mm±1 mm, as a function of set negative pressure with a 16 scc/minute leak rate when dry tested. FIG. 15K illustrates test results for the same set of sample dressings depicted in FIG. 15J, however using a 50 scc/minute leak rate. Accordingly, FIGS. 15J and 15K allow for relative comparison of sample performance at a standardized width across the samples. Similar to the other pressure differential charts discussed herein, suitable transmission layer materials will demonstrate a pressure differential around or below approximately −5 mmHg at points across the range of negative pressure set points assessed.

FIG. 15L illustrates the pressure differential at a negative pressure set point of −200 mmHg and 50 scc/minute leak rate after subtraction of positive control for each of the width-normalized dry tested sample dressings of FIGS. 15J and 15K. Materials suitable for transmission layers, or stacks including at least one suitable transmission layer, are indicated by plots illustrating that a pressure differential of −160.0 mmHg or less was recorded. This can correspond to delivery of at least −40 mmHg therapy against a set point in the range −60 to −200 mmHg with an air leak of 50 scc/minute. In some scenarios, −40 mmHg can represent the minimum clinically acceptable level of wound therapy. Accordingly, delivery of less than −40 mmHg can result in clinically unacceptable levels of wound therapy in some scenarios. [0193] As indicated by the test results of FIGS. 15A-15L and the material specifications of Table 1, generally speaking, a dressing implementing the 3D knit spacer layer or reticulated foam as a transmission layer will experience low negative pressure differentials across bridging portions with widths as low as approximately 1 mm. Smaller widths than 1 mm using these materials, though possible for sufficient negative pressure transmission, were not included in the testing data due to limitations of the sample dressing construction process. Dressing embodiments implementing a non-woven transmission layer for bridging portions, such as the Libeltex ADL materials, can also experience low negative pressure differentials. In addition, materials suitable for bridging portions have good resiliency, in that such materials rebound after compression to allow for transmission of negative pressure. Other materials, in addition to the samples tested, offering the desired permeability to gas and liquid at a set width and/or height while under compression due to negative pressure can be suitable for use as a transmission layer.

Table 2 illustrates the raw data used to generate the charts of FIGS. 15A-15L.

TABLE 2

| | Leak rate (scc/min) 16 Pressures (mmHg) | | | | | Leak rate (scc/min) 50 Pressures (mmHg) | | | | |
|---|---|---|---|---|---|---|---|---|---|---|
| Ref | 0 | 60 | 100 | 140 | 200 Recorded dP (mmHg) | 0 | 60 | 100 | 140 | 200 |
| Day 1 | | | | | | | | | | |
| Positive Control | −0.1 | −2.8 | −4.5 | −6.3 | −8.9 | −0.1 | −3.1 | −4.9 | −6.7 | −9.2 |
| 346601 | 0.1 | −2.9 | −4.6 | −6.4 | −9 | 0.2 | −2.9 | −4.8 | −6.6 | −9.2 |
| 346602 | 0.7 | −2.6 | −4.5 | −6.4 | −9.3 | −0.7 | −2.9 | −4.8 | −6.8 | −9.8 |
| 346603 | 0.2 | −2.9 | −4.8 | −6.7 | −9.8 | 0.3 | −3.4 | −5.7 | −8.1 | −12.4 |
| 346604 | 0 | −3.3 | −5.6 | −8.9 | −13.2 | 0 | −5.9 | −13.2 | | −176.3 |
| 346605 | −3 | −6.2 | −8.2 | −10.3 | −13.7 | −2.8 | −7.6 | −10.4 | −13.3 | −18 |
| 346606 | −3 | −6.6 | −8.5 | −10.4 | −13.4 | −3 | −6.8 | −9 | −11.1 | −14.6 |
| 347201 | 0 | −3.2 | −5 | −6.9 | −9.7 | 0.2 | −3.6 | −5.7 | −7.7 | −10.8 |
| 347202 | 0.2 | −3.2 | −5.2 | −7.2 | −10.3 | 0.4 | −4.4 | −6.9 | −9.3 | −13 |
| 347204 | 0.2 | −3.3 | −5.4 | −7.4 | −10.3 | 0.3 | −4.3 | −6.9 | −9.2 | −12.6 |
| 347205 | 0 | −6.7 | −16 | −15.3 | −22.7 | 0.4 | 20.2 | −29.2 | −39 | −55.5 |
| 347207 | 0.1 | −3.1 | −5 | −6.9 | −9.6 | 0.2 | −3.4 | −5.3 | −7.2 | −10 |
| 347206 | 0.1 | −3.5 | −5.6 | −7.6 | −10.7 | 0.2 | −4.9 | −6.8 | −9 | −12.1 |
| Day2 | | | | | | | | | | |
| Negative Control | 0 | −65.7 | −108.6 | −150.6 | >−200 | | | | | |
| Positive Control | −0.1 | −3.2 | −5.1 | −7 | −9.8 | 0.2 | −3.2 | −5.2 | −7.1 | −9.9 |
| 347301 | −0.1 | −3.2 | −5.2 | −7.1 | −9.9 | 0 | −3.4 | −5.3 | −7.2 | −10 |
| 347302 | −0.1 | −12 | −16.8 | −19.5 | −32.5 | −0.1 | −19 | −32.5 | −40.4 | −53.1 |
| 347305 | −0.1 | −4.7 | −7.8 | −10.7 | −15 | −0.1 | −9.6 | −15 | −19.8 | −26.5 |
| 347304 | −0.2 | −4.3 | −6.5 | −8.6 | −11.8 | 0 | −6.9 | −9.6 | −12.1 | −16 |
| 347303 | 0 | −3.3 | −5.2 | −7.1 | −9.9 | 0.2 | −3.3 | −5.3 | −7.2 | −10 |
| 347306 | 0.1 | −3.1 | −5.1 | −7 | −9.8 | 0.2 | −3.2 | −5.2 | −7.1 | −10 |
| 347308 | 0.2 | −4.8 | −9.7 | −10.8 | −14.8 | 0.2 | −11.7 | −14.3 | −17 | −23.3 |
| 347309 | 0.1 | −6.1 | −9 | −12.1 | −17.1 | 0.2 | −13.2 | −18.2 | −23.6 | −32.2 |
| 347310 | 0.1 | −6.5 | −7.7 | −9.8 | −13.2 | 0.1 | −7.4 | −9 | −11.3 | −15.2 |
| 347311 | 0.1 | −3.2 | −5.2 | −7.1 | 10 | 0.1 | −3.3 | −5.4 | −7.3 | −10.2 |
| 347312 | 0 | −4.9 | −8.6 | −13.5 | −23.4 | 0 | −8.8 | −17.7 | −28.5 | −48.6 |
| 347313 | 0 | −3.3 | −5.3 | −7.2 | −10.1 | 0 | −3.5 | −5.6 | −7.5 | −10.6 |
| Day 4 | | | | | | | | | | |
| Negative Control | 0 | −64 | −105 | — | >−200 | | | | | |
| Positive Control | 0 | −1 | −1.1 | −1.4 | −2 | −0.1 | −0.8 | −0.8 | −1 | −1.6 |
| 349301 | 0 | −1.5 | −1.8 | −2.2 | −2.7 | 0.1 | −1.2 | −1.6 | −2.2 | −3.2 |
| 349302 | 0 | −0.6 | −1 | −1.5 | −2.2 | 0.1 | −1.2 | −1.7 | 2.3 | −3.3 |
| Day 5 | | | | | | | | | | |
| Negative Control | 0.1 | −62.8 | −104.2 | −144.1 | >−200 | | | | | |
| Positive Control | 0.1 | 0.4 | 0.7 | 1 | 1.5 | 0 | 0.2 | 0.5 | 0.8 | 1.3 |
| 349303 | 0 | −4.7 | −5.8 | −6 | −5.1 | 0 | 0.2 | 0.3 | 0.3 | −0.4 |
| 349304 | −0.1 | 0.3 | 0.4 | 0.7 | 0.9 | 0 | 0.5 | 0.5 | 0.4 | 0.2 |
| 349305 | −0.2 | 0.4 | 0.7 | 1 | 1.2 | −0.1 | −0.1 | −0.2 | −0.5 | −0.8 |
| 349306 | −0.1 | 0.3 | 0.6 | 0.9 | 1.4 | −0.2 | −3.8 | −2 | −1.5 | −1.8 |
| 349307 | −0.2 | −1 | −0.5 | −0.2 | 0.6 | 0.1 | −2.8 | −2.1 | −1.7 | −1.2 |
| 349308 | −0.1 | 1 | 1.5 | 2 | 2.5 | −0.2 | −0.3 | 0.4 | 0.7 | 1.1 |
| 349309 | 0 | 0.7 | 1.1 | 1.4 | 1.8 | 0.2 | −1 | −0.3 | −0.1 | 0 |
| 349310 | 0 | −9.6 | −9.8 | 2 | −2 | −0.2 | −3.9 | −4.7 | −5.9 | −6.2 |
| 349311 | −0.1 | 1 | 1.7 | 2.9 | 3.3 | 0.1 | 0.7 | 0.6 | 0.6 | 0.5 |
| Day 6: | | | | | | | | | | |
| Negative Control | 0.1 | −62.7 | −103.7 | −143.8 | >−200 | | | | | |
| Positive Control | 0.1 | 0.1 | 0.1 | 0.1 | −0.1 | 0.3 | 0.6 | 0.5 | 0.5 | 0.3 |
| 410502 | 0.2 | 0.2 | 0.2 | 0.1 | −0.3 | 0.3 | 0.1 | 0 | −0.3 | −0.8 |
| 410503 | 0.4 | −1.8 | −5.8 | −11.3 | −24.5 | 0.5 | −7.3 | −17.8 | −31.5 | −56.8 |
| 410504 | 0.4 | −2.3 | −3.8 | −5.4 | −8.3 | 0.2 | −11.4 | −14.2 | −17.8 | −26 |
| 410505 | 0.2 | 0 | 0 | −0.1 | −0.4 | 0.3 | 0.3 | 0.3 | 0.3 | 0.2 |
| 410506 | 0.2 | 0.2 | −0.3 | −9 | −29 | 0.1 | −0.7 | −2 | −7 | −34 |
| Day 7 | | | | | | | | | | |
| Negative Control | 1.4 | −60.6 | −101.4 | −141.2 | >−200 | | | | | |
| Positive Control | 1.3 | 0.5 | 0.3 | 0.2 | 0 | 0.5 | 0.3 | 0.2 | 0.1 | −0.1 |
| 411201 | 1.3 | −5 | −2.2 | −0.4 | 0.6 | 1.8 | −7.5 | −2.8 | −1.1 | −0.5 |
| 411202 | 1.8 | 0.3 | 0.2 | 0 | −1.1 | 2.1 | −1 | −1.3 | −1.9 | −2.4 |

Turning now to FIGS. 16A-16J, testing data for wet testing a plurality of sample dressings at a plurality of pressure set points is illustrated for test systems having air leaks of 16 scc/minute and 50 scc/minute, respectively.

Referring specifically to FIGS. 16A-16B, testing data for wet testing a plurality of sample dressings at a plurality of pressure set points is illustrated for test systems having air leaks of 16 scc/minute and 50 scc/minute, respectively. The samples of FIGS. 16A and 16B include a subset of the samples tested for FIGS. 15A and 15B, illustrating the performance of samples 346604, 346605, 346606, 347304, and 347201. As illustrated by the plot lines corresponding to the tested materials, the SlimCore TL4 of sample 347201 as well as two tested widths of the reticulated foam of samples 346605 and 346606 provided clinically appropriate pressure transmission even with wet testing.

FIG. 16C illustrates the pressure differential at a negative pressure set point of −200 mmHg and 50 scc/minute leak rate after subtraction of positive control for each of the wet tested sample dressings.

Figure 16D:
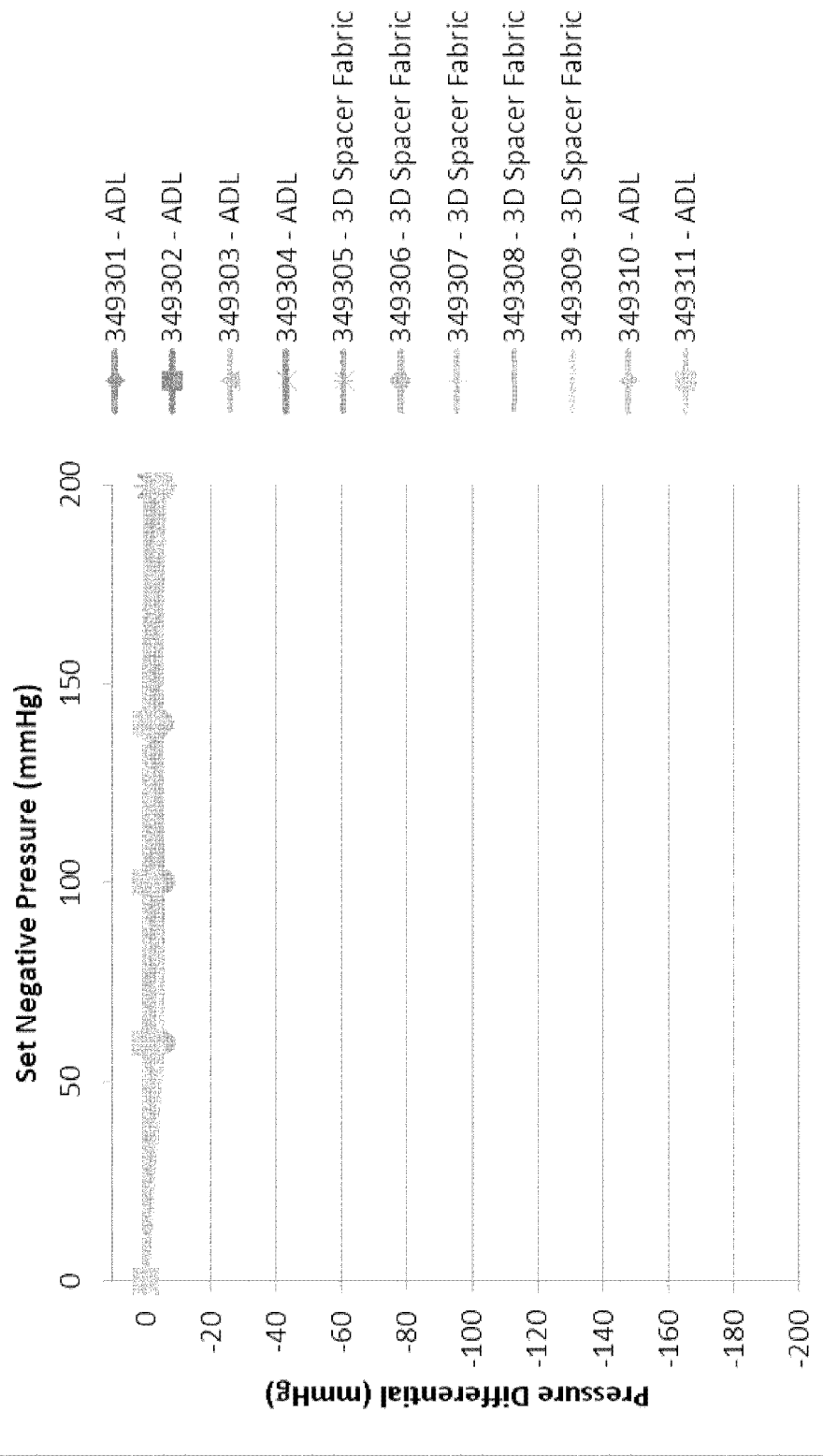

Turning to FIG. 16D, the measured pressure differential of the set of sample dressings of FIGS. 15F and 15G is depicted as a function of set negative pressure with a 16 scc/minute leak rate. This set of sample dressings includes 349301, 349302, 349303, 349304, 349305, 349306, 349307, 349308, 349309, 349310 and 349311. With respect to the ADL tested in sample 349310, the corresponding plot line demonstrates that the pressure differential exceeds −5 mmHg at least at one point across the range of negative pressure set points assessed. The plot lines of test data corresponding to all other sample dressings remain close to the zero pressure differential axis, indicating good performance of the materials or stacks tested in these samples with respect to negative pressure transmission at the specified heights and widths when wet.

Figure 16E:
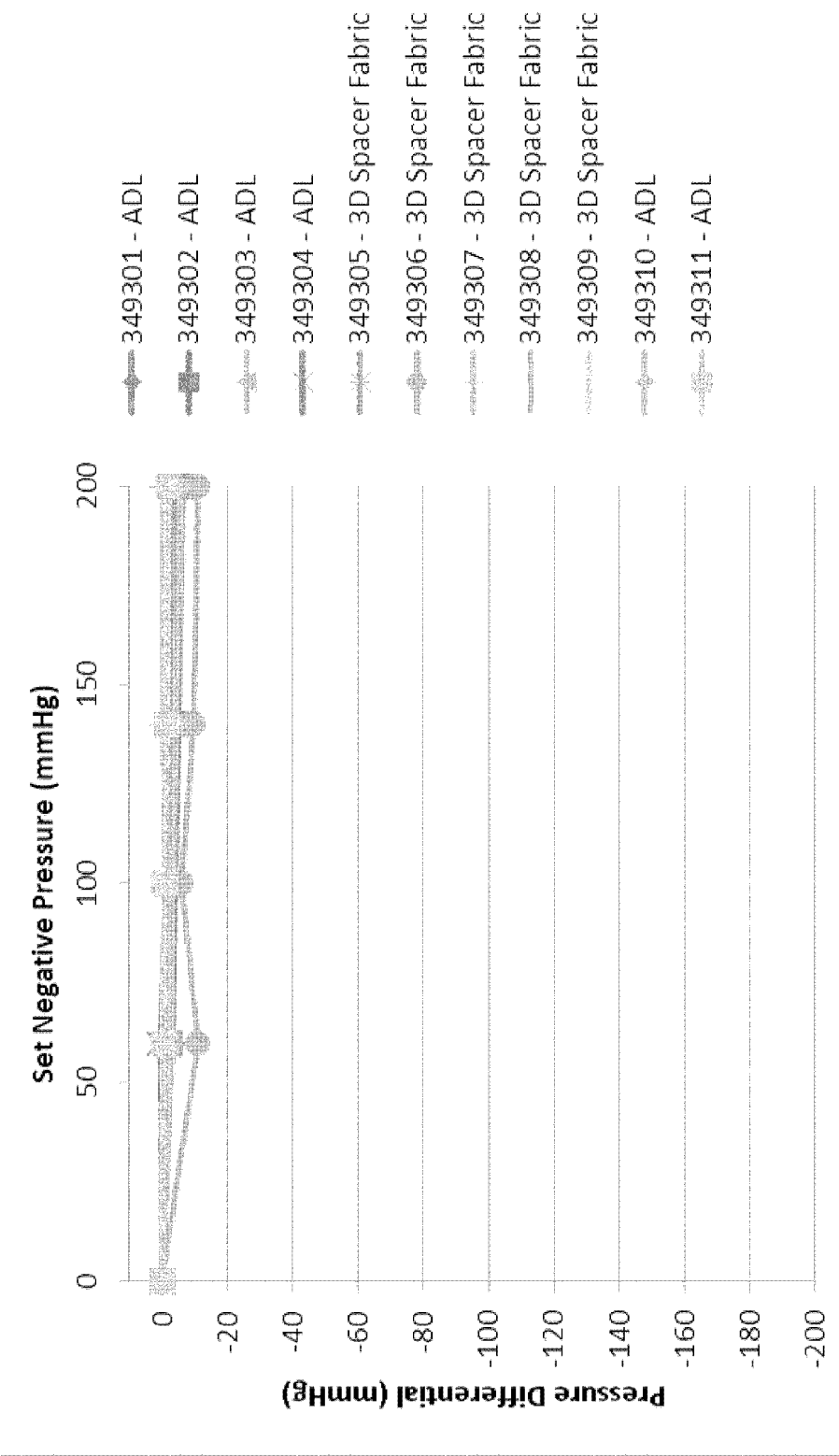

FIG. 16E illustrates test results for the same set of sample dressings depicted in FIG. 16D, however using a 50 scc/minute leak rate. With respect to the materials tested in samples 349301, 349302, 349303, 349306 and 349310, the corresponding plot lines demonstrate that the pressure differentials exceed −5 mmHg at least at one point across the range of negative pressure set points assessed. The plot lines of test data corresponding to sample dressings 349304, 349305, 349307, 349308, 349309 and 349311 all remain close to the zero pressure differential axis, indicating good performance of the materials or stacks tested in these samples with respect to negative pressure transmission at the specified heights and widths when wet.

Figure 16F:
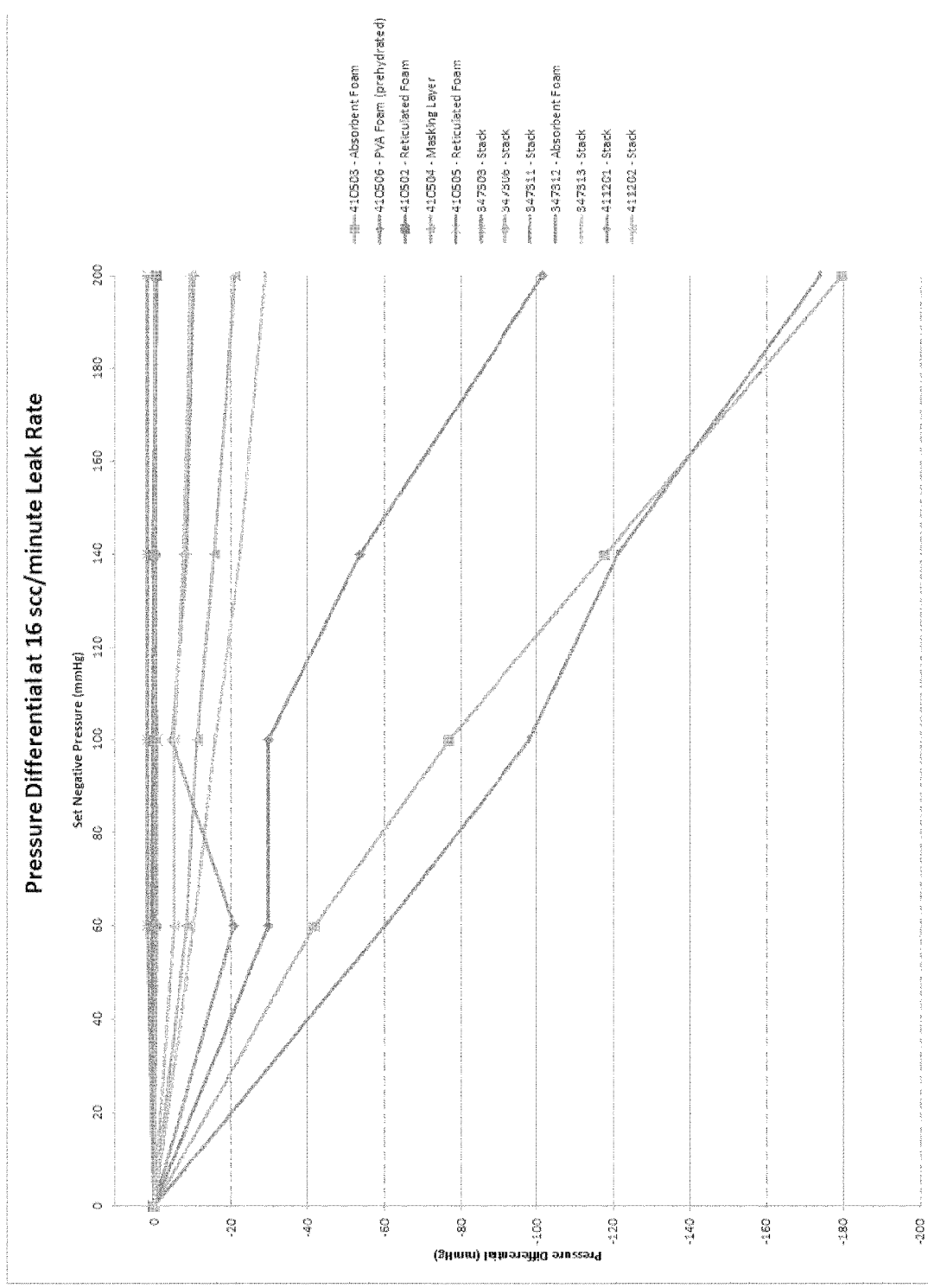

Turning to FIG. 16F, the measured pressure differential of a set of sample dressings of FIGS. 15H and 15I is depicted as a function of set negative pressure with a 16 scc/minute leak rate. This set of sample dressings includes 410502, 410503, 410504, 410505, 410506, 411201 and 411202. A subset of the sample dressings of FIGS. 15C and 15D is also depicted, including 347303, 347306, 347311, 347312, and 347313. With respect to the absorbent foam tested in sample 410503, the masking layer tested in sample 410504, the prehydrated PVA foam tested in 410506 and the stack containing a reticulated PU foam transmission layer with dimensions of 10 mm mean width and 13 mm mean height stack tested in sample 411202, the corresponding plot lines demonstrate that the pressure differential exceeds −5 mmHg at least at one point across the range of negative pressure set points assessed, in line with the observation made for this sample in the dry testing illustrated in FIGS. 15H and 15I. With respect to the stack tested in sample 347313 and the absorbent foam tested in sample 347312, the corresponding plot lines demonstrate that the pressure differential exceeds −5 mmHg at least at one point across the range of negative pressure set points assessed. As illustrated by the corresponding plot line an increase in the pressure differential was observed for sample 411201, a stack containing a reticulated PU foam transmission layer with dimensions of 10 mm mean width and 11 mm mean height, at a set-point of −60 mmHg, whilst this increased pressure differential abated at higher negative pressure set points, it still remained above −5 mmHg at other negative pressure set points, the general trend being consistent with the observation made for this sample in the dry testing illustrated in FIGS. 15H and 15I. The plot lines of test data corresponding to sample dressings 347303, 347306, 347311, 410502 and 410505 all remain close to the zero pressure differential axis, indicating good performance with respect to negative pressure transmission at the specified heights and widths for each material or stack.

Figure 16G:
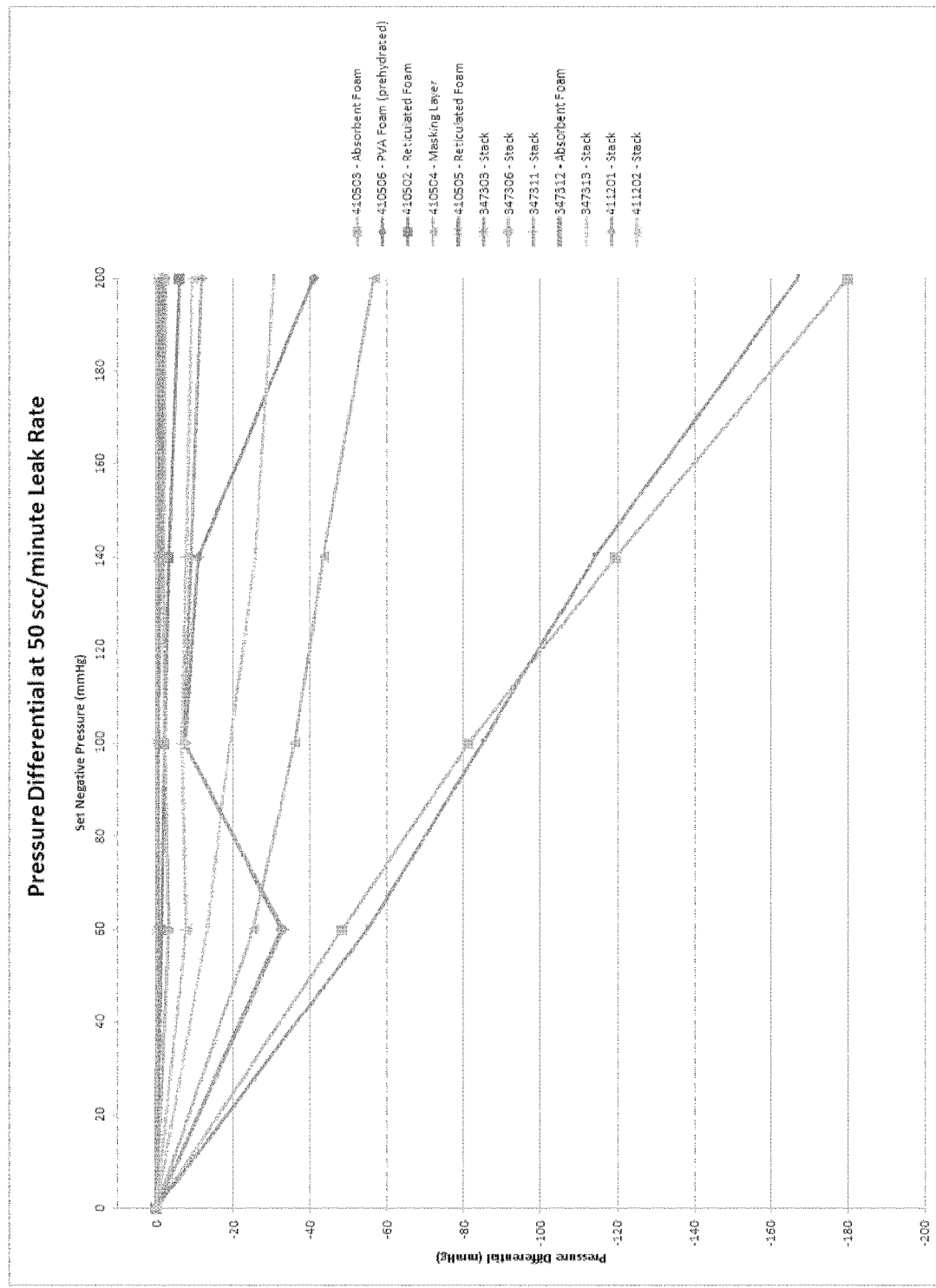

FIG. 16G illustrates test results for the same set of sample dressings depicted in FIG. 16F, however using a 50 scc/minute leak rate. The results generally correspond to the results illustrated in FIG. 16F with two exceptions. The first exception was for the reticulated PU foam layer with dimensions of 10 mm mean width and 5 mm mean height tested in sample 410502. Whilst this sample of reticulated PU foam did not display a significant increase in the measured pressure differential during wet testing with a 16 scc/minute leak rate it was observed that when the leak rate was set at 50 scc/minute and a negative pressure set point of −200 mmHg was applied the pressure differential reached −6.0 mmHg breaching the acceptability criteria set. The second exception was for the prehydrated PVA foam tested in sample 410506. As illustrated by the corresponding plot line, an increase in the pressure differential was observed for the sample up to a set point of −60 mmHg, however a decrease in the pressure differential was observed between −100 mmHg and −140 mmHg, and after −140 mmHg the increase in the pressure differential resumed. If the profiles for both leak rates are considered together, bearing in mind the sequential nature of running first with the 16 scc/minute leak rate followed by the 50 scc/minute leak rate and increasing negative pressure set point through each run, the profiles could be indicative of partial liquid clearance occurring during the test. The plot lines of test data corresponding to sample dressings 347303, 347306, 347311 and 410505 all remain close to the zero pressure differential axis, indicating good performance with respect to negative pressure transmission at the specified heights and widths for each material or stack Turning now to FIG. 16H, a comparison graph illustrates the performance of all samples, normalized to a width of 10 mm±1 mm, as a function of set negative pressure with a 16 scc/minute leak rate when wet tested. FIG. 16I illustrates test results for the same set of sample dressings depicted in FIG. 16H, however using a 50 scc/minute leak rate. Accordingly, FIGS. 16H and 16I allow for relative comparison of sample performance at a standardized width across the samples. Similar to the other pressure differential charts discussed herein, suitable transmission layer materials will demonstrate a pressure differential around or below approximately −5 mmHg at points across the range of negative pressure set points assessed.

Figure 16H:
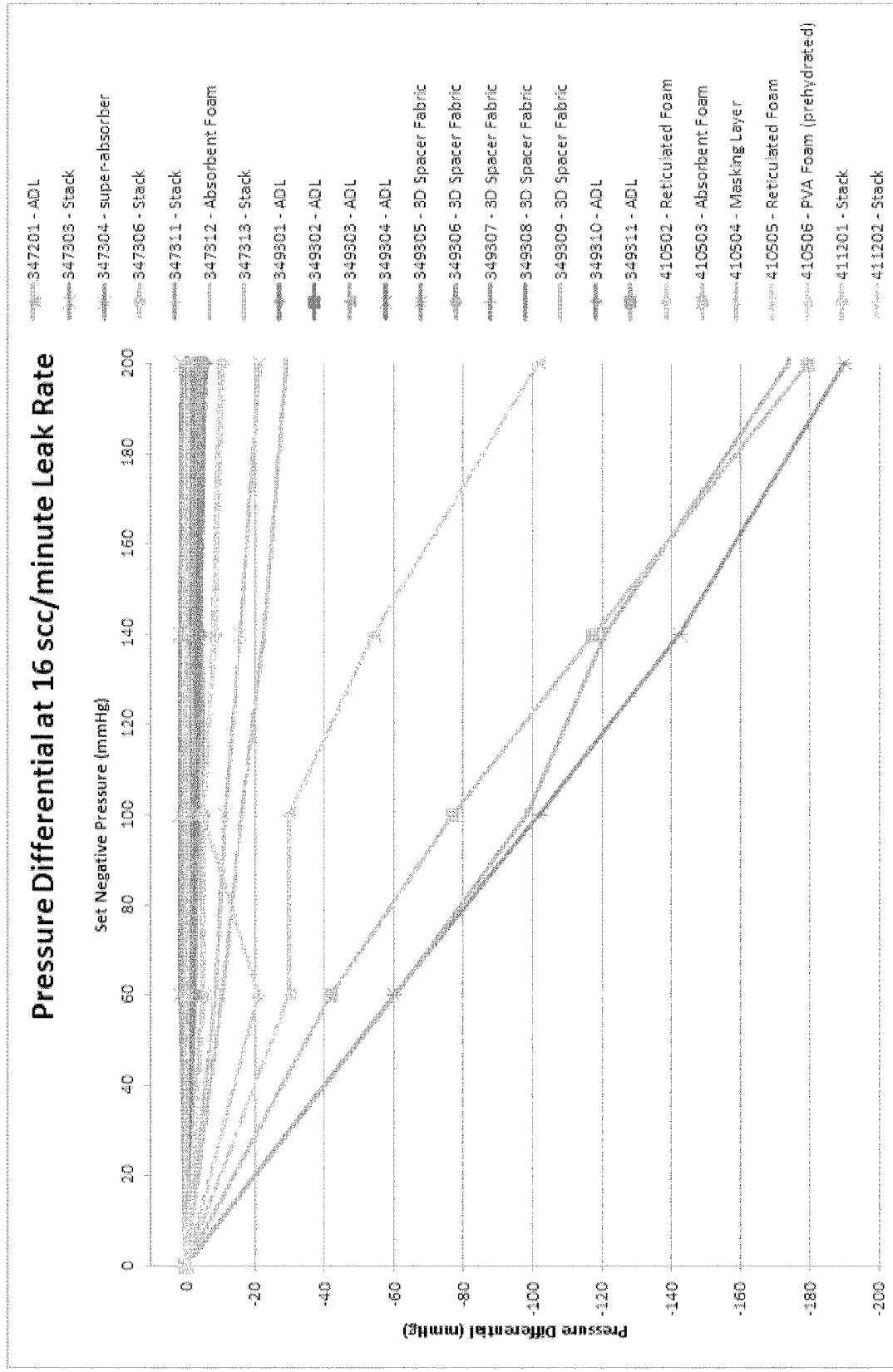
Figure 16I:
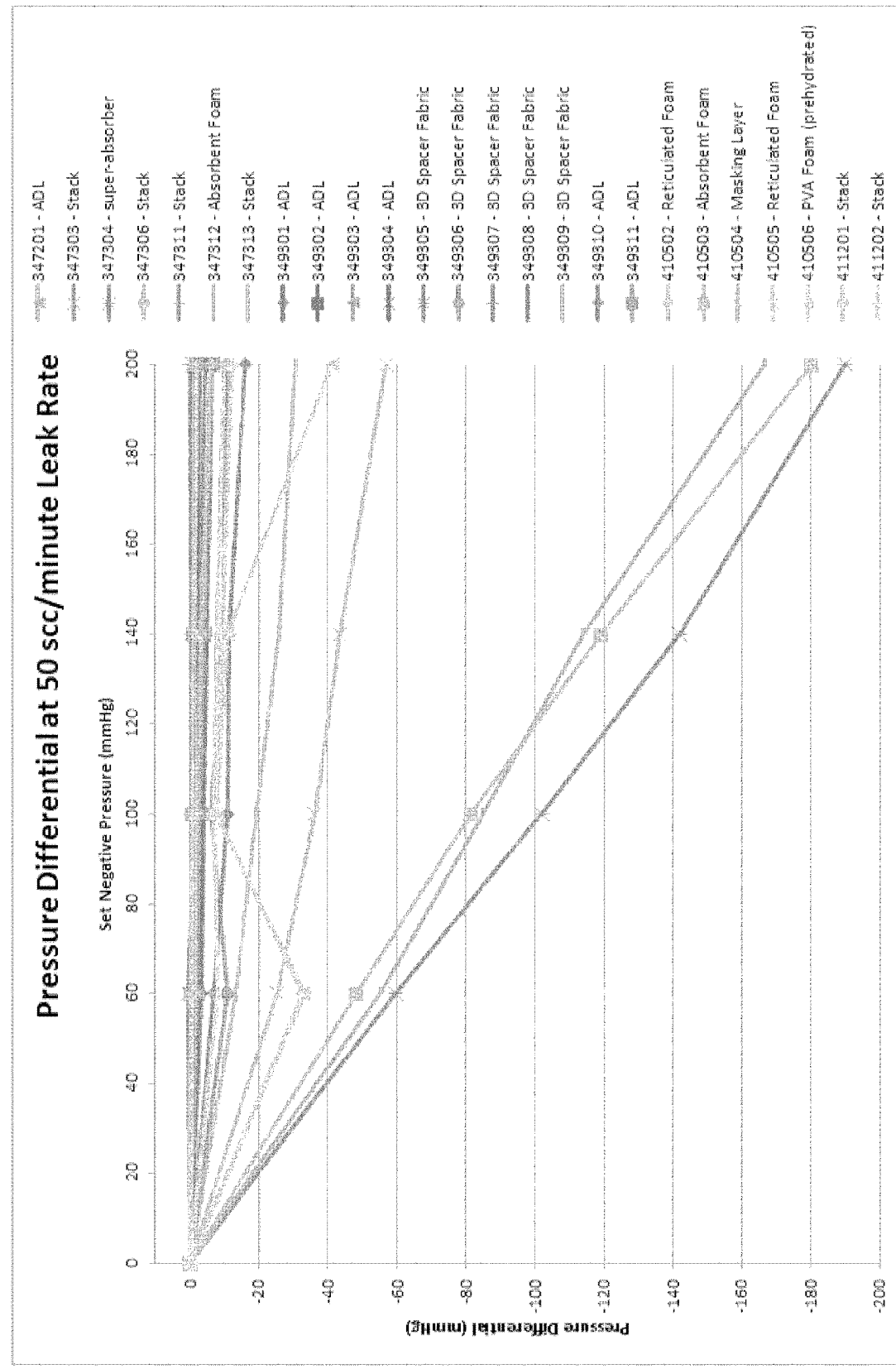
Figure 16J:
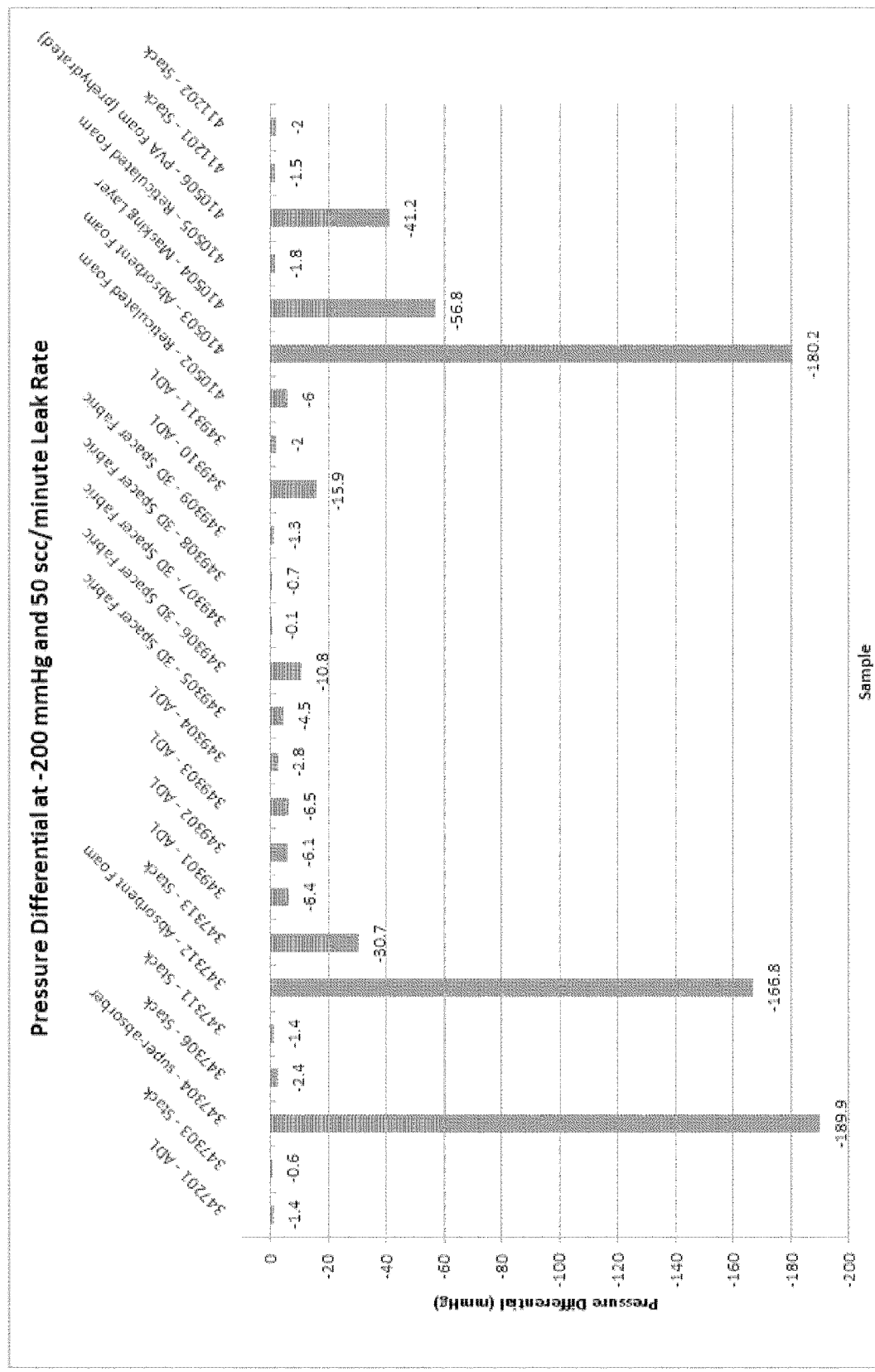

FIG. 16J illustrates the pressure differential at a negative pressure set point of −200 mmHg and 50 scc/minute leak rate after subtraction of positive control for each of the width-normalized wet tested sample dressings of FIGS. 16H and 16I. Table 3, below, provides a scoring analysis of the tested samples based on the information presented in FIG.

16J in order to provide a screen of the suitability of the various potential transmission layer materials. In all cases the samples contained a transmission layer with mean width of 10 mm±1 mm and were being assessed over a 20 mm±1 mm path length. Scoring was applied according to the following criteria:

(1) A marking of "✓" indicates that a pressure differential of −5.0 mmHg or less was recorded. Materials marked with "✓" provide the most suitable permeability to gas and liquid at the specified widths and heights when exposed to compression due to negative pressure.
(2) A marking of "✗" indicates that the criteria of (1) was not met and a pressure differential of −25.0 or less was recorded.
(3) A marking of "✗✗" indicates that the criteria of (2) was not met and a pressure differential of −160.0 mmHg or less was recorded. This can correspond to delivery of at least −40 mmHg therapy against a set point in the range −60 to −200 mmHg with an air leak of 50 scc/minute. In some scenarios, −40 mmHg can represent the minimum clinically acceptable level of wound therapy.

(4) A marking of "✗✗✗" indicates that the criteria of (3) was not met and a pressure differential of 160.1 mmHg or greater was recorded. This can correspond to delivery of less than −40 mmHg therapy against a set point in the range −60 to −200 mmHg with an air leak of 50 scc/minute. In some scenarios, delivery of less than −40 mmHg can result in clinically unacceptable levels of wound therapy.

TABLE 3

| Legend No. | Material(s) | Mean height (mm) | Mean width (mm) | Mean cross sectional area (mm2) | Assessment |
|---|---|---|---|---|---|
| 347201—ADL | Libeltex BVBA, SlimCore TL4, triple layered ADL, hydrophilic PET and bicomponent fibres, through air bonded web, 150 gsm | 2 | 11 | 27 | ✓ |
| 347303—Stack | Stack: | | | | ✓ |
| | Don & Low Ltd Non Wovens, PP non woven fabric, thermally bonded, 70 gsm | 0.4 | 15 | 6 | |
| | Baltex 7970, weft knitted polyester spacer layer fabric, 210 gsm (smaller footprint than masking layer) | 2 | 11 | 20 | |
| 347304—super-absorber | Glatfelter Falkenhagen GmbH, MH460.101, multibonded airlaid nonwoven containing super-absorbent powder, laminated against cellulose tissue, 460 gsm | 2 | 10 | 18 | ✗✗✗ |
| 347306—Stack | Stack: | | | | ✓ |
| | Don & Low Ltd Non Wovens, PP non woven fabric, blue, thermally bonded, 70 gsm | 0.4 | 14 | 6 | |
| | Glatfelter Falkenhagen GmbH, MH460.101, multibonded airlaid nonwoven containing super-absorbent powder, laminated against cellulose tissue, 460 gsm | 2 | 14 | 25 | |
| | Glatfelter Falkenhagen GmbH, MH080.121, multibonded airlaid nonwoven | 1 | 15 | 11 | |
| | Baltex 7970, weft knitted polyester spacer layer fabric, 210 gsm (smaller footprint than upper layers) | 2 | 11 | 19 | |
| 347311—Stack | Stack: | | | | ✓ |
| | Glatfelter Inc., DT360.100, thermally bonded air-laid with super-absorbent powder and cellulose fibres, 360 gsm | 3 | 14 | 46 | |
| | Baltex 7970, weft knitted polyester spacer layer fabric, 210 gsm (smaller footprint than upper layer) | 2 | 10 | 18 | |
| 347312—Absorbent Foam | Smith & Nephew, Allevyn foam, from bulk, with a non-adhesive perforated wound contact layer (WCL) laminated to the top and bottom surfaces (WCL is the same as applied to the ProGuide Wound Contact Layer (WCL) surfaces) | 10 | 10 | 99 | ✗✗✗ |
| 347313—Stack | Stack: | | | | ✗✗ |
| | Glatfelter Inc., DT360.100, thermally bonded air-laid with super-absorbent powder and cellulose fibres, 360 gsm | 4 | 11 | 40 | |
| | Smith & Nephew, RENASYS-F Foam, reticulated, open-cell, polyurethane foam | 5 | 10 | 52 | |

TABLE 3-continued

| Legend No. | Material(s) | Mean height (mm) | Mean width (mm) | Mean cross sectional area (mm2) | Assessment |
|---|---|---|---|---|---|
| 349301—ADL | Shalag Nonwovens, ST6CTPH90G, ADL, 90 gsm (longitudinal axis of the sample in line with the visually predominate fibre orientation of the distribution layer. Distribution layer orientated next to top film) | 2 | 10 | 24 | ✘ |
| 349302—ADL | Shalag Nonwovens, STAHTCT8OL, ADL, 80 gsm (Distribution layer orientated next to top film) | 1 | 11 | 16 | ✘ |
| 349303—ADL | Shalag Nonwovens, ST6CT8H65, ADL, 65 gsm (Distribution layer orientated next to top film) | 3 | 9 | 26 | ✘ |
| 349304—ADL | Shalag Nonwovens, ST6NT8H75, ADL, 75 gsm (Distribution layer orientated next to top film) | 4 | 10 | 44 | ✓ |
| 349305—3D Spacer Fabric | Apex Mills, 3D Spacer Fabric, DNB198A, polyester, 270 gsm (Face with larger holes orientated next to top film.) | 2 | 10 | 21 | ✓ |
| 349306—3D Spacer Fabric | Apex Mills, 3D Spacer Fabric, DNB197, polyester, 670 gsm | 6 | 10 | 60 | ✘ |
| 349307—3D Spacer Fabric | Heathcote Fabrics Limited, SpaceTec, 2.5 mm gauge, polyester, 430 gsm (Face with larger holes orientated next to top film.) | 3 | 10 | 25 | ✓ |
| 349308—3D Spacer Fabric | Heathcote Fabrics Limited, SpaceTec, 3 mm gauge, polyester, 320 gsm (Face with larger holes orientated next to top film.) | 3 | 10 | 30 | ✓ |
| 349309—3D Spacer Fabric | Apex Mills, 3D Spacer Fabric, DNB22(6), polyester (Face with larger holes orientated next to top film.) | 3 | 9 | 29 | ✓ |
| 349310—ADL | Libeltex BVBA, DryWeb T28F, monolayered AQL, hydrophilic PET and bicomponent fibres, through air bonded web, 50 gsm | 1 | 10 | 14 | ✘ |
| 349311—ADL | Libeltex BVBA SlimCore TL4, triple layered ADL, hydrophilic PET and bicomponent fibres, through air bonded web, 90 gsm | 3 | 10 | 29 | ✓ |
| 410502—Reticulated Foam | Smith & Nephew, RENASYS-F Foam, reticulated, open-cell, polyurethane foam | 5 | 10 | 53 | ✘ |
| 410503—Absorbent Foam | Smith & Nephew, Allevyn foam, from bulk | 6 | 10 | 61 | ✘✘✘ |
| 410504—Masking Layer | Don & Low Ltd Non Wovens, PP non woven fabric, blue, thermally bonded, 70 gsm | 0 | 10 | 5 | ✘✘ |
| 410505—Reticulated Foam | Smith & Nephew, RENASYS-F Foam, reticulated, open-cell, polyurethane foam | 10 | 10 | 100 | ✓ |
| 410506—PVA Foam (prehydrated) | KCI, WhiteFoam, prehydrated open cell PVA foam | 10 | 10 | 96 | ✘✘ |
| 411201—Stack | Glatfelter Inc., DT360.100, thermally bonded air-laid with super-absorbent powder and cellulose fibres, 360 gsm | 4 | 14 | 57 | ✓ |
| | Smith & Nephew, RENASYS-F Foam, reticulated, open-cell, polyurethane foam (smaller footprint than upper layer) | 11 | 10 | 106 | |

TABLE 3-continued

| Legend No. | Material(s) | Mean height (mm) | Mean width (mm) | Mean cross sectional area (mm2) | Assessment |
|---|---|---|---|---|---|
| 411202—Stack | Glatfelter Inc., DT360.100, thermally bonded air-laid with super-absorbent powder and cellulose fibres, 360 gsm | 4 | 15 | 57 | ✓ |
| | Smith & Nephew, RENASYS-F Foam, reticulated, open-cell, polyurethane foam (smaller footprint than upper layer) | 13 | 10 | 131 | |

Table 4 illustrates the raw data used to generate the charts of FIGS. 16A-16J.

TABLE 4

| | Leak rate (scc/min) 16 Pressures (mmHg) | | | | | Leak rate (scc/min) 50 Pressures (mmHg) | | | | |
|---|---|---|---|---|---|---|---|---|---|---|
| Ref | 0 | 60 | 100 | 140 | 200 | 0 | 60 | 100 | 140 | 200 |
| | Recorded dP (mmHg) | | | | | | | | | |
| Day 3: | | | | | | | | | | |
| Negative Control | 0 | −66.8 | −108.6 | −150.8 | >−200 | | | | | |
| Positive Control | 0.1 | −3.3 | −5.2 | −7 | −9.9 | 0.2 | −3.4 | −5.3 | −7.1 | −10 |
| 346604 | 0.1 | −51.5 | −80.2 | −105.1 | −137.1 | 0.1 | −47.2 | −88.4 | −118.5 | −164.9 |
| 346605 | −0.2 | −5.7 | −8.3 | −13.1 | −19.1 | 0 | −7.2 | −12.2 | −18.6 | −30.4 |
| 346606 | 0.1 | −3.6 | −5.8 | −10.3 | −15 | −0.1 | −4.4 | −7.1 | −10.3 | −19.2 |
| 347304 | 0.1 | −63.3 | 107.4 | 149.2 | >−200 | | | | | |
| 347201 | −0.1 | −4 | −6 | −7.8 | −10.7 | 0.1 | −4 | −6.1 | −8.2 | −11.5 |
| Day 5 | | | | | | | | | | |
| Negative Control | 0.1 | −62.8 | −104.2 | −144.1 | >−200 | | | | | |
| Positive Control | 0.1 | 0.4 | 0.7 | 1 | 1.5 | 0 | 0.2 | 0.5 | 0.8 | 1.3 |
| 349301 | 0.02 | −1.9 | −2.1 | −2.3 | −3.1 | −0.2 | −3.1 | −3.7 | −4.1 | −5.3 |
| 349302 | 0.1 | −0.9 | −1.1 | −1.5 | −2.4 | 0 | −2.2 | −2.7 | −3.3 | −4.8 |
| 349303 | 0 | −0.8 | −0.8 | −1.2 | −2.1 | 0.1 | −1.6 | −2.2 | −3 | −5.1 |
| 349304 | −0.1 | −0.7 | −0.6 | −0.5 | −0.2 | 0 | 0.9 | −0.7 | −1.2 | −1.5 |
| 349305 | −0.1 | 0.1 | −0.1 | −0.4 | −1.2 | 0 | −0.8 | −1.4 | −1.8 | −3.2 |
| 349306 | 0.1 | −4.5 | −4.3 | −3.5 | −3 | 0 | −10.5 | −5.3 | −8.5 | −9.5 |
| 349307 | 0 | −0.8 | −0.2 | −0.3 | 0.9 | 0.1 | −0.7 | −0.2 | 0.7 | 1.3 |
| 349308 | 0.1 | 0.4 | 0.8 | 1.2 | 1.2 | 0 | −0.5 | −0.1 | 0.2 | 0.6 |
| 349309 | −0.2 | −4.7 | −3.4 | 0.9 | −3.7 | 0 | −0.2 | −0.1 | 0 | 0 |
| 349310 | 0.2 | −2 | −2.2 | −3 | −3.8 | 0.1 | −6.4 | −10.2 | −10.4 | −14.5 |
| 349311 | 0 | 0.6 | 0.9 | 1.1 | −3.2 | −0.2 | −0.3 | −0.4 | −0.6 | −0.9 |
| Day 6: | | | | | | | | | | |
| Negative Control | 0.1 | −62.7 | −103.7 | −143.8 | >−200 | | | | | |
| Positive Control | 0.1 | 0.1 | 0.1 | 0.1 | −0.1 | 0.3 | 0.6 | 0.5 | 0.5 | 0.3 |
| 410503 | 1.9 | −40 | −75 | −116 | −178 | 2.2 | −46 | −79 | −117 | −178 |
| 410506 | −0.2 | −30 | −30 | −54 | −102 | 1.2 | −31 | −6 | −9.5 | −40 |
| Day 7: | | | | | | | | | | |
| Negative Control | 1.4 | −60.6 | −101.4 | −141.2 | >−200 | | | | | |
| Positive Control | 1.3 | 0.5 | 0.3 | 0.2 | 0 | 0.5 | 0.3 | 0.2 | 0.1 | −0.1 |
| 410502 | 2 | 1.7 | 1.4 | 0.9 | −0.2 | 2.2 | 0.7 | −0.2 | −1.4 | −4.4 |
| 410504 | 2.3 | −7 | −10 | −14.5 | −20.2 | 2.4 | −23 | −34 | −41.6 | −55 |
| 410505 | 1.8 | 0.8 | −0.1 | 1 | −0.2 | 2.3 | 1.7 | 1.4 | 0.9 | −0.1 |
| 347303 | 0.9 | 1.7 | 1.6 | 1.4 | 1.1 | 2 | 1.2 | 1.3 | 1.1 | 0.8 |
| 347306 | 2 | 0.4 | 0.5 | 0.3 | 0.1 | 2.1 | −1.4 | −0.3 | −0.3 | −0.9 |
| 347311 | 2.5 | 1.3 | 1.2 | 1 | 0.6 | 2.2 | 1.6 | 1.4 | 1.1 | 0.2 |
| 347312 | 2.2 | −59 | −97 | −120 | −173 | 2.4 | −53 | −83 | −112 | −165 |
| 347313 | 2.3 | −9 | −14.7 | −21.4 | −28 | 2.3 | −11 | −17.1 | −24 | −29 |
| 411201 | 1.7 | −20 | −4 | −7.8 | −10 | 1.5 | −32 | −6 | −8 | −11 |
| 411202 | 1.8 | −4.3 | −4.5 | −7 | −9 | 2 | −6 | −5 | −6 | −8 |

As indicated by the test results illustrated in FIGS. 16A-16J and the material specifications of Table 1, a dressing implementing the reticulated foam or SlimCore TL4 as a transmission layer will experience low negative pressure differentials across bridging portions with widths as low as approximately 3 mm for the reticulated foam and 11 mm for the SlimCore TL4, even when fluid is introduced to the dressing system. Although spacer material such as Baltex 3D weft-knit fabric was not wet tested, this material is expected to produce clinically appropriate test results of a pressure differential in the range of −5 mmHg to 0 mmHg at a −200 mmHg pressure set point using the described test model or a similar test model. Accordingly, open-cell reticulated foam, SlimCore TL4, spacer material, and similar woven and non-woven materials are suitable transmission layers for bridging portions of dressings. Such materials are suitable in some embodiments for the bridging portions described above or below. Although additional layers can be used in bridging portions in some embodiments, for example a masking layer or combinations of transmission layers, bridging portions will transmit clinically appropriate negative pressure ranges using just one transmission layer satisfying the testing criteria.

The test results of FIGS. 15A-16J highlight the interplay between material properties, cross sectional dimensions (minimum width and height) and the effect of adjacent materials within the dressing on the clinically or therapeutically suitable permeability of a sample to gas and liquid while under compression due to negative pressure. For example, the reticulated foam alone typically can be a suitable material for use as a transmission layer, however when combined with an absorbent layer over the reticulated foam, at heights below approximately 10 mm the foam began to fail to deliver therapeutically suitable negative pressure.

VIII. Overview of Additional Bridged Dressing Embodiments

Figure 17A:
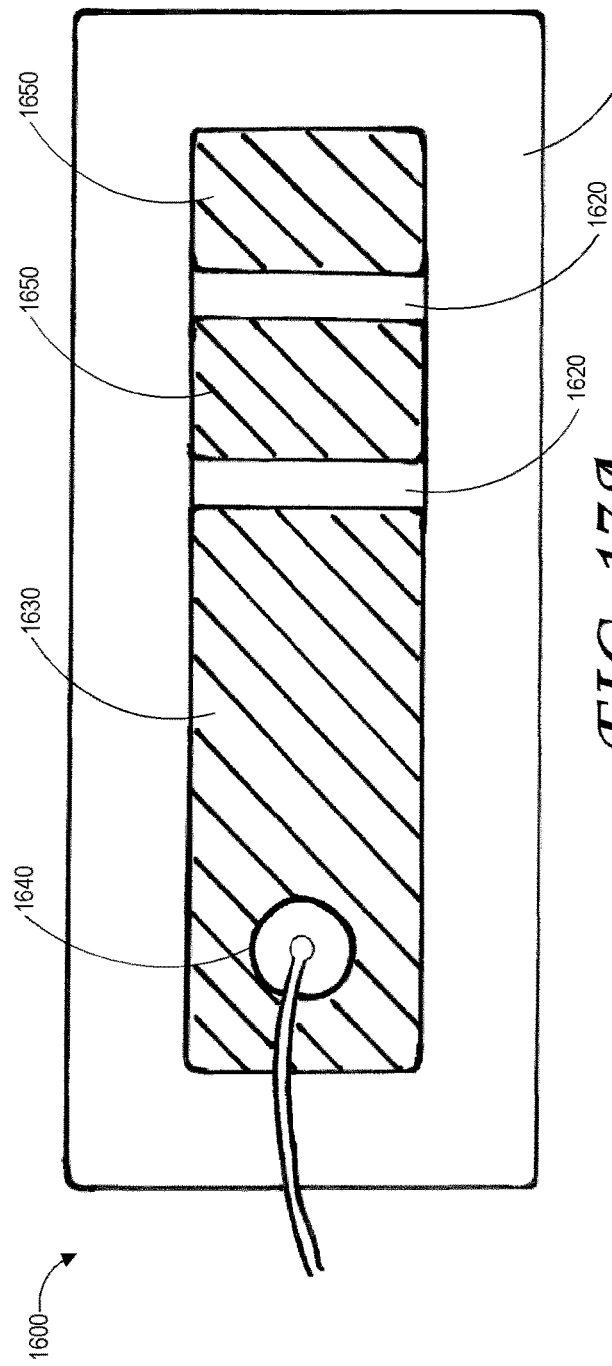
FIGS. 17A-17B illustrate one embodiment of a trimmable dressing having a reduced height bridging portion.
Figure 17B:
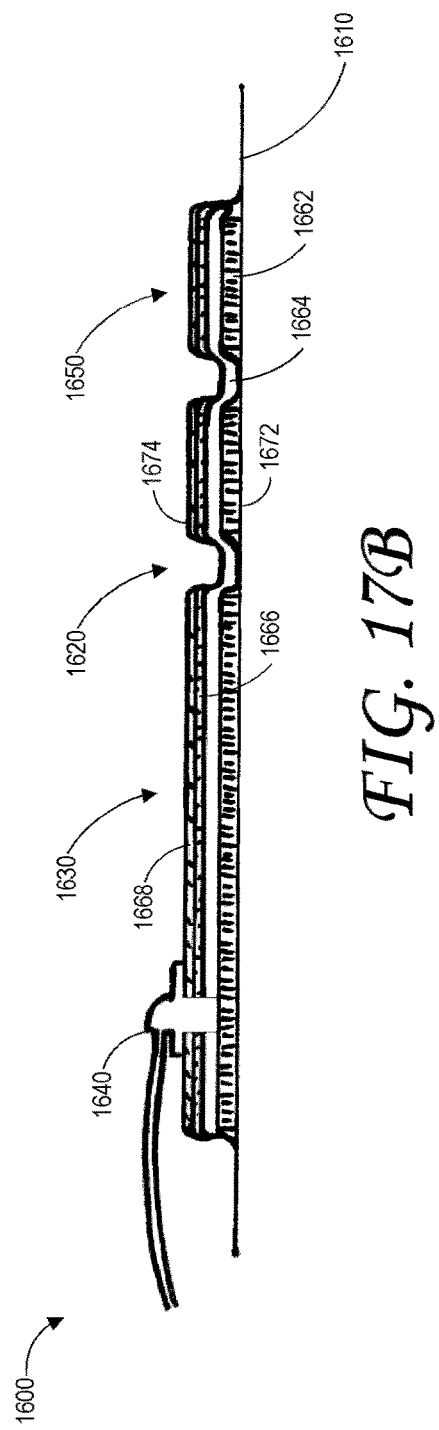

FIG. 17A illustrates a plan view of a trimmable dressing 1600 embodiment wherein the number of layers present in the bridging portions 1620 of the dressing is less than in an absorbent pad portion 1630 or a secondary absorbent portion 1650 of the dressing. FIG. 17B illustrates a side view of the dressing 1600. Accordingly, the overall height of the dressing is reduced at the bridging portions 1620 relative to the absorbent pad portions. In some embodiments, the dressing can also reduce in width at the bridging portions relative to the absorbent pad portions. The dressing 1600 also includes a port 1640 for delivery of negative pressure.

The dressing 1600 includes a spacer layer 1662 in the absorbent pad portion 1630 and secondary absorbent portions 1650. An ADL 1664 extends across the length of the dressing through the absorbent pad portion 1630, secondary absorbent portions 1650, and bridging portions 1620. The ADL 1664 satisfies the testing criteria specified above and is capable of negative pressure transmission through the bridging portions 1620. In some implementations of the trimmable dressing 1600, the ADL 1664 may be constructed from an ADL material that is easier to cut than a spacer material, and may be accordingly selected for the bridging portions 1620. In other embodiments, the spacer layer 1662 may extend across the length of the dressing in addition to or instead of the ADL 1664.

In the absorbent pad portion 1630 and secondary absorbent portions 1650, the dressing 1600 includes an absorbent layer 1666 and masking layer 1668. In some embodiments, the masking layer 1668 may extend across the bridging portions 1620, and may include holes, windows, perforations, or other visual indicators for indicating to a user where to cut the dressing. For example, perforations may be arranged in a dashed or dotted line configuration along a location within a bridging portion 1620, revealing a contrasting color of the ADL 1664 beneath the masking layer 1668 to visually indicate a potential location for trimming the dressing 1600. This approach could be extended to include designs and symbology such as the symbol of a pair of scissors and/or a dotted line, or notches/chevron on each side of the masking layer, lettering indicating a "cut here" location, or the like. The interior layers 1662, 1664, 1666, 1668 are positioned between a wound contact layer 1672 and a top film layer 1674 that are sealed together around a perimeter 1610, for example a perimeter of approximately 2.5 cm in some embodiments.

This layer arrangement can provide the advantage of increased flexibility at the bridging points during wear of the dressing, easy cutting with scissors (or other means) during fitting and shaping of the dressing to a wound site, and easier sealing of cut portions. The reduced height of the bridging portions provides a smaller gap that needs to be sealed. Cut or trimmed portions can be sealed with a sealant, a sealing strip as depicted in FIGS. 14A-14D, a flexible adhesive drape, or other sealing means. In addition, use of different top layers in the absorbent pad portions compared to the bridging portions can result in a color coded dressing, making the cutting locations clear to the user. Such a dressing can be convenient for use along long incision wounds where the length varies from patient to patient, for example incisions resulting from abdominoplasty procedures, as the dressing can be trimmed according to specific patient needs.

FIG. 18 illustrates one embodiment of a dressing 1700 suitable for placement on a heel. The dressing 1700 includes a sealed perimeter 1710, bridging portion 1720, central absorbent pad 1730, and a port 1740 for transmission of negative pressure to the dressing 1700, and optionally includes two secondary absorbent pads 1750. The center portion 1740 can be applied to a patient's heel such that the top half is on the back of the heel and the bottom half folds under the heel. The "wings" including the optional secondary absorbent pads 1750 and the surrounding bridging and perimeter portions can then be folded around each side of the patient's ankle. Cushioning is important with heel dressings to protect the malleolus for typical users (i.e. diabetic heel ulcer patients). Optionally, additional secondary absorbent pad portions 1750 can be positioned in dressing 1700 in order to be located over each malleolus when applied in order to provide cushioning and increase the overall absorbency of the dressing. The spacer could optionally be included in the secondary absorbent pad portions 1750 for additional cushioning. In some embodiments, the secondary absorbent pad portions 1750 can include a spacer layer and an ADL without an absorbent layer.

The central absorbent pad 1730 and optional secondary absorbent pads 1750 can include an absorbent layer as discussed herein, and can also include a layered configuration as disclosed herein, for example with reference to FIGS. 4A-4D. The bridging portions 1720 can include any material having negative pressure transmission properties that satisfy the testing criteria described above with respect to FIGS. 15A-16C, for example a 3D-knit spacer layer, woven ADL (such as Libeltex Slimcore TL4), or open-cell reticulated foam.

Fitting a composite NPWT dressing to a heel has been a significant challenge due to conformability to this highly curved area, especially given the good seal required to exclude leaks from the system. Folding a thicker, composite dressing around a highly nonplanar surface such as a heel often results in leaks in the dressing system. The flexible bridge portions 1720 surrounding the main pad portion 1730 and optional secondary pad portions 1750 as illustrated in FIG. 18 can unlock this needed conformability and allow negative pressure therapy to be successfully applied using a composite heel dressing.

FIG. 19 illustrates an embodiment of an extremity dressing 1800. The extremity dressing 1800 can have a multi-layered absorbent pad 1830 in a center area, here depicted as a circular shape (though others are possible in other embodiments), and three bridge portions 1820 extending away from the center absorbent pad. The bridge portions 1820 are surrounded by a sealed perimeter 1810, for example of a wound contact layer and a top film layer. A port 1840 can be attached to provide negative pressure to the dressing 1800. The bridge portions 1820 can include Libeltex SlimCore ADL in some embodiments. Any of the materials described above with respect to FIGS. 4A-4D and FIGS. 9A-13 can be suitable for use in dressing 1800. Materials used in bridge portions 1820 may be selected to satisfy the testing criteria described above with respect to FIGS. 15A-16C.

In other embodiments, two, four, or more bridge portions 1820 can extend away from the center pad. The bridge portions 1820 may be evenly spaced around a circumference of the dressing, as illustrated, or can be located asymmetrically as needed for providing a dressing for specific wound types. One or more bridge portions 1820 can be trimmed or cut off according to the wound shape. Cut or trimmed portions can be sealed with a sealant, a sealing strip as depicted in FIGS. 14A-14D, a flexible adhesive drape, or other sealing means.

The bridge portions 1820 can deliver negative pressure to the center absorbent pad 1830 of the dressing, which may need to be weight bearing. Accordingly, port 1840 can be located on one or more of the bridge portions 1820, in some embodiments. A spacer layer in the center absorbent pad can provide additional cushioning for the user and also serve to maintain an air path even if that section of the dressing is weight bearing.

Such a dressing configuration can provide for therapeutic advantages compared to previous dressings in certain circumstances involving large wounds on a patient's extremity, for example following amputation by placement at the distal end of the residual limb. The radially extending arms can extend over incision wounds, and in some embodiments can include additional absorbent material over some or all of the radially extending arm. Wounds on nonplanar body areas with tight geometries can also benefit from treatment with the dressing of FIG. 19.

FIG. 19 illustrates a wound dressing having a center absorbent pad surrounded by a skirt portion. The skirt portion includes at least one transmission layer, and can include other layers in some embodiments, such as an obscuring layer. The center absorbent pad can include the transmission layer as well as an absorbent layer. The skirt portion surrounding the pad portion can allow for delivery of negative pressure over a wide area with liquid stored locally in the center of the dressing. In addition, the skirt portion allows for dynamic shaping of the dressing to conform to a patient's wound while providing a relatively small edge gap for sealing at the cut portions. Cut or trimmed portions can be sealed with a sealant, a sealing strip as depicted in FIGS. 14A-14D, a flexible adhesive drape, or other sealing means.

Figure 20B:
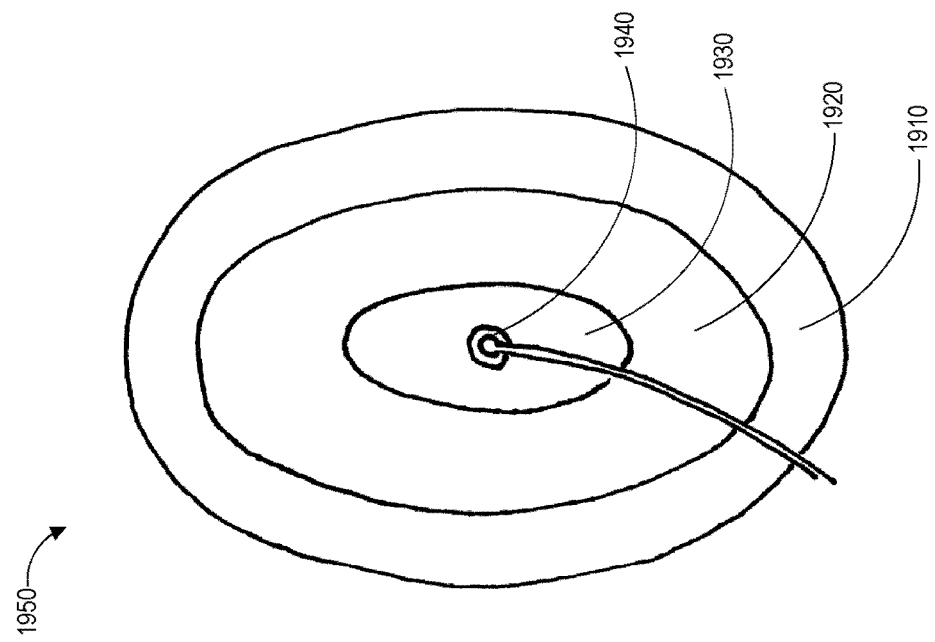
FIGS. 20A and 20B illustrate two embodiments of a trimmable dressing having a skirt portion.
Figure 20A:
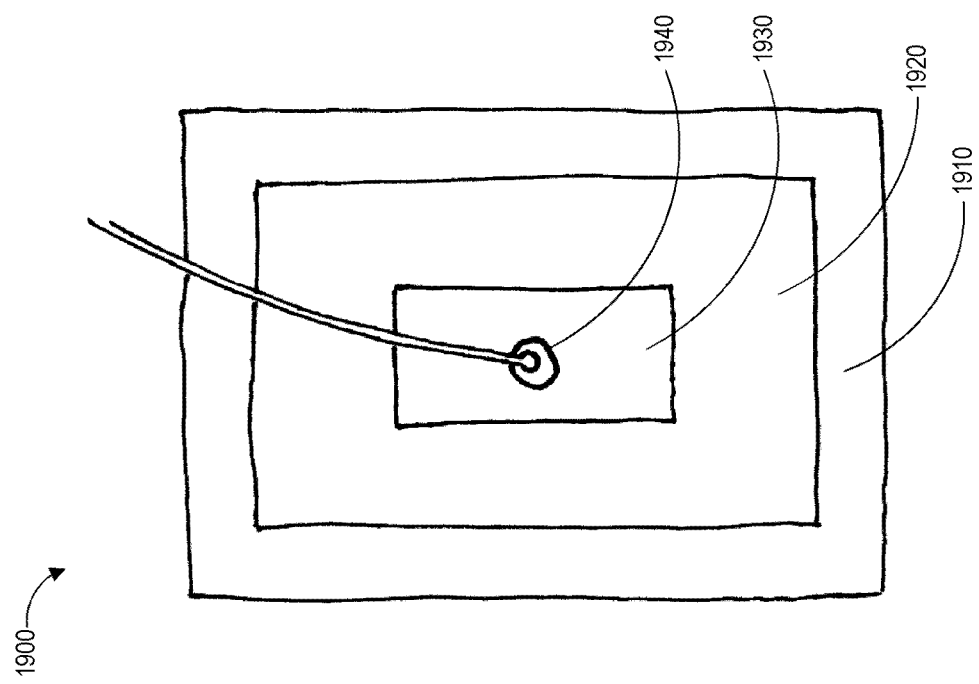

FIGS. 20A and 20B illustrate two embodiments of dressings 1900, 1950 having a sealed perimeter 1910 surrounding a bridge or skirt portion 1920, the skirt portion 1920 surrounding an absorbent pad portion 1930 having a port 1940. The port 1940 can be repositioned in any area over the skirt portion 1920 or absorbent pad portion 1930 in other embodiments. The skirt portion 1920 can function like a bridge portion illustrated in many of the dressings described above, that is to transmit fluid and negative pressure across the dressing 1900, 1950. In some embodiments, multiple absorbent pad portions can be connected by a skirt portion. The absorbent pad portion 1930 can include an absorbent layer as discussed herein, and can also include a layered configuration as disclosed herein, for example with reference to FIGS. 4A-4D. Any of the materials described above with respect to FIGS. 4A-4D and FIGS. 9A-13 can be suitable for use in dressing 1900.

The skirt portion 1920 may be constructed so as to minimize a height of the dressing 1900, 1950 at the skirt portion 1920, and therefore a distance to be sealed when the skirt portion 1920 is trimmed. For example, the skirt portion can include just one layer in some embodiments, the skirt portion layer selected based on negative pressure transmission properties. The skirt portion 1920 can include any material having negative pressure transmission properties that satisfy the testing criteria described above with respect to FIGS. 15A-16C, for example a 3D-knit spacer layer, woven ADL (such as Libeltex Slimcore TL4), or open-cell reticulated foam.

Advantageously, the large skirt portion 1920 surrounding the absorbent pad portion 1930 allows the dressing 1900. 1950 to be trimmed to conform to the shape of a wound, even for irregularly shaped wounds, without losing the ability to transmit negative pressure across the dressing. Cut or trimmed portions can be sealed with a sealant, a sealing strip as depicted in FIGS. 14A-14D, a flexible adhesive drape, or other sealing means.

Another dressing embodiment, not illustrated, can include a plurality of cell or main portions connected by a plurality of bridging portions. The bridging portions can have a smaller width, height, or both relative to surrounding cell portions. In some embodiments, a minimum bridge width can be 1 mm (or approximately 1 mm). The dressing can include an optional wound contact layer and a cover layer sealed together around a perimeter. Between the wound contact layer and the cover layer, open-cell foam, for example a reticulated foam, can extend through the cell portions and bridge portions. The foam can be continuous or assembled from discrete portions sized to fit within the cell and bridge portions. Certain embodiments of the dressing may or may not include an absorbent material, and may include a canister or other collection vessel external to the dressing for collecting wound exudate removed from the wound.

Figure 21:
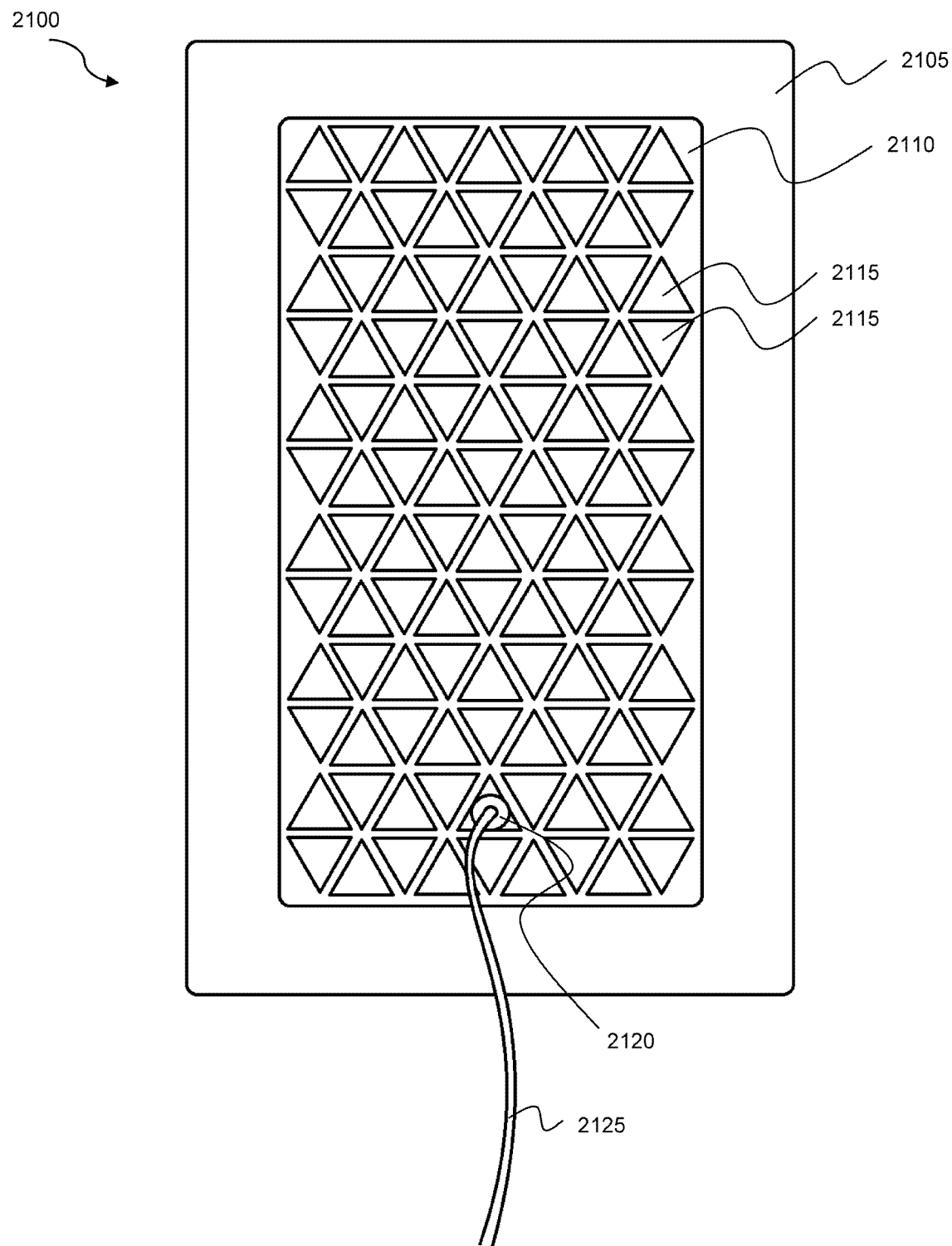
FIG. 21 illustrates an embodiment of a trimmable wound dressing comprising a plurality of portions or cells.

Referring now to FIG. 21, another embodiment of a trimmable dressing 2100 is illustrated. The dressing may comprise, from bottom to top, an optional wound contact layer (not shown), a transmission layer and/or ADL over the wound contact layer, a plurality of absorbent cells over the transmission layer and/or, and a cover layer over the plurality of absorbent cells. As illustrated in FIG. 21, one embodiment of the dressing includes a border 2105, a generally rectangular transmission layer 2110, a number of absorbent cells 2115, a port 2120, and a conduit 2125 for connection of the dressing 2100 to a source of negative pressure. The border 2105 can include a cover layer as described above sealed to the healthy skin of a patient surrounding a wound in one example, or can include a cover layer sealed to a wound contact layer as described above.

This cover layer may extend over the plurality of absorbent cells 2115. The port 2120 and conduit 2125 can be configured for transmitting negative pressure to the dressing 2100 from a source of negative pressure when in use.

The transmission layer 2110 can extend across the entire central pad area, and can be any material described herein, or the equivalent, having suitable permeability to gas and liquid at a minimum height and/or width. By having the transmission layer 2110 extend across the central pad area rather than only being placed in bridging areas, a more comfortable distribution of pressure over the patient's therapy site can be achieved. Such pressure distribution can be considered both from the point of view of NPWT delivery and from the point of view of protecting friable skin, where (depending on the design of the dressing) blistering can be caused at pad edges. Therefore, a continuous transmission layer can, in some embodiments, minimize the number of pad edges (i.e. using a continuous lower layer) providing an advantage for pressure distribution.

A number of absorbent cells 2115 can be included above the transmission layer 2110, and can be any of the absorbent materials described herein, for example with respect to FIGS. 3A-4D and 11A-11B. By cutting the dressing 2100 along the areas of transmission layer 2110 between adjacent cells 2115, the dressing 2100 can be adaptively sized to correspond to the shape of a patient's wound. The dressing 2100 can be sealed along cut portions by one or more of re-sealing of the cover layer and wound contact layer, through a sealant adhesive, and sealing strips as described in FIGS. 14A-14D in various embodiments.

Although the absorbent cells 2115 are illustrated as being triangular in shape, other variations can include circular, oval, square, rectangular, hexagonal, or other shaped cells. Further, although the absorbent cells 2115 are illustrated as being discrete portions of absorbent material, in other embodiments the absorbent cells 2115 can be connected by bridging portions.

IX. Overview of Additional Layer Materials

FIGS. 22A through 22E illustrate an example of Libeltex DryWeb T28F that can be suitable for use as acquisition distribution layer material (ADL) material which may be used in any of the dressing embodiments described above, and which may also be used in any of the port or fluidic connector embodiments described above. To those versed in the art of acquisition distribution layers, also known as "surge layers," it would be obvious that other ADL materials may be used to achieve a similar effect of laterally wicking fluid. Suitable ADL materials can allow for full capacity use. Such ADL layers may be composed of multiple fiber types and be complex in structure and design.

Figure 22A:
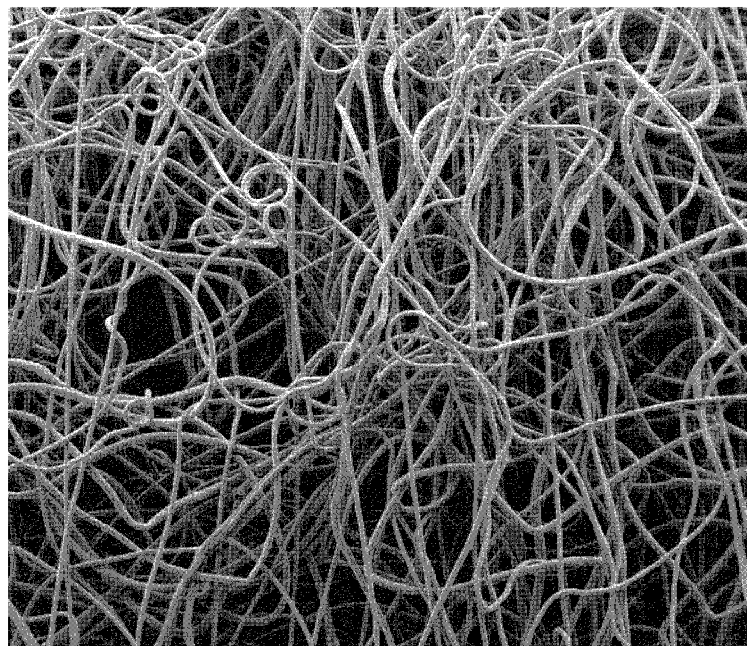
FIGS. 22A through 22E illustrate another embodiment of acquisition distribution layer material.
Figure 22B:
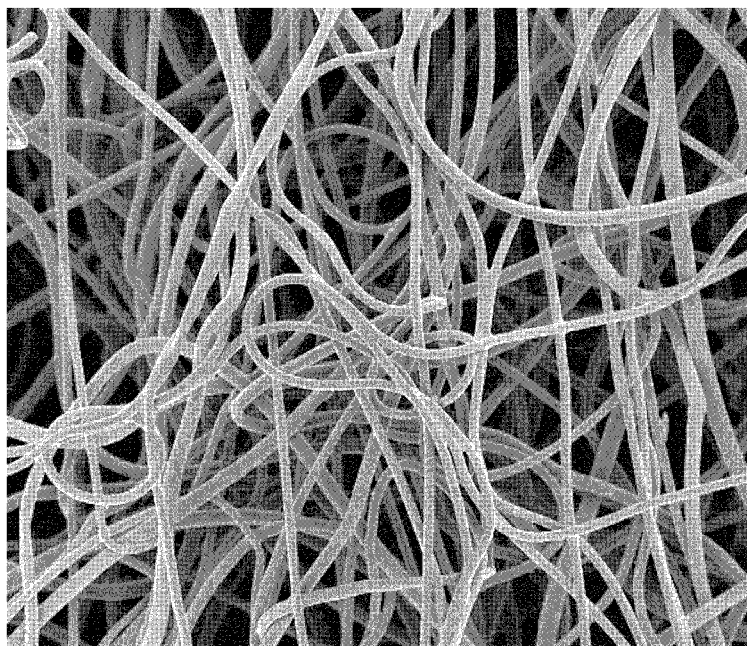
Figure 22C:
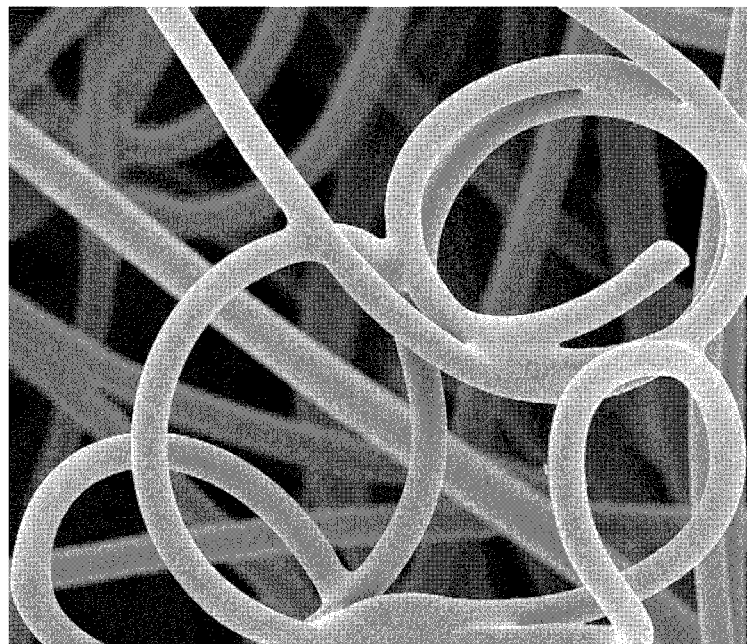

FIG. 22A illustrates a backscatter scanning electron microscope (SEM) plan view of a sample portion of ADL material at 70× magnification. FIG. 22B illustrates an SEM plan view of the ADL material at 140× magnification, and FIG. 21C illustrates an SEM plan view of the ADL material at 500× magnification. As illustrated by FIGS. 22A-22C, the ADL material can comprise a number of non-woven fibers extending at least partially horizontally (that is, parallel to the plane of the top and bottom surfaces of the material) for laterally/horizontally wicking fluid through the ADL material.

Figure 22D:
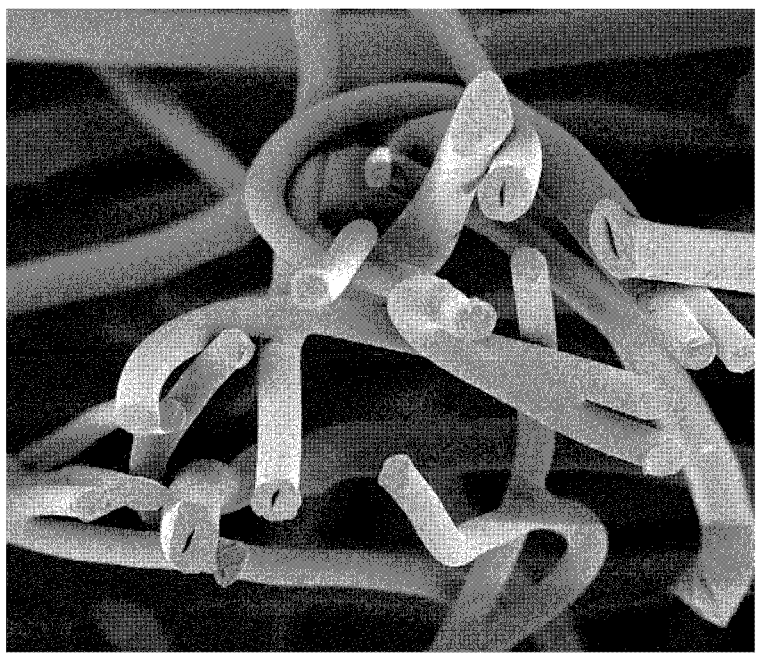
Figure 22E:
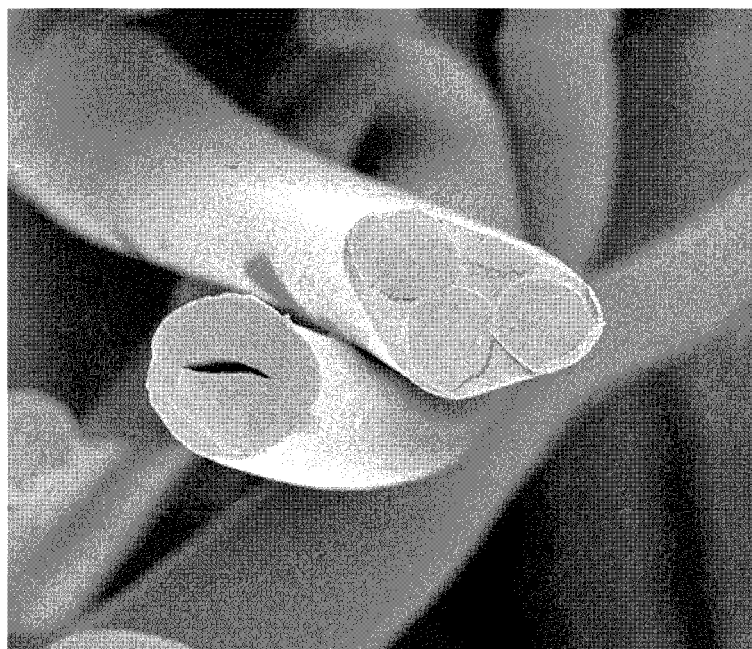

FIG. 22D illustrates an SEM cross sectional view of the ADL material at 500× magnification, and FIG. 22E illustrates an SEM cross sectional view of the ADL material at 1550× magnification. In the illustrated embodiment, the ADL material may consist of a mix of multiple fiber types. One may be a roughly cylindrical fiber. Another fiber may be a relatively flatter fiber having a centrally-located negative space. Another fiber may be a multi-component fiber that has at least one inner core fiber, in some embodiments three inner core fibers as in the illustrated sample, and an outer layer surrounding the inner core.

Figure 23A:
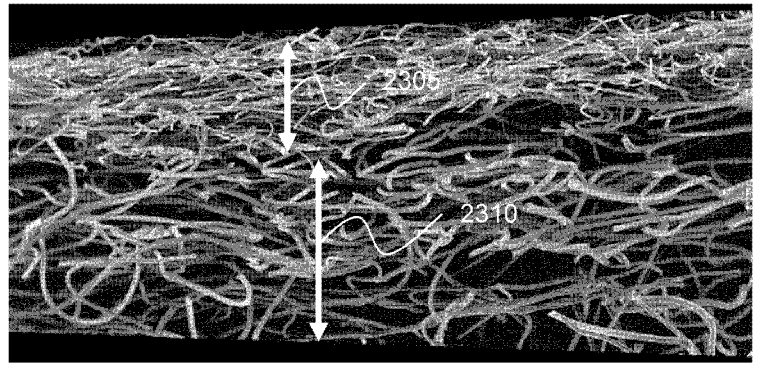
FIGS. 23A through 23E illustrate another embodiment of acquisition distribution layer material.
Figure 23B:
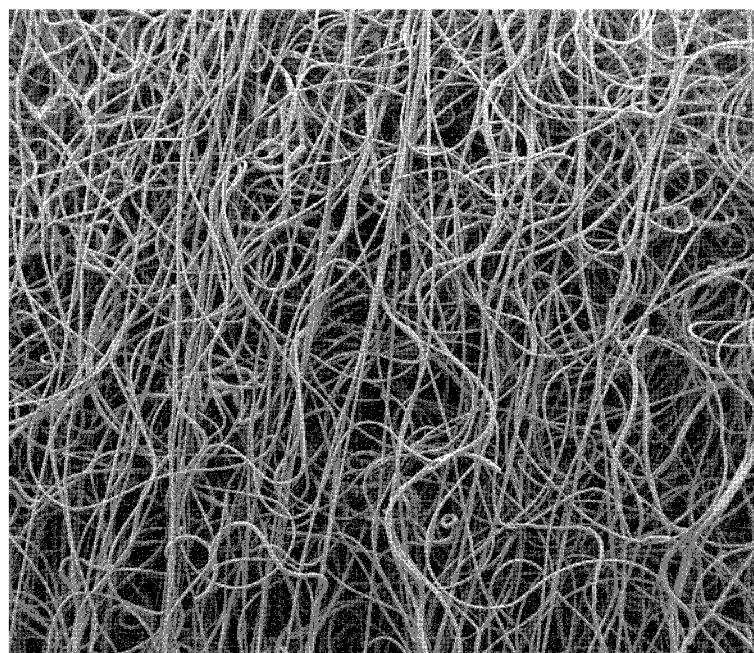
Figure 23C:
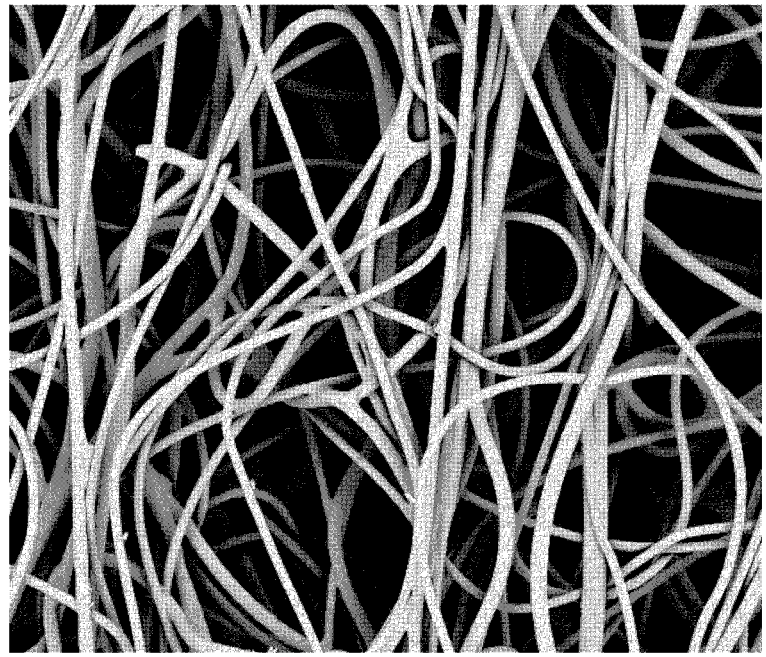
Figure 23D:
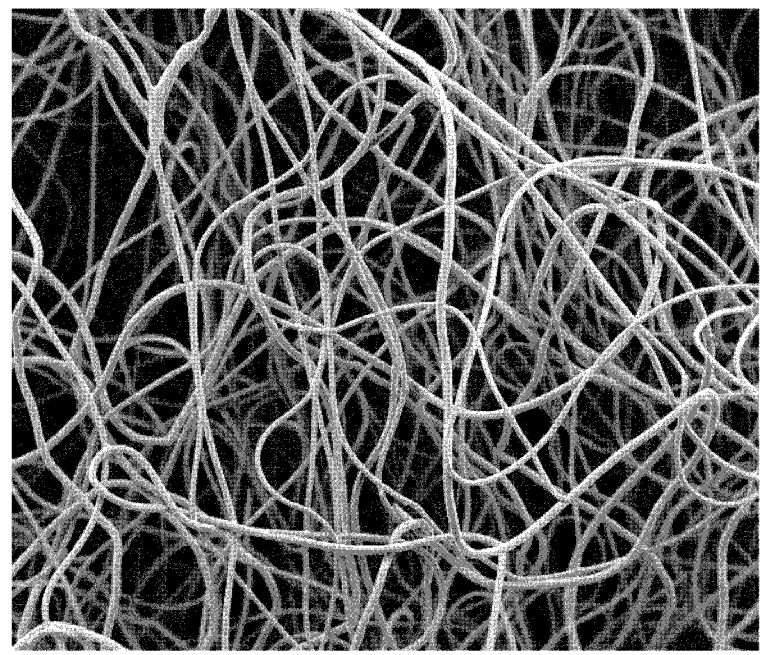
Figure 23E:
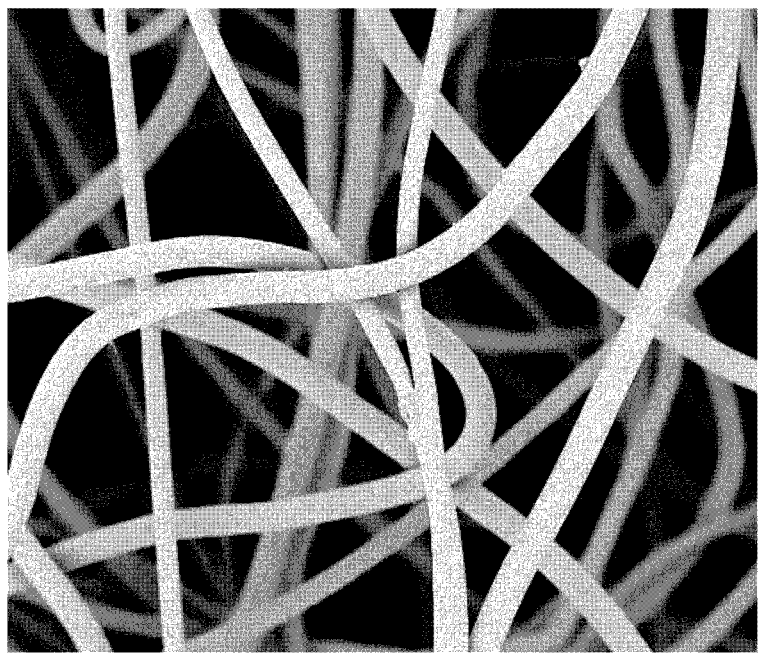

FIGS. 23A through 23E illustrate an example of Libeltex SlimCore TL4 that can be suitable for use as acquisition distribution layer material. FIG. 23A illustrates an SEM cross sectional view of a sample portion of ADL material at 50× magnification. The ADL material can include an upper layer 2305 and a lower layer 2310 having different densities, lofts, and thicknesses. For example, the upper layer 2305 can comprise a more dense, less lofted fiber configuration and can be approximately 730 μm thick in some embodiments. The lower layer 2310 can comprise a less dense, more lofted fiber configuration and can be approximately 1200 μm thick in some embodiments. FIG. 23B illustrates an SEM plan view of a sample portion of the denser upper layer 2305 at 70× magnification, and FIG. 23C illustrates an SEM plan view of a sample portion of the denser upper layer 2305 at 250× magnification. FIG. 23D illustrates an SEM plan view of a sample portion of the more lofted lower layer 2310 at 70× magnification, and FIG. 23E illustrates an SEM plan view of a sample portion of the more lofted lower layer 2310 at 250× magnification. As illustrated by FIGS. 23A-23E, the upper and lower layers 2305, 2310 of the ADL material can comprise different densities of a number of non-woven fibers extending at least partially horizontally (that is, parallel to the plane of the top and bottom surfaces of the material) for laterally/horizontally wicking fluid through the ADL material.

As illustrated by FIGS. 22A-23E, the non-woven fibers of the various illustrated ADL materials can extend more in a horizontal direction than in a vertical direction to aid in lateral wicking of fluids through the material. In some embodiments, a majority of the fiber volume may extend horizontally or substantially or generally horizontally. In another embodiment, 80%-90% (or approximately 80% to approximately 90%) or more of the fiber volume may extend horizontally, or substantially or generally horizontally. In another embodiment, all or substantially all of the fiber volume may extend horizontally, or substantially or generally horizontally. In some embodiments, a majority, 80%-90% (or approximately 80% to approximately 90%) of the fibers or more, or even all or substantially all of the fibers, span a distance perpendicular to the thickness of the ADL material (a horizontal or lateral distance) that is greater than the thickness of the ADL material. In some embodiments, the horizontal or lateral distance spanned by such fibers is 2 times (or about 2 times) or more, 3 times (or about 3 times) or more, 4 times (or about 4 times) or more, 5 times (or about 5 times) or more, or 10 times (or about 10 times) or more the thickness of the ADL material. The orientation of such fibers may promote lateral wicking of fluid through the ADL material. This may more evenly distribute fluid such as wound exudate throughout the ADL material. In some embodiments, the ratio of the amount of fluid wicked laterally across the ADL material to the amount of fluid wicked vertically through the ADL material under negative pressure may be 2:1 or more, or approximately 2:1 or more, or may be up to 10:1 or more, or approximately 10:1 or more, in some embodiments.

X. Terminology

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A wound treatment apparatus comprising:
   a wound dressing configured to be positioned over a wound site, the wound dressing comprising:
      a material layer comprising a plurality of cells defined by predefined cuts along a first surface thereof, wherein each cell of the plurality of cells is at least partially separated from an adjacent cell along a majority of every side of each said cell that faces an adjacent cell, wherein the plurality of cells comprise rectangular-shaped cells, wherein the plurality of cells of the material layer are configured to allow the material layer to conform to a non-planar surface;
      a backing layer over the material layer and comprising at least one orifice;
      a wound contact layer beneath the material layer and sealed to the backing layer; and
   a fluidic connector positioned over the at least one orifice configured to provide negative pressure through the wound dressing to the wound site;
   wherein each cell is partially connected to an adjacent cell of the plurality of cells by bridging portions that together with the plurality of cells form a single continuous material layer;
   wherein the bridging portions have a smaller height than surrounding cell portions.

2. The wound treatment apparatus of claim 1, wherein the plurality of cells are arranged in a regularly repeating grid pattern.

3. The wound treatment apparatus of claim 2, wherein the plurality of cells comprise square-shaped cells.

4. The wound treatment apparatus of claim 1, wherein the plurality of cells comprise cells having a shape selected from the group consisting of a square, rectangle, circle, pentagon, hexagon, octagon, and triangle.

5. The wound treatment apparatus of claim 1, wherein the plurality of cells comprise cells having a same shape and a same size.

6. The wound treatment apparatus of claim 1, wherein the predefined cuts comprise cuts parallel to a first orientation.

7. The wound treatment apparatus of claim 6, wherein the predefined cuts further comprise cuts parallel to a second orientation, the second orientation perpendicular to the first orientation.

8. The wound treatment apparatus of claim 1, wherein each cell of the plurality of cells is connected to an adjacent cell of the plurality of cells along every side of each said cell that faces a side of an adjacent cell.

9. The wound treatment apparatus of claim 1, wherein the material layer comprises an absorbent layer.

10. The wound treatment apparatus of claim 1, wherein the material layer comprises a foam layer.

11. The wound treatment apparatus of claim 1, further comprising a transmission layer beneath the material layer.

12. A wound treatment apparatus comprising:
   a wound dressing configured to be positioned over a wound site, the wound dressing comprising:
      a foam layer comprising a plurality of cells arranged in a regularly repeating rectangular-shaped grid pattern, wherein each cell of the plurality of cells is partially connected to an adjacent cell along every side of each said cell that faces a side of an adjacent cell, and wherein each cell of the plurality of cells is physically separated from an adjacent cell along a majority of every side of each said cell that faces a side of an adjacent cell, wherein the plurality of cells of the foam layer are configured to allow the foam layer to conform to a non-planar surface;
      a backing layer over the foam layer and comprising at least one orifice;
      a wound contact layer beneath the foam layer and sealed to the backing layer; and
   a fluidic connector positioned over the at least one orifice configured to provide negative pressure through the wound dressing to the wound site;
   wherein each cell is partially connected to an adjacent cell of the plurality of cells by bridging portions that together with the plurality of cells form a single continuous foam layer;
   wherein the bridging portions have a smaller height than surrounding cell portions.

13. The wound treatment apparatus of claim 12, wherein the plurality of cells are arranged in a regularly repeating square-shaped grid pattern.

14. The wound treatment apparatus of claim 12, wherein the bridging portions have a smaller width than surrounding cell portions.

15. A wound treatment apparatus comprising:
   a wound dressing configured to be positioned over a wound site, the wound dressing comprising:
      a material layer comprising a plurality of cells, wherein each cell of the plurality of cells is at least partially separated from an adjacent cell along every side of each said cell that faces an adjacent cell, wherein the plurality of cells of the material layer are configured to allow the material layer to conform to a non-planar surface;

a backing layer over the material layer and comprising at least one orifice;

a wound contact layer beneath the material layer and sealed to the backing layer; and a fluidic connector positioned over the at least one orifice configured to provide negative pressure through the wound dressing to the wound site;

wherein each cell is partially connected to an adjacent cell of the plurality of cells by bridging portions that together with the plurality of cells form a single continuous material layer;

wherein the bridging portions have a smaller height than surrounding cell portions.

16. The wound treatment apparatus of claim 15, wherein the plurality of cells are arranged in a regularly repeating pattern.

17. The wound treatment apparatus of claim 16, wherein the plurality of cells comprise cells having a same size and the same polygonal shape.

\* \* \* \* \*